US 7,604,955 B2

(12) United States Patent  
Chen et al.

(10) Patent No.: US 7,604,955 B2
(45) Date of Patent: Oct. 20, 2009

(54) IMMUNOGLOBULIN E VACCINES AND METHODS OF USE THEREOF

(75) Inventors: Swey-Shen Alex Chen, 6740 Nancy Ridge Dr., San Diego, CA (US) 92121; Yong-Min Yang, San Diego, CA (US); Theresa J. Barankiewicz, San Diego, CA (US); Zhong Chen, San Diego, CA (US)

(73) Assignee: Swey-Shen Alex Chen

(*) Notice: Subject to any disclaimer, the term of this patent is extended or adjusted under 35 U.S.C. 154(b) by 502 days.

(21) Appl. No.: 10/214,524

(22) Filed: Aug. 8, 2002

(65) Prior Publication Data

US 2003/0073142 A1 Apr. 17, 2003

Related U.S. Application Data

(60) Provisional application No. 60/312,120, filed on Aug. 13, 2001.

(51) Int. Cl.
*G01N 33/53* (2006.01)
(52) U.S. Cl. .................. 435/7.24; 435/7.92; 530/328
(58) Field of Classification Search .................. 435/7.24; 424/184.1; 514/2, 8
See application file for complete search history.

(56) References Cited

U.S. PATENT DOCUMENTS

| | | | |
|---|---|---|---|
| 4,946,778 A | 8/1990 | Ladner et al. |
| 5,028,592 A | 7/1991 | Lipton |
| 5,180,805 A | 1/1993 | Gould et al. |
| 5,254,671 A | 10/1993 | Chang |
| 5,428,133 A | 6/1995 | Chang |
| 5,583,202 A | 12/1996 | Zanetti |
| 5,589,466 A | 12/1996 | Felgner et al. |
| 5,629,415 A | 5/1997 | Hollis |
| 5,653,980 A | 8/1997 | Hellman |
| 5,703,055 A | 12/1997 | Felgner et al. |
| 5,846,946 A | 12/1998 | Huebner et al. |
| 5,910,488 A | 6/1999 | Nabel et al. |
| 5,955,076 A | 9/1999 | Stanworth et al. |
| 6,025,485 A | 2/2000 | Kamb et al. |
| 6,214,804 B1 | 4/2001 | Felgner et al. |
| 6,258,549 B1 | 7/2001 | Auer et al. |
| 6,268,411 B1 | 7/2001 | Schneck et al. |
| 6,299,875 B1 | 10/2001 | Caplan |
| 6,342,220 B1 | 1/2002 | Adams et al. |
| 6,346,249 B1 | 2/2002 | Barbas et al. |
| 6,355,619 B1 | 3/2002 | Miller et al. |
| 6,384,018 B1 | 5/2002 | Content et al. |
| 6,406,706 B1 | 6/2002 | Davis et al. |
| 6,413,942 B1 | 7/2002 | Felgner et al. |
| 2002/0012909 A1 | 1/2002 | Plaksin |
| 2004/0156838 A1* | 8/2004 | Klysner et al. ........ 424/130.1 |

FOREIGN PATENT DOCUMENTS

| WO | WO 95/26365 A1 | 10/1995 |
|---|---|---|
| WO | WO 96/12740 A1 | 5/1996 |
| WO | WO 97/31948 | 9/1997 |
| WO | WO 00/20027 A2 | 4/2000 |
| WO | WO 00/20574 A2 | 4/2000 |
| WO | WO 00/26246 A2 | 5/2000 |
| WO | WO 00/63252 A1 | 10/2000 |
| WO | WO 01/68861 A2 | 9/2001 |
| WO | WO 01/69253 A2 | 9/2001 |
| WO | WO 02/20038 | 3/2002 |
| WO | WO 02/26781 A2 | 4/2002 |
| WO | WO 02/34287 A2 | 5/2002 |

OTHER PUBLICATIONS

Stuber et al., "Assessment of major histocompatibility complex class I interaction with Epstein-Barr virus and human immunodeficiency virus peptides by elevation of membrane H-2 and HLA in peptide loading defficient cells" Eur J Immunol (1992) 22:2697-2703.*
Chen, S S. "Mechanisms of IgE tolerance: dual regulatory T cell lesions in perinatal IgE tolerance" Eur J Immunol (1991) 21:2461-2467.*
De Panfilis, G. "CD8+ cytolytic T lymphocytes and the skin" Exp Dermatol (1998) 7:121-131.*
Steinbrink et al., Blood, 2002, 99:2468-2476.*
Janeway et al., Immunobiology, 3rd edition, 1997, Garland Press, pp. 4:2-4:9.*
Abedi et al., 1998, Nucleic Acids Res., 26:623.
Achatz et al., 1997, Science, 276:409.
Andersen et al., 2000, Tissue Antigens, 55:519.
Batista et al., 1995, J. Immunol., 154:209.
Bhardwaj, 2001, Trends Mol. Med., 7:388.
Billetta et al., 1991, Proc. Natl. Acad. Sci., 88:4713.
Billetta et al., 1995, Eur. J. Immunol., 25:776.
Billetta, 1992, Immunomethods, 1:41.
Brusic et al., 2002, Immunol. Cell Biol., 80:280.
Carreno and Collins, 2002, Annu. Rev. Immunol., 20:29.
Chang, 2000, Nature Biotech, 18:157.
Chen, 1990, J. Immunol. Meth., 135:129.
Christmann et al., 1999, Protein Eng., 12:797.
Christmann et al., 2001, J. Immunol. Methods, 257:163.
Cohen et al., 1998, FASEB J., 12:1611.
Come et al., 1997, J. Clin. Inv., 99:879.
Crameri et al., 1996, Nature Biotech., 14:315.
De Bruijn, 1991, Eur. J. Immunol., 21:2963.
Falk et al., 1991, Nature, 351:290.
Felgner et al., 1987, Proc. Natl. Acad. Sci., 84:7413.
Frauwirth and Thompson, 2002, J. Clin. Invest., 109:295.
Garman et al., 2000, Nature, 406:259.
Gerloni et al., 1999, J. Immunol., 162:3782.
Gunneriusson et al., 1999, Appl. Env. Microbiol., 65:4134.

(Continued)

Primary Examiner—Michael Szperka

(57) ABSTRACT

The present invention concerns the prophylaxis or therapy of immunoglobulin E-mediated disease conditions. The present invention discloses methods for identifying peptides that induce a cytotoxic T-lymphocyte response against immunoglobulin E. The present invention further discloses compositions that are able to elicit in a mammal a cytotoxic T-lymphocyte response to naturally processed and presented immunoglobulin E peptides, and methods for their use.

11 Claims, 26 Drawing Sheets

OTHER PUBLICATIONS

Gurunathan et al., 2000, Annu. Rev. Immunol.,18:927.
He, 1999, J. Immunol. Methods, 231:105.
Helm et al., 1988, Nature, 331:180.
Hoerr et al., 2000, Eur. J. Immunol., 30:1.
Inaba, 1990, J. Exp. Med., 172:631.
Jerne, 1993, Scan. J. Immunol., 38:1.
Jung et al., 1993, Science, 259:984.
Katona et al., 1991, J. Immunol,. 146:4215.
Klinman et al., 1999, Vaccine, 17:19.
Liu, 1980, J. Immunol., 124:2728.
Mayordomo et al., 1997, Stem Cells, 15:94.
Milgrom et al., 1999, N. Engl. J. Med., 341:1966.
Minev et al., 2000, Proc. Natl. Acad. Sci., 97:4796.
Mössner and Plückthun, 2001, Chimia, 55:324.
Neuberger, 1995, Nature, 314:268.
Oettgen et al., 1994, Nature, 370:367.
Pamer and Cresswell, 1998, Annu. Rev. Immunol., 16:323.
Peng et al., 1992, J. Immunol., 148:129.
Phizicky and Fields, 1995, Microbiol. Rev., 59:94.
Samulski et al., 1989, J. Virol., 63:3822.
Schaffitzel et al., 1999, J. Immunol. Methods, 231:119.
Scheerlinck, 2001, Vaccine, 19:2647.
Schoenberger et al., 1998, Nature, 393:480.
Schueler-Furman et al., 2000, Protein Sci., 9:1838.
Shastri et al., 2002, Annu. Rev. Immunol., 20:463.
Skerra, 2000, J. Mol. Recognit., 13:167.
Smith, 1985, Science, 228:1315.
Somia et al., 1999 Nature Biotechnol., 17:224.
Steinman and Pope, 2002, J. Clin. Invest., 109:1519.
Sun et al., 1991, J. Immunol., 146,199.
Theobald et al., 1997, J. Exp Med., 185:833.
Tsien, 1998, Annu. Rev. Biochem., 67:509.
Vogel et al., 2000, J. Mol. Biol., 298:729.
Wang et al., 1996, Eur. J. Immunol., 26:1043.
Wilson et al., 2001, Proc. Natl. Acad. Sci., 98:3750.
Wittrup, 2001, Curr. Opin. Biotechnol., 12:395.
Yeung and Wittrup, 2002, Biotechnol. Prog., 18:212.
Ying et al., 1999, Nature Med., 5:823.
Zhang at al., 1992, J. Exp. Med., 176:233.
Zhang et al., 1994, J. Biol. Chem., 269:456.
Jin, X, et al., "Indentification of Subdominant Cytotoxic T Lymphocyte . . . " AIDS Res. Human Retroviruses, 16:67-76 (2000).
Aveskogh, M, et al., "Evidence for an early appearance fo modern post-switch isotyes in mammalian evolution . . . " Eur. J. Immunol., 28:2738-50 (1998).
Paliard, X, et al., "Induction of Herper Simplex Virus gB-Specific Cytotoxic T Lymphocytes in TAP1-Deficient Mice . . . " Virology, 282:56-64 (2001).
Macary, P.A., et al., "Ovalbumin-Specific, MHC Class I-Restricted . . . " J. Immunology, 160:580-7 (1998).
Stevens, J, et al., "Peptide length preferences for rat and mouse MHC class I molecules using random . . . " Eur. J. Immunol., 28:1272-9 (1998).

* cited by examiner

IgE natural peptides as self markers and targets on IgE-producing cells

FIG. 4

| Peptide | Amino Acid Sequence | SEQ ID NO. |
|---|---|---|
| p1 | Leu Tyr Cys Phe Ile Tyr Gly His Ile | 1 |
| p2 | Ile Tyr Gly His Ile Leu Asn Asp Val | 2 |
| p3 | Leu Leu His Ser Ser Cys Asp Pro Asn Ala Phe His Ser Thr Ile Gln Leu Tyr Cys Phe Ile Tyr Gly His Ile Leu Asn Asp Val Ser Val Ser Trp Leu Met Asp Asp Arg Glu | 4 |
| p4 | Ile Gln Leu Tyr Cys Phe Ile Try Gly His Ile Leu Asn Asp Val Ser Val | 5 |

FIG. 7
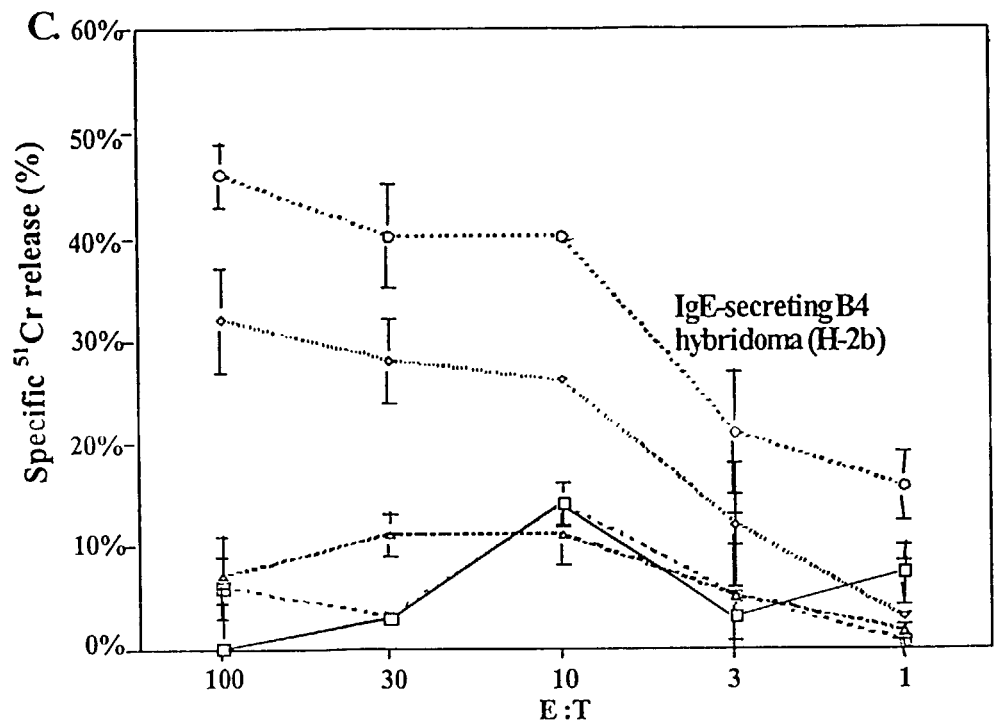
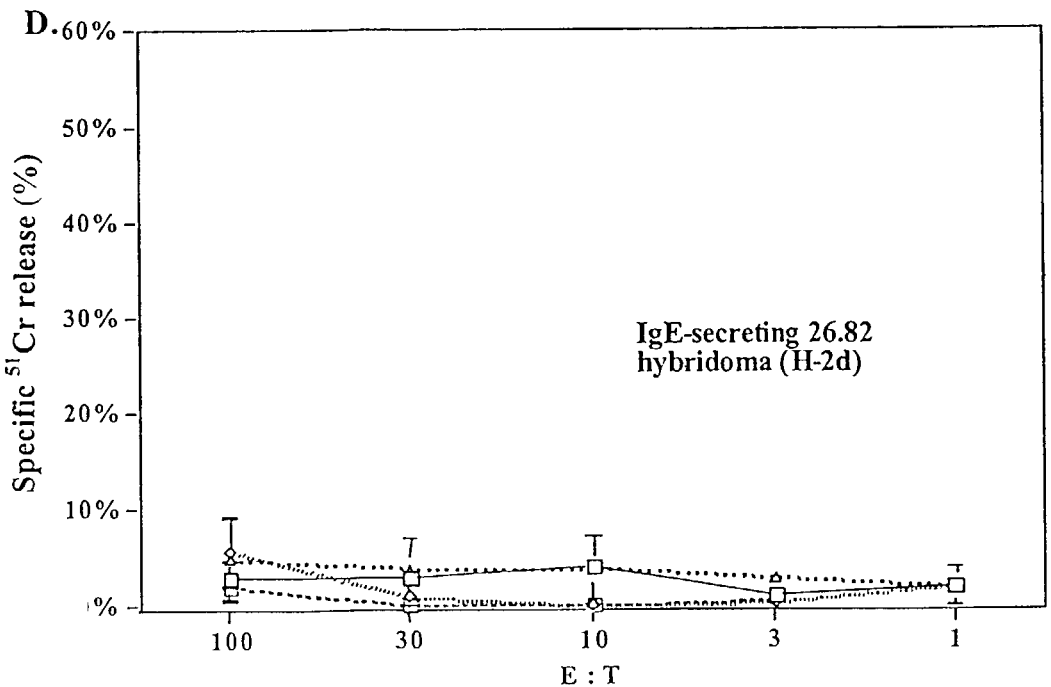

FIG. 12

A.
Cloning of Human IgE cDNA Isoforms

B.
Adeno X Construct of Human IgE cDNA

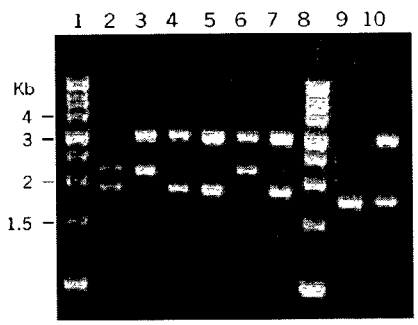

Lane 1 & 8  1kb ladder
Lane 2.  IgE cDNA isoforms by RT-PCR from U266
Lane 3.  pGemT1-13, membrane long isoform, classical
Lane 4  pGemT3 11, membrane short isoform
Lane 5.  pGemT2-13, membrane short isoform
Lane 6.  pGmeT1a, membrane long isoform
Lane 7.  pGemT3a, membrane short isoform
Lane 9  IgE cDNA secreted isoform by RT PCR from U266
Lane 10  pGemT-S1, cDNA clone of IgE secreted isoform

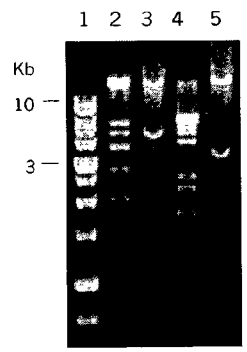

Lane 1.  1kb Ladder
Lane 2.  pAd lacZ digested with Xba I/Not I
Lane 3.  pAd-lac Z digested with PI-Sce I/ I-Ceu I
Lane 4.  pAd IgEml digested with Xba I/Kpn I
Lane 5.  pAd IgEml digested with PI-Sce I/ I-Ceu

FIG. 15A

Comparison of IgE from Different Species

FIG. 15B

Lane 1 and 8. DNA Mass Markers
Lane 2.   Clone no. 6/4 uncut
Lane 3.                Sph I/Bgl II cut
Lane 4.                Sph I/BssH II cut
Lane 5.   Clone no. 6/5 uncut
Lane 6.                Sph I/Bgl II cut
Lane 7.                Sph I/BssH II cut

SEQUENCE LISTING

```
<160> NUMBER OF SEQ ID NOS: 61

<210> SEQ ID NO 1
<211> LENGTH: 9
<212> TYPE: PRT
<213> ORGANISM: Mouse (Mus musculus)

<400> SEQUENCE: 1

Leu Tyr Cys Phe Ile Tyr Gly His Ile
1               5

<210> SEQ ID NO 2
<211> LENGTH: 9
<212> TYPE: PRT
<213> ORGANISM: Mouse (Mus musculus)

<400> SEQUENCE: 2

Ile Tyr Gly His Ile Leu Asn Asp Val
1               5

<210> SEQ ID NO 3
<211> LENGTH: 17
<212> TYPE: PRT
<213> ORGANISM: Chicken (Gallus gallus)

<400> SEQUENCE: 3

Ile Ser Gln Ala Val His Ala Ala His Ala Glu Ile Asn Glu Ala Gly
1               5                   10                  15

Arg

<210> SEQ ID NO 4
<211> LENGTH: 39
<212> TYPE: PRT
<213> ORGANISM: Mouse (Mus musculus)

<400> SEQUENCE: 4

Leu Leu His Ser Ser Cys Asp Pro Asn Ala Phe His Ser Thr Ile Gln
1               5                   10                  15

Leu Tyr Cys Phe Ile Tyr Gly His Ile Leu Asn Asp Val Ser Val Ser
            20                  25                  30

Trp Leu Met Asp Asp Arg Glu
        35

<210> SEQ ID NO 5
<211> LENGTH: 17
<212> TYPE: PRT
<213> ORGANISM: Mouse (Mus musculus)

<400> SEQUENCE: 5
```

```
Ile Gln Leu Tyr Cys Phe Ile Tyr Gly His Ile Leu Asn Asp Val Ser
1               5                   10                  15

Val

<210> SEQ ID NO 6
<211> LENGTH: 9
<212> TYPE: PRT
<213> ORGANISM: Human (Homo sapiens)

<400> SEQUENCE: 6

Trp Leu Ser Asp Arg Thr Tyr Thr Cys
1               5

<210> SEQ ID NO 7
<211> LENGTH: 9
<212> TYPE: PRT
<213> ORGANISM: Human (Homo sapiens)

<400> SEQUENCE: 7

Trp Val Asp Asn Lys Thr Phe Ser Val
1               5

<210> SEQ ID NO 8
<211> LENGTH: 9
<212> TYPE: PRT
<213> ORGANISM: Human (Homo sapiens)

<400> SEQUENCE: 8

Leu Leu Thr Val Ser Gly Ala Trp Ala
1               5

<210> SEQ ID NO 9
<211> LENGTH: 9
<212> TYPE: PRT
<213> ORGANISM: Human (Homo sapiens)

<400> SEQUENCE: 9

Gln Leu Pro Asp Ala Arg His Ser Thr
1               5

<210> SEQ ID NO 10
<211> LENGTH: 9
<212> TYPE: PRT
<213> ORGANISM: Human (Homo sapiens)

<400> SEQUENCE: 10

Thr Gln Ser Pro Ser Val Phe Pro Leu
1               5

<210> SEQ ID NO 11
<211> LENGTH: 9
<212> TYPE: PRT
<213> ORGANISM: Human (Homo sapiens)

<400> SEQUENCE: 11

Ala Leu Met Arg Ser Thr Thr Lys Thr
1               5

<210> SEQ ID NO 12
<211> LENGTH: 9
<212> TYPE: PRT
<213> ORGANISM: Human (Homo sapiens)

<400> SEQUENCE: 12
```

Thr Leu Thr Leu Ser Gly His Tyr Ala
1               5

<210> SEQ ID NO 13
<211> LENGTH: 9
<212> TYPE: PRT
<213> ORGANISM: Human (Homo sapiens)

<400> SEQUENCE: 13

Thr Leu Pro Ala Thr Thr Leu Thr Leu
1               5

<210> SEQ ID NO 14
<211> LENGTH: 9
<212> TYPE: PRT
<213> ORGANISM: Human (Homo sapiens)

<400> SEQUENCE: 14

Ser Leu Asn Gly Thr Thr Met Thr Leu
1               5

<210> SEQ ID NO 15
<211> LENGTH: 9
<212> TYPE: PRT
<213> ORGANISM: Human (Homo sapiens)

<400> SEQUENCE: 15

Thr Leu Ser Gly His Tyr Ala Thr Ile
1               5

<210> SEQ ID NO 16
<211> LENGTH: 9
<212> TYPE: PRT
<213> ORGANISM: Human (Homo sapiens)

<400> SEQUENCE: 16

Thr Met Thr Leu Pro Ala Thr Thr Leu
1               5

<210> SEQ ID NO 17
<211> LENGTH: 9
<212> TYPE: PRT
<213> ORGANISM: Human (Homo sapiens)

<400> SEQUENCE: 17

Leu Thr Leu Ser Gln Lys His Trp Leu
1               5

<210> SEQ ID NO 18
<211> LENGTH: 9
<212> TYPE: PRT
<213> ORGANISM: human immunodeficiency virus

<400> SEQUENCE: 18

Ile Leu Lys Glu Pro Val His Gly Val
1               5

<210> SEQ ID NO 19
<211> LENGTH: 21
<212> TYPE: DNA
<213> ORGANISM: Artificial sequence
<220> FEATURE:
<223> OTHER INFORMATION: Synthetic construct

<400> SEQUENCE: 19

```
cctggtggag cgtgagtggc c                                            21

<210> SEQ ID NO 20
<211> LENGTH: 26
<212> TYPE: DNA
<213> ORGANISM: Artificial sequence
<220> FEATURE:
<223> OTHER INFORMATION: Synthetic construct

<400> SEQUENCE: 20
cctccacaca gagcccatcc gtcttc                                       26

<210> SEQ ID NO 21
<211> LENGTH: 31
<212> TYPE: DNA
<213> ORGANISM: Artificial sequence
<220> FEATURE:
<223> OTHER INFORMATION: Synthetic construct

<400> SEQUENCE: 21
tatagtcgac accatgggat ggagctgtat c                                 31

<210> SEQ ID NO 22
<211> LENGTH: 25
<212> TYPE: DNA
<213> ORGANISM: Artificial sequence
<220> FEATURE:
<223> OTHER INFORMATION: Synthetic construct

<400> SEQUENCE: 22
taccgctgaa ggttttgttg tcgac                                        25

<210> SEQ ID NO 23
<211> LENGTH: 23
<212> TYPE: DNA
<213> ORGANISM: Artificial sequence
<220> FEATURE:
<223> OTHER INFORMATION: Synthetic construct

<400> SEQUENCE: 23
gagagctccg ttcctcacca tgg                                          23

<210> SEQ ID NO 24
<211> LENGTH: 27
<212> TYPE: DNA
<213> ORGANISM: Artificial sequence
<220> FEATURE:
<223> OTHER INFORMATION: Synthetic construct

<400> SEQUENCE: 24
cgtcatttac cgggatttac agacacc                                      27

<210> SEQ ID NO 25
<211> LENGTH: 496
<212> TYPE: PRT
<213> ORGANISM: Cat (Felis catus)

<400> SEQUENCE: 25

Ala Tyr Ile Ser Ser Gly Gly Asn Thr Asp Tyr Ala Asp Ser Val Lys
 1               5                  10                  15

Gly Arg Phe Ser Ile Ser Arg Asp Asn Ala Lys Asn Thr Leu Tyr Leu
            20                  25                  30

Gln Met Thr Ser Leu Lys Thr Glu Asp Thr Ala Thr Tyr Tyr Cys Ala
        35                  40                  45
```

```
Arg Gly Thr Gly Val Ile Pro Asp Tyr Trp Gly Gln Gly Ala Leu Val
 50                  55                  60

Thr Val Ser Ser Thr Ser Ile Gln Ala Pro Leu Val Phe Pro Leu Ala
 65                  70                  75                  80

Thr Cys Cys Lys Gly Thr Ile Ala Thr Ala Pro Ser Val Thr Leu Gly
                 85                  90                  95

Cys Leu Val Thr Gly Tyr Phe Pro Met Pro Val Thr Val Thr Trp Asp
                100                 105                 110

Ala Arg Ser Leu Asn Lys Ser Val Val Thr Leu Pro Ala Thr Leu Gln
            115                 120                 125

Glu Asn Ser Gly Leu Tyr Thr Thr Ser His Val Thr Val Ser Gly
    130                 135                 140

Glu Trp Ala Lys Gln Lys Phe Thr Cys Ser Val Ala His Ala Glu Ser
145                 150                 155                 160

Pro Thr Ile Asn Lys Thr Val Ser Ala Cys Thr Met Asn Phe Ile Pro
                165                 170                 175

Pro Thr Val Lys Leu Phe His Ser Ser Cys Asn Pro Leu Gly Asp Thr
                180                 185                 190

Gly Ser Thr Ile Gln Leu Leu Cys Leu Ile Ser Gly Tyr Val Pro Gly
            195                 200                 205

Asp Met Glu Val Thr Trp Leu Val Asp Gly Gln Lys Ala Thr Asn Ile
210                 215                 220

Phe Pro Tyr Thr Ala Pro Gly Lys Gln Glu Gly Lys Val Thr Ser Thr
225                 230                 235                 240

His Ser Glu Leu Asn Ile Thr Gln Gly Glu Trp Val Ser Gln Lys Thr
                245                 250                 255

Tyr Thr Cys Gln Val Thr Tyr Gln Gly Phe Thr Phe Glu Asp His Ala
                260                 265                 270

Arg Lys Cys Thr Glu Ser Asp Pro Arg Gly Val Ser Thr Tyr Leu Ser
            275                 280                 285

Pro Pro Ser Pro Leu Asp Leu Tyr Val His Lys Ser Pro Lys Ile Thr
290                 295                 300

Cys Leu Val Val Asp Leu Ala Asn Thr Asp Gly Met Ile Leu Thr Trp
305                 310                 315                 320

Ser Arg Glu Asn Gly Glu Ser Val His Pro Asp Pro Met Val Lys Lys
                325                 330                 335

Thr Gln Tyr Asn Gly Thr Ile Thr Val Thr Ser Thr Leu Pro Val Asp
                340                 345                 350

Ala Thr Asp Trp Val Glu Gly Glu Thr Tyr Gln Cys Lys Val Thr His
            355                 360                 365

Pro Asp Leu Pro Lys Asp Ile Val Arg Ser Ile Ala Lys Ala Pro Gly
370                 375                 380

Arg Arg Phe Pro Glu Val Tyr Val Phe Leu Pro Pro Glu Gly Glu
385                 390                 395                 400

Pro Lys Thr Lys Asp Lys Val Thr Leu Thr Cys Leu Ile Gln Asn Phe
                405                 410                 415

Phe Pro Pro Asp Ile Ser Val Gln Trp Leu His Asn Asp Ser Pro Val
                420                 425                 430

Arg Thr Glu Gln Gln Ala Thr Thr Trp Pro His Lys Ala Thr Gly Pro
            435                 440                 445

Ser Pro Ala Phe Phe Val Phe Ser Arg Leu Glu Val Ser Arg Ala Asp
450                 455                 460
```

```
Trp Glu Gln Arg Asp Val Phe Thr Cys Gln Val Val His Glu Ala Leu
465                 470                 475                 480

Pro Gly Phe Arg Thr Leu Lys Lys Ser Val Ser Lys Asn Pro Gly Lys
                485                 490                 495

<210> SEQ ID NO 26
<211> LENGTH: 426
<212> TYPE: PRT
<213> ORGANISM: Chimpanzee (Pan troglodytes)

<400> SEQUENCE: 26

Pro Thr Arg Ser Pro Ser Leu Phe Pro Leu Thr Arg Cys Cys Lys Asn
1               5                   10                  15

Ile Pro Ser Asn Ala Thr Ser Val Thr Leu Gly Cys Leu Ala Met Gly
            20                  25                  30

Tyr Phe Pro Glu Pro Val Met Val Thr Trp Asp Ala Gly Ser Leu Asn
        35                  40                  45

Gly Thr Thr Met Thr Leu Pro Ala Thr Thr Leu Thr Pro Ser Gly His
    50                  55                  60

Tyr Ala Thr Ile Ser Leu Leu Thr Val Ser Gly Ala Trp Ala Lys Gln
65                  70                  75                  80

Met Phe Thr Cys Arg Val Ala His Thr Pro Ser Ser Thr Asp Trp Val
                85                  90                  95

Asp Asn Lys Thr Phe Ser Val Cys Ser Arg Asp Phe Thr Pro Thr Val
            100                 105                 110

Lys Val Leu Gln Ser Ser Cys Asp Gly Gly His Phe Pro Pro Thr
        115                 120                 125

Ile Gln Leu Leu Cys Leu Val Ser Gly Tyr Thr Pro Gly Thr Ile Asn
    130                 135                 140

Ile Thr Trp Leu Glu Asp Gly Gln Val Met Asp Val Asp Leu Ser Thr
145                 150                 155                 160

Ala Ser Ala Thr Gln Glu Gly Glu Leu Ala Ser Thr Gln Ser Glu Leu
                165                 170                 175

Thr Leu Ser Gln Lys His Trp Leu Ser Asp Arg Thr Tyr Thr Cys Gln
            180                 185                 190

Val Thr Tyr Gln Gly Gly Thr Phe Glu Asp Ser Thr Lys Lys Cys Ala
        195                 200                 205

Asp Ser Asn Pro Arg Gly Val Ser Ala Tyr Leu Ser Arg Pro Ser Pro
    210                 215                 220

Phe Asp Leu Phe Ile Arg Lys Ser Pro Thr Ile Thr Cys Leu Val Val
225                 230                 235                 240

Asp Leu Ala Pro Ser Lys Gly Thr Val Asn Leu Thr Trp Ser Arg Ala
                245                 250                 255

Ser Gly Lys Pro Val Asn His Ser Thr Arg Lys Gln Glu Lys Gln Arg
            260                 265                 270

Asn Gly Thr Leu Thr Val Thr Ser Thr Leu Pro Val Gly Thr Arg Asp
        275                 280                 285

Trp Ile Glu Gly Glu Thr Tyr Gln Cys Arg Val Thr His Pro His Leu
    290                 295                 300

Pro Arg Ala Leu Val Arg Ser Thr Thr Lys Thr Ser Gly Pro Arg Ala
305                 310                 315                 320

Ala Pro Glu Val Tyr Ala Phe Ala Thr Pro Glu Gly Pro Gly Ser Arg
                325                 330                 335

Asp Lys Arg Thr Leu Ala Cys Leu Ile Gln Asn Phe Met Pro Glu Asp
            340                 345                 350
```

```
Ile Ser Val Gln Trp Leu His Asn Glu Val Gln Leu Pro Asp Ala Arg
        355                 360                 365

His Ser Thr Thr Gln Pro His Lys Thr Lys Gly Ser Gly Phe Phe Val
        370                 375                 380

Phe Ser Arg Leu Glu Val Thr Arg Ala Glu Trp Glu Gln Lys Asp Glu
385                 390                 395                 400

Phe Ile Cys Arg Ala Val His Glu Ala Ala Ser Pro Ser Gln Thr Val
                405                 410                 415

Gln Arg Thr Val Ser Val Asn Pro Gly Lys
        420                 425

<210> SEQ ID NO 27
<211> LENGTH: 426
<212> TYPE: PRT
<213> ORGANISM: Cow (Bos taurus)

<400> SEQUENCE: 27

Val Ser Ser Ala Ser Ile Gln Ala Pro Ser Ile Tyr Pro Leu Arg Leu
1               5                   10                  15

Cys Cys Thr Glu Glu Ala Arg Val Arg Leu Gly Cys Leu Val Lys Asp
                20                  25                  30

Tyr Leu Pro Gly Ser Val Thr Val Thr Trp Asp Thr Val Pro Leu Asp
            35                  40                  45

Gly Ser Thr Leu Thr Phe Pro Ser Ile Gln Met Ala Ser Ser Ser Leu
        50                  55                  60

Tyr Ile Thr Thr Ser Gln Leu Thr Ile Ser Gly Glu Gln Ser Lys Glu
65                  70                  75                  80

Phe Thr Cys Arg Val Leu His Pro Glu Thr Ile Gln Leu Asn Lys Thr
                85                  90                  95

Ser Thr Glu Cys Val Lys Asn Phe Ser Asp Pro Ser Val Lys Leu Phe
            100                 105                 110

Phe Ser Ser Cys Asn Pro Asn Gly Asp Thr Gln Thr Thr Ile His Leu
        115                 120                 125

Leu Cys Arg Ile Ser Ala Tyr Thr Pro Gly Lys Ile Lys Val Thr Trp
130                 135                 140

Leu Val Asp Gly Leu Gln Ser Glu Glu Leu Tyr Ala Arg Ser Gly Pro
145                 150                 155                 160

Glu Ile Gln Glu Gly Asn Leu Thr Ser Thr Tyr Ser Glu Val Asn Ile
                165                 170                 175

Thr Gln Gly Gln Trp Val Ser Glu Lys Thr Tyr Thr Cys Arg Val Asn
            180                 185                 190

Tyr Tyr Gly Tyr Asn Phe Glu Ser His Ala His Arg Cys Thr Ala Glu
        195                 200                 205

Ser Glu Pro Arg Val Ser Ala Tyr Leu Ser Pro Pro Thr Pro Leu Glu
210                 215                 220

Leu Tyr Val Asn Lys Ser Pro Lys Ile Thr Cys Leu Val Val Asp Leu
225                 230                 235                 240

Ala Asn Glu Lys Asn Leu Ser Leu Thr Trp Ser Arg Ala Asn Gly Lys
                245                 250                 255

Pro Val His Ala Gly Pro Pro Glu Ile Lys Arg Gln Phe Asn Gly Thr
            260                 265                 270

Val Thr Val Thr Ser Thr Leu Pro Val Asp Val Thr Asp Trp Val Glu
        275                 280                 285

Gly Glu Thr Tyr Tyr Cys Lys Val Ser His Arg Asp Leu Pro Thr Asp
```

```
                290                 295                 300
Ile Gln Arg Ser Ile Ser Lys Asp Val Gly Lys Arg Leu Ala Pro Lys
305                 310                 315                 320

Asp Tyr Val Phe Leu Ala Asp Gly Lys Glu Leu Glu Asn Glu Glu
                325                 330                 335

Leu Thr Leu Thr Cys Met Ile Gln Asn Phe Pro Arg Asp Ile Phe
                340                 345                 350

Val Arg Trp Leu His Asn Lys Glu Leu Met Gly Ala Asp Gln His Thr
                355                 360                 365

Thr Thr Gln Pro His Arg Asp Asp Asn Thr Pro Ala Phe Phe Ala
370                 375                 380

Tyr Ser Arg Leu Ala Val Pro Arg Ala Asn Trp Lys Arg Gly Asp Glu
385                 390                 395                 400

Phe Thr Ser Gln Val Ile His Glu Ala Leu Pro Arg Thr Arg Thr Leu
                405                 410                 415

Glu Lys Ser Val Phe Ile Asn Ser Gly Lys
                420                 425

<210> SEQ ID NO 28
<211> LENGTH: 426
<212> TYPE: PRT
<213> ORGANISM: Dog (Canis familiaris)

<400> SEQUENCE: 28

Thr Ser Gln Asp Leu Ser Val Phe Pro Leu Ala Ser Cys Cys Lys Asp
1               5                   10                  15

Asn Ile Ala Ser Thr Ser Val Thr Leu Gly Cys Leu Val Thr Gly Tyr
                20                  25                  30

Leu Pro Met Ser Thr Thr Val Thr Trp Asp Thr Gly Ser Leu Asn Lys
                35                  40                  45

Asn Val Thr Thr Phe Pro Thr Thr Phe His Glu Thr Tyr Gly Leu His
                50                  55                  60

Ser Ile Val Ser Gln Val Thr Ala Ser Gly Lys Trp Ala Lys Gln Arg
65              70                  75                  80

Phe Thr Cys Ser Val Ala His Ala Glu Ser Thr Ala Ile Asn Lys Thr
                85                  90                  95

Phe Ser Ala Cys Ala Leu Asn Phe Ile Pro Pro Thr Val Lys Leu Phe
                100                 105                 110

His Ser Ser Cys Asn Pro Val Gly Asp Thr His Thr Thr Ile Gln Leu
                115                 120                 125

Leu Cys Leu Ile Ser Gly Tyr Val Pro Gly Asp Met Glu Val Ile Trp
                130                 135                 140

Leu Val Asp Gly Gln Lys Ala Thr Asn Ile Phe Pro Tyr Thr Ala Pro
145                 150                 155                 160

Gly Thr Lys Glu Gly Asn Val Thr Ser Thr His Ser Glu Leu Asn Ile
                165                 170                 175

Thr Gln Gly Glu Trp Val Ser Gln Lys Thr Tyr Thr Cys Gln Val Thr
                180                 185                 190

Tyr Gln Gly Phe Thr Phe Lys Asp Glu Ala Arg Lys Cys Ser Glu Ser
                195                 200                 205

Asp Pro Arg Gly Val Thr Ser Tyr Leu Ser Pro Ser Pro Leu Asp
                210                 215                 220

Leu Tyr Val His Lys Ala Pro Lys Ile Thr Cys Leu Val Val Asp Leu
225                 230                 235                 240
```

```
Ala Thr Met Glu Gly Met Asn Leu Thr Trp Tyr Arg Glu Ser Lys Glu
                245                 250                 255

Pro Val Asn Pro Gly Pro Leu Asn Lys Lys Asp His Phe Asn Gly Thr
            260                 265                 270

Ile Thr Val Thr Ser Thr Leu Pro Val Asn Thr Asn Asp Trp Ile Glu
            275                 280                 285

Gly Glu Thr Tyr Tyr Cys Arg Val Thr His Pro His Leu Pro Lys Asp
        290                 295                 300

Ile Val Arg Ser Ile Ala Lys Ala Pro Gly Lys Arg Ala Pro Pro Asp
305                 310                 315                 320

Val Tyr Leu Phe Leu Pro Pro Glu Glu Gln Gly Thr Lys Asp Arg
                325                 330                 335

Val Thr Leu Thr Cys Leu Ile Gln Asn Phe Phe Pro Ala Asp Ile Ser
                340                 345                 350

Val Gln Trp Leu Arg Asn Asp Ser Pro Ile Gln Thr Asp Gln Tyr Thr
                355                 360                 365

Thr Thr Gly Pro His Lys Val Ser Gly Ser Arg Pro Ala Phe Phe Ile
        370                 375                 380

Phe Ser Arg Leu Glu Val Ser Arg Val Asp Trp Glu Gln Lys Asn Lys
385                 390                 395                 400

Phe Thr Cys Gln Val Val His Glu Ala Leu Ser Gly Ser Arg Ile Leu
                405                 410                 415

Gln Lys Trp Val Ser Lys Thr Pro Gly Lys
                420                 425

<210> SEQ ID NO 29
<211> LENGTH: 577
<212> TYPE: PRT
<213> ORGANISM: Duckbilled platypus (Ornithorhynchus anatinus)

<400> SEQUENCE: 29

Met Arg Ser Ala Leu Ser Leu Leu Ser Ile Leu Thr Leu Leu Gln Gly
1               5                   10                  15

Val Gln Gly Asp Val Gln Leu Val Glu Ser Gly Gly Asp Val Arg Gln
            20                  25                  30

Pro Gly Gly Ser Leu Ser Leu Ser Cys Lys Val Ser Gly Phe Thr Leu
        35                  40                  45

Asn Ala His Tyr Met His Trp Ile Arg Gln Gly Pro Gly Thr Gly Leu
    50                  55                  60

Glu Trp Ile Gly Tyr Ile Ser Ser Gly Gly Ile Ile Asp Tyr Ala Asp
65                  70                  75                  80

Ser Val Arg Gly Arg Phe Thr Ile Ser Arg Asp Asn Ser Lys Ser Leu
                85                  90                  95

Leu Asn Leu His Met Ser Ser Leu Lys Thr Glu Asp Thr Ala Leu Tyr
            100                 105                 110

Tyr Cys Ala Arg Ala Ala Asp Tyr Ser Thr Cys Ser Ser Thr Ser Ser
        115                 120                 125

Tyr Tyr Cys Ala Leu Ala Lys Trp Gly Gln Gly Thr Met Val Thr Val
    130                 135                 140

Ser Ser Val Ser Ser Lys Ala Pro Ser Val Phe Pro Leu Val Pro Cys
145                 150                 155                 160

Cys Asp Gly Thr Asp Ser Ser Ala Val Thr Leu Gly Cys Leu Val Thr
                165                 170                 175

Gly Tyr Ile Pro Glu Pro Val Thr Val Arg Trp Asn Ser Gly Asp Leu
            180                 185                 190
```

```
Val Lys Gly Val Thr Thr Phe Pro Ser Val Phe Asp Ser Gln Ser Gly
        195                 200                 205
Leu Tyr Thr Met Ser Ser Gln Val Thr Val Ser Gln Glu Ser Trp Gln
    210                 215                 220
Ser Gln Thr Phe Thr Cys Asn Val Glu Gln Met Ala Thr Lys Thr Lys
225                 230                 235                 240
Ile Asn Thr Glu Val Tyr Ser Asp Cys Ser Lys Asp Pro Ile Pro Pro
                245                 250                 255
Thr Val Lys Leu Leu His Ser Ser Cys Asp Pro Arg Gly Asp Ser Gln
            260                 265                 270
Ala Ser Ile Glu Leu Leu Cys Leu Ile Thr Gly Tyr Ser Pro Ala Gly
        275                 280                 285
Ile Gln Val Asp Trp Leu Val Asp Gly Gln Lys Ala Glu Asn Leu Phe
    290                 295                 300
Pro Tyr Thr Ala Pro Lys Arg Glu Gly Asn Arg Ser Phe Ser Ser
305                 310                 315                 320
His Ser Glu Val Asn Ile Thr Gln Asp Gln Trp Leu Ser Gly Lys Thr
                325                 330                 335
Phe Thr Cys Gln Val Thr His Leu Ala Asp Lys Lys Thr Tyr Gln Asp
            340                 345                 350
Ser Ala Arg Lys Cys Ala Asp Ser Asp Pro Arg Gly Ile Thr Val Phe
        355                 360                 365
Leu Thr Pro Pro Ser Pro Thr Asp Leu Tyr Ile Ser Lys Thr Pro Lys
    370                 375                 380
Leu Thr Cys Leu Ile Ile Asp Leu Val Ser Thr Glu Gly Met Glu Val
385                 390                 395                 400
Thr Trp Ser Arg Glu Ser Gly Thr Pro Leu Ser Ala Glu Ser Phe Glu
                405                 410                 415
Glu Gln Lys Gln Phe Asn Gly Thr Met Ser Phe Ile Ser Thr Val Pro
            420                 425                 430
Val Asn Ile Gln Asp Trp Asn Glu Gly Glu Ser Tyr Thr Cys Arg Val
        435                 440                 445
Ala His Pro Asp Leu Pro Ser Pro Ile Ile Lys Thr Val Thr Lys Leu
    450                 455                 460
Pro Gly Lys Arg Leu Ala Pro Glu Val Tyr Ala Phe Pro Pro His Gln
465                 470                 475                 480
Ala Glu Val Ser His Gly Asp Ser Leu Ser Leu Thr Cys Leu Ile Arg
                485                 490                 495
Gly Phe Tyr Pro Glu Asn Ile Ser Val Arg Trp Leu Leu Asp Asn Lys
            500                 505                 510
Pro Leu Pro Thr Glu His Tyr Arg Thr Thr Lys Pro Leu Lys Asp Gln
        515                 520                 525
Gly Pro Asp Pro Ala Tyr Phe Leu Tyr Ser Arg Leu Ala Val Asn Lys
    530                 535                 540
Ser Thr Trp Glu Gln Gly Asn Val Tyr Thr Cys Gln Val Val His Glu
545                 550                 555                 560
Ala Leu Pro Ser Arg Asn Thr Glu Arg Lys Phe Gln His Thr Ser Gly
                565                 570                 575
Asn

<210> SEQ ID NO 30
<211> LENGTH: 569
<212> TYPE: PRT
```

<213> ORGANISM: Horse (Equus caballus)

<400> SEQUENCE: 30

```
Pro Leu Lys Arg Glu Ser His Leu Gln Glu His Glu Ser Pro Val Val
1               5                   10                  15
Leu Pro Leu Ser Gly Asp Arg Pro Thr Cys Val Leu Ser Gln Val Gln
            20                  25                  30
Leu Lys Glu Ser Gly Pro Gly Leu Val Lys Pro Ser Gln Thr Leu Ser
        35                  40                  45
Leu Thr Cys Thr Val Ser Gly Leu Ser Leu Ser Ser Asn Ser Val Gly
    50                  55                  60
Trp Val Arg Gln Ala Pro Gly Lys Gly Leu Glu Trp Val Gly Phe Arg
65                  70                  75                  80
Ser Gly Gly Glu Glu Tyr Tyr Asn Pro Ala Leu Lys Ser Arg Ala
            85                  90                  95
Thr Ile Thr Glu Asp Ala Ala Lys Ser Gln Val Tyr Leu Asp Ala Glu
            100                 105                 110
Gln Val Thr Gly Glu Ala Thr Ala Val Tyr Tyr Cys Ala Glu Val Tyr
        115                 120                 125
Asn Asn Tyr Leu Tyr Tyr Gly Ile Lys Glu Leu Gly Ala Arg Gly Leu
    130                 135                 140
Leu Val Thr Val Ser Ser Val Ser Lys Gln Ala Pro Leu Ile Phe Pro
145                 150                 155                 160
Leu Ala Ala Cys Cys Lys Asp Thr Lys Thr Thr Asn Ile Thr Leu Gly
                165                 170                 175
Cys Leu Val Lys Gly Tyr Phe Pro Gly Ala Trp Asp Ala Gly Pro Leu
            180                 185                 190
Asn Pro Ser Thr Met Thr Phe Pro Ala Val Phe Asp Gln Thr Ser Gly
        195                 200                 205
Leu Tyr Thr Thr Ile Ser Arg Val Val Ala Ser Gly Lys Trp Ala Lys
    210                 215                 220
Gln Lys Phe Thr Cys Gly Val Val His Ser Gln Glu Thr Phe Asn Lys
225                 230                 235                 240
Thr Phe Asn Ala Cys Ile Val Thr Phe Thr Pro Thr Val Lys Leu
                245                 250                 255
Phe His Ser Ser Cys Asp Pro Gly Gly Asp Ser His Thr Thr Ile Gln
            260                 265                 270
Leu Leu Cys Leu Ile Ser Asp Tyr Thr Pro Gly Asp Ile Asp Ile Val
        275                 280                 285
Trp Leu Ile Glu Gly Gln Lys Val Asp Glu Gln Phe Pro Thr Gln Ala
    290                 295                 300
Ser Met Lys Gln Glu Gly Ser Trp Pro Pro Thr His Ser Glu Leu Asn
305                 310                 315                 320
Ile Asn Gln Gly Gln Trp Ala Ser Glu Asn Thr Tyr Thr Cys Gln Val
                325                 330                 335
Thr Tyr Lys Asp Met Ile Phe Asn Gln Ala Arg Lys Cys Thr Glu Ser
            340                 345                 350
Asp Pro Pro Gly Val Ser Val Tyr Leu Ser Pro Pro Ser Pro Leu Asp
        355                 360                 365
Leu Tyr Val Ser Lys Thr Pro Lys Ile Thr Cys Leu Val Val Asp Leu
    370                 375                 380
Ala Asn Val Gln Gly Leu Ser Leu Asn Trp Ser Arg Glu Ser Gly Glu
385                 390                 395                 400
```

```
Pro Leu Gln Lys His Thr Leu Ala Thr Ser Glu Gln Phe Asn Lys Thr
                405                 410                 415

Phe Ser Val Thr Ser Thr Leu Pro Val Asp Thr Thr Asp Trp Ile Glu
            420                 425                 430

Gly Glu Thr Tyr Lys Cys Thr Val Ser His Pro Asp Leu Pro Arg Glu
        435                 440                 445

Val Val Arg Ser Ile Ala Lys Ala Pro Gly Lys Arg Leu Ser Pro Glu
    450                 455                 460

Val Tyr Val Phe Leu Pro Pro Glu Glu Asp Gln Ser Ser Lys Asp Lys
465                 470                 475                 480

Val Thr Leu Thr Cys Leu Ile Gln Asn Phe Phe Pro Ala Asp Ile Ser
                485                 490                 495

Val Gln Trp Arg Arg Asn Asn Val Leu Ile Gln Thr Asp Gln Gln Ala
            500                 505                 510

Thr Thr Arg Pro Gln Lys Ala Asn Gly Pro Asp Pro Ala Phe Phe Val
        515                 520                 525

Phe Ser Arg Leu Glu Val Ser Arg Ala Glu Trp Glu Gln Lys Asn Lys
    530                 535                 540

Phe Ala Cys Lys Val Val His Glu Ala Leu Ser Gln Arg Thr Leu Gln
545                 550                 555                 560

Lys Glu Val Ser Lys Asp Pro Gly Lys
                565

<210> SEQ ID NO 31
<211> LENGTH: 421
<212> TYPE: PRT
<213> ORGANISM: Mouse (Mus musculus)

<400> SEQUENCE: 31

Ser Ile Arg Asn Pro Gln Leu Tyr Pro Leu Lys Pro Cys Lys Gly Thr
1               5                   10                  15

Ala Ser Met Thr Leu Gly Cys Leu Val Lys Asp Tyr Phe Pro Asn Pro
                20                  25                  30

Val Thr Val Thr Trp Tyr Ser Asp Ser Leu Asn Met Ser Thr Val Asn
            35                  40                  45

Phe Pro Ala Leu Gly Ser Glu Leu Lys Val Thr Thr Ser Gln Val Thr
        50                  55                  60

Ser Trp Gly Lys Ser Ala Lys Asn Phe Thr Cys His Val Thr His Pro
65                  70                  75                  80

Pro Ser Phe Asn Glu Ser Arg Thr Ile Leu Val Arg Pro Val Asn Ile
                85                  90                  95

Thr Glu Pro Thr Leu Glu Leu Leu His Ser Ser Cys Asp Pro Asn Ala
            100                 105                 110

Phe His Ser Thr Ile Gln Leu Tyr Cys Phe Ile Tyr Gly His Ile Leu
        115                 120                 125

Asn Asp Val Ser Val Ser Trp Leu Met Asp Asp Arg Glu Ile Thr Asp
130                 135                 140

Thr Leu Ala Gln Thr Val Leu Ile Lys Glu Glu Gly Lys Leu Ala Ser
145                 150                 155                 160

Thr Cys Ser Lys Leu Asn Ile Thr Glu Gln Gln Trp Met Ser Glu Ser
                165                 170                 175

Thr Phe Thr Cys Lys Val Thr Ser Gln Gly Val Asp Tyr Leu Ala His
            180                 185                 190

Thr Arg Arg Cys Pro Asp His Glu Pro Arg Gly Val Ile Thr Tyr Leu
        195                 200                 205
```

Ile Pro Pro Ser Pro Leu Asp Leu Tyr Gln Asn Gly Ala Pro Lys Leu
    210                 215                 220

Thr Cys Leu Val Val Asp Leu Glu Ser Glu Lys Asn Val Asn Val Thr
225                 230                 235                 240

Trp Asn Gln Glu Lys Lys Thr Ser Val Ser Ala Ser Gln Trp Tyr Thr
                245                 250                 255

Lys His His Asn Asn Ala Thr Thr Ser Ile Thr Ser Ile Leu Pro Val
            260                 265                 270

Val Ala Lys Asp Trp Ile Glu Gly Tyr Gly Tyr Gln Cys Ile Val Asp
        275                 280                 285

His Pro Asp Phe Pro Lys Pro Ile Val Arg Ser Ile Thr Lys Thr Pro
    290                 295                 300

Gly Gln Arg Ser Ala Pro Glu Val Tyr Val Phe Pro Pro Glu Glu
305                 310                 315                 320

Glu Ser Glu Asp Lys Arg Thr Leu Thr Cys Leu Ile Gln Asn Phe Phe
                325                 330                 335

Pro Glu Asp Ile Ser Val Gln Trp Leu Gly Asp Gly Lys Leu Ile Ser
            340                 345                 350

Asn Ser Gln His Ser Thr Thr Thr Pro Leu Lys Ser Asn Gly Ser Asn
        355                 360                 365

Gln Gly Phe Phe Ile Phe Ser Arg Leu Glu Val Ala Lys Thr Leu Trp
    370                 375                 380

Thr Gln Arg Lys Gln Phe Thr Cys Gln Val Ile His Glu Ala Leu Gln
385                 390                 395                 400

Lys Pro Arg Lys Leu Glu Lys Thr Ile Ser Thr Ser Leu Gly Asn Thr
                405                 410                 415

Ser Leu Arg Pro Ser
            420

<210> SEQ ID NO 32
<211> LENGTH: 446
<212> TYPE: PRT
<213> ORGANISM: Opossum (Monodelphis domestica)

<400> SEQUENCE: 32

Tyr Gly Tyr Arg Leu Asp Asn Trp Gly Lys Gly Thr Thr Val Thr Val
1               5                   10                  15

Ser Ser Glu Pro Leu Thr Ala Pro Ser Val Phe Pro Leu Met Ser Cys
                20                  25                  30

Cys Asp Ser Asn Ser Gly Gly Lys Ala Phe Leu Gly Cys Leu Ala Thr
            35                  40                  45

Gly Tyr Phe Pro Glu Ser Val Thr Ile Asn Trp Asn Ser Glu Val Leu
        50                  55                  60

Asp Glu Ile Ile Thr Asn Phe Pro Ala Thr Tyr Asp Pro Thr Ser Gly
65                  70                  75                  80

Arg Tyr Thr Thr Thr Ser Gln Leu Thr Val Ser Asp Leu Ser Asp Gln
                85                  90                  95

Glu Phe Thr Cys Ser Val Asp His Leu Pro Thr Ser Thr Lys Ile Lys
            100                 105                 110

Lys Thr Leu Ser Leu Pro Glu Cys Gly Pro Val Thr Ile Ile Pro Pro
        115                 120                 125

Thr Val Lys Leu Phe His Ser Ser Cys Asp Pro Arg Gly Asp Ala His
    130                 135                 140

Ser Thr Ile Gln Leu Leu Cys Leu Val Ser Gly Phe Ser Pro Ala Lys

```
                145                 150                 155                 160
Val His Val Thr Trp Leu Val Asp Gly Gln Glu Ala Glu Asn Leu Phe
                165                 170                 175

Pro Tyr Thr Thr Arg Pro Lys Arg Glu Gly Gln Thr Phe Ser Leu
            180                 185                 190

Gln Ser Glu Val Asn Ile Thr Gln Gly Gln Trp Met Ser Ser Asn Thr
            195                 200                 205

Tyr Thr Cys His Val Lys His Asn Gly Ser Ile Phe Glu Asp Ser Ala
            210                 215                 220

Gln Lys Cys Ser Asp Thr Asp Pro Arg Gly Ile Ser Ala Tyr Ile Leu
225                 230                 235                 240

Pro Pro Thr Pro Gln Asp Leu Phe Val Lys Lys Val Pro Thr Ile Gly
                245                 250                 255

Cys Leu Ile Val Asp Leu Ala Ser Ala Glu Asn Val Lys Val Thr Trp
                260                 265                 270

Ser Arg Glu Ser Gly Pro Val Asn Pro Ser Leu Val Val Lys
            275                 280                 285

Glu Gln Tyr Asn Gly Thr Phe Thr Val Thr Ser His Leu Pro Val Asn
            290                 295                 300

Thr Asp Asp Trp Ile Glu Gly Asp Thr Tyr Thr Cys Arg Leu Glu Ser
305                 310                 315                 320

Pro Asp Met Pro Val Pro Leu Ile Arg Thr Ile Ser Lys Ala Pro Gly
                325                 330                 335

Lys Arg Leu Ala Pro Glu Val Tyr Met Leu Pro Pro Ser Pro Glu Glu
            340                 345                 350

Thr Gly Thr Thr Arg Thr Val Thr Cys Leu Ile Arg Gly Phe Tyr Pro
            355                 360                 365

Ser Glu Ile Ser Val Gln Trp Leu Phe Asn Asn Glu Glu Asp His Thr
            370                 375                 380

Gly His His Thr Thr Thr Arg Pro Gln Lys Asp His Gly Thr Asp Pro
385                 390                 395                 400

Ser Phe Phe Leu Tyr Ser Arg Met Leu Val Asn Lys Ser Ile Trp Glu
                405                 410                 415

Lys Gly Asn Leu Val Thr Cys Arg Val Val His Glu Ala Leu Pro Gly
            420                 425                 430

Ser Arg Thr Leu Glu Lys Ser Leu His Tyr Ser Ala Gly Asn
            435                 440                 445

<210> SEQ ID NO 33
<211> LENGTH: 567
<212> TYPE: PRT
<213> ORGANISM: Pig (Sus scrofa)

<400> SEQUENCE: 33

Met Glu Phe Arg Leu Asn Trp Val Val Leu Phe Ala Leu Leu Gln Gly
1               5                   10                  15

Val Gln Gly Glu Glu Lys Leu Val Glu Ser Gly Gly Gly Leu Val Gln
            20                  25                  30

Pro Gly Gly Ser Leu Arg Leu Ser Cys Val Gly Ser Gly Phe Thr Phe
        35                  40                  45

Ser Ser Tyr Ser Val Asn Trp Val Arg Gln Ala Pro Gly Lys Gly Leu
    50                  55                  60

Glu Trp Leu Ala Ala Ile Pro Thr Ser Ala Gly Ser Thr Tyr Tyr Ala
65                  70                  75                  80
```

-continued

```
Asp Ser Val Lys Gly Arg Phe Thr Ile Ser Arg Asp Asn Ser Gln Asn
                85                  90                  95

Thr Ala Tyr Leu Glu Met Ser Ser Leu Arg Thr Glu Asp Thr Ala Arg
            100                 105                 110

Tyr Tyr Cys Ala Lys Thr Val Ala Ala Ser Gly Val Asn Ile Tyr Phe
        115                 120                 125

Val Asp Val Trp Gly Pro Gly Val Glu Val Val Ser Ser Ala Ser
130                 135                 140

Ile Gln Gly Pro Leu Val Tyr Pro Leu Thr Ser Cys Cys Lys Thr Gly
145                 150                 155                 160

Ala Thr Ser Lys Thr Leu Gly Cys Leu Val Arg Gly Tyr Phe Pro Glu
                165                 170                 175

Pro Val Thr Val Thr Trp Asp Thr Gly Ser Leu Asn Ser Ser Thr Leu
            180                 185                 190

Thr Phe Pro Ala Val Gln Asp Ser Ser Ser Leu Tyr Thr Val Thr
        195                 200                 205

Ser Gln Val Thr Ile Leu Gly Glu Trp Thr Asn Gln Lys Leu Thr Cys
210                 215                 220

Ser Val Ala His Ala Ala Asn Thr Thr Ile Arg Thr Ile Thr Gly Cys
225                 230                 235                 240

Thr Lys Asn Phe Thr Asp Pro Ser Leu Arg Phe Phe Tyr Ser Ser Cys
                245                 250                 255

Asp Pro His Gly Asp Ala Gln Ala Thr Ile His Leu Arg Cys Tyr Ile
            260                 265                 270

Ser Gly Tyr Thr Pro Gly Lys Met Lys Val Thr Trp Leu Val Asp Gly
        275                 280                 285

Gln Glu Asp Arg Asn Leu Phe Ser Tyr Thr Ala Pro Asp Gln Leu Glu
290                 295                 300

Gly Lys Leu Ala Ser Thr Tyr Ser Glu Val Asn Ile Thr Gln Gly Gln
305                 310                 315                 320

Trp Ala Ser Gln Ile Thr Tyr Thr Cys Gln Val Ser Tyr Tyr Gly Phe
                325                 330                 335

Ile Tyr Glu Lys His Ala Leu Arg Cys Thr Ala Glu Ser Glu Pro Arg
            340                 345                 350

Gly Val Ser Ala Tyr Leu Ser Pro Pro Thr Pro Leu Asp Leu Tyr Val
        355                 360                 365

His Lys Ser Pro Lys Leu Thr Cys Leu Val Val Asp Leu Ala Ser Ser
370                 375                 380

Glu Asn Val Asn Leu Leu Trp Ser Arg Glu Asn Lys Gly Gly Val Ile
385                 390                 395                 400

Leu Pro Pro Pro Gly Pro Val Ile Lys Pro Gln Phe Asn Gly Thr
                405                 410                 415

Phe Ser Ala Thr Ser Thr Leu Pro Val Asn Val Ser Asp Trp Ile Glu
            420                 425                 430

Gly Glu Thr Tyr Tyr Cys Asn Val Thr His Pro Asp Leu Pro Lys Pro
        435                 440                 445

Ile Leu Arg Ser Ile Ser Lys Gly Pro Gly Lys Arg Val Thr Pro Glu
450                 455                 460

Val Tyr Val Leu Trp Ser Pro Asp Glu Leu Lys Lys Gly Arg Leu Thr
465                 470                 475                 480

Leu Thr Cys Leu Ile Gln Asn Phe Phe Pro Ala Asp Ile Ser Val Leu
                485                 490                 495

Trp Leu Arg Asn Asp Ala Pro Val Gln Ala Asp Arg His Ser Thr Thr
```

-continued

```
              500                 505                 510
Arg Pro His Lys Ala Ser Asp Ser Leu Pro Ser Phe Phe Val Tyr Ser
            515                 520                 525

Arg Leu Val Val Ser Gln Ser Asp Trp Glu Gln Asn Lys Phe Ala Cys
        530                 535                 540

Glu Val Ile His Glu Ala Leu Pro Gly Ser Arg Thr Leu Gln Lys Glu
545                 550                 555                 560

Val Ser Lys Asn Pro Gly Lys
                565

<210> SEQ ID NO 34
<211> LENGTH: 428
<212> TYPE: PRT
<213> ORGANISM: Rat (Rattus norvegicus)

<400> SEQUENCE: 34

Ser Val Lys Ala Pro Ser Leu Tyr Pro Leu Pro Cys Ser Ser Glu
1               5                  10                  15

Asn Thr Ala Ser Val Thr Leu Gly Cys Leu Val Lys Asp Tyr Phe Pro
            20                  25                  30

Asp Pro Val Thr Val Thr Trp Tyr Ser Asp Ser Leu Asn Thr Ser Thr
        35                  40                  45

Met Asn Phe Pro Ser Val Gly Ser Asp Leu Lys Thr Thr Thr Ser Gln
50                  55                  60

Met Thr Ser Trp Gly Lys Ser Ala Lys Asn Phe Thr Cys His Val Thr
65                  70                  75                  80

His Ala Pro Ser Thr Phe Val Ser Asp Leu Thr Ile Arg Ala Arg Pro
                85                  90                  95

Val Asn Ile Thr Lys Pro Thr Val Asp Leu Leu His Ser Ser Cys Asp
            100                 105                 110

Pro Asn Ala Phe His Ser Thr Ile Gln Leu Tyr Cys Phe Val Tyr Gly
        115                 120                 125

His Ile Gln Asn Asp Val Ser Ile His Trp Leu Met Asp Asp Arg Lys
    130                 135                 140

Ile Tyr Glu Thr His Ala Gln Asn Val Leu Ile Lys Glu Glu Gly Lys
145                 150                 155                 160

Leu Ala Ser Thr Tyr Ser Arg Leu Asn Ile Thr Gln Gln Gln Trp Met
                165                 170                 175

Ser Glu Ser Thr Phe Thr Cys Lys Val Thr Ser Gln Gly Glu Asn Tyr
            180                 185                 190

Trp Ala His Thr Arg Arg Cys Ser Asp Asp Glu Pro Arg Gly Val Ile
        195                 200                 205

Thr Tyr Leu Ile Pro Pro Ser Pro Leu Asp Leu Tyr Glu Asn Gly Thr
    210                 215                 220

Pro Lys Leu Thr Cys Leu Val Leu Asp Leu Glu Ser Glu Glu Asn Ile
225                 230                 235                 240

Thr Val Thr Trp Val Arg Glu Arg Lys Lys Ser Ile Gly Ser Ala Ser
                245                 250                 255

Gln Arg Ser Thr Lys His His Asn Ala Thr Thr Ser Ile Thr Ser Ile
            260                 265                 270

Leu Pro Val Asp Ala Lys Asp Trp Ile Glu Gly Glu Gly Tyr Gln Cys
        275                 280                 285

Arg Val Asp His Pro His Phe Pro Lys Pro Ile Val Arg Ser Ile Thr
    290                 295                 300
```

-continued

```
Lys Ala Pro Gly Lys Arg Ser Ala Pro Glu Val Tyr Val Phe Leu Pro
305                 310                 315                 320

Pro Glu Glu Glu Lys Asp Lys Arg Thr Leu Thr Cys Leu Ile Gln
            325                 330                 335

Asn Phe Phe Pro Glu Asp Ile Ser Val Gln Trp Leu Gln Asp Ser Lys
            340                 345                 350

Leu Ile Pro Lys Ser Gln His Ser Thr Thr Pro Leu Lys Tyr Asn
        355                 360                 365

Gly Ser Asn Gln Arg Phe Phe Ile Phe Ser Arg Leu Glu Val Thr Lys
        370                 375                 380

Ala Leu Trp Thr Gln Thr Lys Gln Phe Thr Cys Arg Val Ile His Glu
385                 390                 395                 400

Ala Leu Arg Glu Pro Arg Lys Leu Glu Arg Thr Ile Ser Lys Ser Leu
                405                 410                 415

Gly Asn Thr Ser Leu Arg Pro Ser Gln Ala Ser Met
                420                 425
```

<210> SEQ ID NO 35
<211> LENGTH: 563
<212> TYPE: PRT
<213> ORGANISM: Sheep (Ovis aries)

<400> SEQUENCE: 35

```
Asp Glu Pro Thr Val Asp Pro Pro Leu Cys Ala Leu Ser Pro Gln Arg
1               5                   10                  15

Val Leu Ser Gln Val Arg Leu Gln Glu Ser Gly Pro Ser Leu Val Lys
            20                  25                  30

Pro Ser Gln Thr Leu Ser Leu Thr Cys Thr Val Ser Gly Phe Ser Leu
        35                  40                  45

Asp Asp Asp Pro Val Gly Trp Val Arg Gln Ala Pro Gly Lys Val Pro
    50                  55                  60

Glu Trp Leu Gly Leu Ile Gly Tyr Asp Gly Asp Thr Tyr Tyr Asn Pro
65                  70                  75                  80

Ala Leu Lys Ser Arg Leu Ser Ile Thr Arg Asp Thr Ser Lys Ser Gln
                85                  90                  95

Val Ser Leu Ser Leu Ile Ser Val Thr Thr Glu Asp Thr Ala Val Tyr
            100                 105                 110

Tyr Cys Thr Gly Glu Pro Thr Tyr Ser Lys Tyr Ala Ser Tyr Trp Ser
        115                 120                 125

Pro Gly Leu Leu Val Thr Val Ser Ser Val Ser Gln His Pro Ser
    130                 135                 140

Ile Tyr Pro Leu Arg Thr Cys Cys Ile Lys Glu Thr Ser Val Ala Leu
145                 150                 155                 160

Gly Cys Leu Val Lys Asp Tyr Phe Pro Gly Ser Val Ala Val Thr Trp
                165                 170                 175

Asp Thr Ala Pro Leu Asp Gly Ser Thr Leu Thr Phe Pro Ser Ile Gln
            180                 185                 190

Met Ala Asn Ser Ser Leu Tyr Val Thr Ser Gln Leu Thr Val Ser
        195                 200                 205

Gly Glu Gln Pro Lys Gln Phe Thr Cys Ser Val Phe His Ala Glu Thr
    210                 215                 220

Asn Thr Thr Ala Met Lys Thr Val Ser Thr Glu Cys Ala Lys Asn Phe
225                 230                 235                 240

Ser Asp Pro Ser Val Arg Leu Phe Tyr Ser Ser Cys Asp Pro Ser Gly
                245                 250                 255
```

```
Asp Thr His Thr Thr Ile Gln Leu Leu Cys Arg Ile Ser Gly Tyr Thr
            260                 265                 270

Pro Gly Lys Ile Lys Val Thr Trp Leu Val Asp Gly His Glu Ser Lys
        275                 280                 285

Glu Leu Tyr Ala Gln Pro Gly Pro Glu Ile Gln Glu Gly Asn Leu Thr
    290                 295                 300

Thr Thr Tyr Ser Glu Val Asn Ile Thr Gln Gly Gln Trp Ala Ser Glu
305                 310                 315                 320

Lys Thr Tyr Thr Cys Arg Val Asn Tyr Gly Phe Asn Phe Asp Asn
                325                 330                 335

His Ala Arg Arg Cys Thr Ala Glu Ser Glu Pro Arg Gly Val Ser Thr
            340                 345                 350

Tyr Leu Ile Pro Pro Thr Pro Leu Glu Leu Tyr Val Asn Lys Ser Pro
        355                 360                 365

Lys Ile Thr Cys Leu Val Val Asp Leu Ala Ser Thr Asn Asn Leu Ser
    370                 375                 380

Leu Thr Trp Ser Arg Ala Asn Gly Lys Pro Val His Ala Asp Pro Leu
385                 390                 395                 400

Asp Ile Lys His Gln Phe Asn Gly Thr Ile Thr Val Thr Ser Thr Leu
                405                 410                 415

Pro Val Asn Val Ile Asp Trp Val Glu Gly Glu Thr Tyr Tyr Cys Lys
            420                 425                 430

Val Ser His Gly Asp Leu Pro Lys Asp Ile Gln Arg Ser Ile Ser Lys
        435                 440                 445

Asp Val Gly Lys Arg Val Ala Pro Lys Val Tyr Val Phe Trp Pro Asp
    450                 455                 460

Arg Lys Glu Leu Glu Asn Gln Glu Glu Leu Thr Leu Thr Cys Leu Ile
465                 470                 475                 480

Gln Lys Phe Phe Pro Lys Asp Ile Ser Val Arg Trp Leu Arg Asn Lys
                485                 490                 495

Glu Leu Met Arg Glu Gly Gln His Thr Thr Thr Gln Pro Asp Arg Ala
            500                 505                 510

Asp Asn Asn Ser Leu Ala Phe Phe Ala Tyr Ser Arg Leu Ala Val Pro
        515                 520                 525

Lys Ala Ser Trp Lys Met Asp Asp Glu Phe Thr Cys Gln Val Ile His
    530                 535                 540

Glu Ala Leu Pro Lys Thr Arg Thr Leu Glu Lys Ser Val Phe Ile Asn
545                 550                 555                 560

Ser Gly Lys
```

<210> SEQ ID NO 36
<211> LENGTH: 427
<212> TYPE: PRT
<213> ORGANISM: Brushtail opossum (Trichosurus vulpecula)

<400> SEQUENCE: 36

```
Thr Ser Thr Ala Pro Ser Val Phe Pro Leu Val Ser Gly Cys Asp Pro
1               5                   10                  15

Asn Phe Glu Ser Leu Ser Phe Leu Gly Cys Leu Val Ser Gly Tyr Phe
            20                  25                  30

Pro Glu Pro Val Thr Val Ser Trp Asn Pro Glu Val Leu Asp Gly Ile
        35                  40                  45

Ile Thr Thr Phe Pro Ala Ala Tyr Asp Ser Thr Ser Gly Leu Tyr Thr
    50                  55                  60
```

```
Thr Thr Ser Gln Leu Ala Ile Ser Asp Gly Ser Gln Glu Phe Thr
 65                  70                  75                  80

Cys Ser Val Asp His Leu Pro Thr Ser Thr Lys Ile Glu Lys His Val
                 85                  90                  95

Ser Thr Gly Pro Thr Lys Asn Gly Pro Val Ile Pro Thr Val Lys
            100                 105                 110

Leu Phe His Ser Ser Cys Asp Pro Arg Gly Asp Ala His Ser Thr Ile
            115                 120                 125

Gln Leu Leu Cys Leu Val Ser Gly Phe Ser Pro Ala Arg Val Lys Val
        130                 135                 140

Thr Trp Leu Val Asp Gly Gln Glu Ala Glu Asn Leu Phe Pro Tyr Thr
145                 150                 155                 160

Thr Arg Pro Lys Arg Glu Gly Ser Gln Thr Phe Ser Leu Gln Ser Glu
                165                 170                 175

Leu Asn Ile Thr Gln Gly Gln Trp Thr Ser Leu Lys Thr Tyr Thr Cys
            180                 185                 190

Gln Val Thr His Asn Gly Ser Ile Tyr Arg Asp Asn Ala Gln Lys Cys
        195                 200                 205

Ser Asp Thr Asp Pro Arg Gly Ile Ser Ala Tyr Leu Ser Pro Pro Ser
210                 215                 220

Ala Phe Asp Leu Tyr Val Ser Lys Ala Pro Val Leu Thr Cys Leu Val
225                 230                 235                 240

Val Asp Leu Ala Ser Ala Glu Asn Val Lys Val Ser Trp Thr Arg Glu
                245                 250                 255

Ser Gly Gly Thr Val Ser Pro Ser Ser Pro Val Val Lys Glu Gln Tyr
            260                 265                 270

Asn Gly Thr Val Thr Ile Thr Ser Thr Leu Pro Val Gln Thr Asp Asp
        275                 280                 285

Trp Val Glu Gly Glu Thr Tyr Thr Cys His Leu Glu His Pro Asp Leu
290                 295                 300

Pro Phe Pro Leu Ile Arg Thr Ile Ser Lys Ala Pro Gly Lys Arg Ile
305                 310                 315                 320

Ala Pro Glu Val Tyr Met Phe Pro Pro Ser Glu Glu Lys Gly Asn
                325                 330                 335

Thr Val Ser Leu Thr Cys Leu Ile Arg Ala Phe Tyr Pro Ala Asp Ile
            340                 345                 350

Thr Val Gln Trp Leu Arg Asp Asn Lys Asp His Thr Gly His His
        355                 360                 365

Thr Thr Thr Arg Pro His Lys Asp His Gly Pro Asp Pro Ser Phe Phe
370                 375                 380

Leu Tyr Ser Arg Met Val Val Asn Arg Ser His Trp Gln Glu Gly His
385                 390                 395                 400

Thr Phe Thr Cys Arg Val Val His Glu Ala Leu Pro Gly Thr Arg Thr
                405                 410                 415

Leu Asp Lys Ser Leu His Tyr Ser Thr Gly Asn
            420                 425

<210> SEQ ID NO 37
<211> LENGTH: 574
<212> TYPE: PRT
<213> ORGANISM: Human (Homo sapiens)

<400> SEQUENCE: 37

Met Asp Trp Thr Trp Ile Leu Phe Leu Val Ala Ala Ala Thr Arg Val
```

```
1               5                   10                  15
His Ser Gln Thr Gln Leu Val Gln Ser Gly Ala Glu Val Arg Lys Pro
                20                  25                  30
Gly Ala Ser Val Arg Val Ser Cys Lys Ala Ser Gly Tyr Thr Phe Ile
                35                  40                  45
Asp Ser Tyr Ile His Trp Ile Arg Gln Ala Pro Gly His Gly Leu Glu
                50                  55                  60
Trp Val Gly Trp Ile Asn Pro Asn Ser Gly Gly Thr Asn Tyr Ala Pro
65                              70                  75              80
Arg Phe Gln Gly Arg Val Thr Met Thr Arg Asp Ala Ser Phe Ser Thr
                85                  90                  95
Ala Tyr Met Asp Leu Arg Ser Leu Arg Ser Asp Asp Ser Ala Val Phe
                100                 105                 110
Tyr Cys Ala Lys Ser Asp Pro Phe Trp Ser Asp Tyr Tyr Asn Phe Asp
                115                 120                 125
Tyr Ser Tyr Thr Leu Asp Val Trp Gly Gln Gly Thr Thr Val Thr Val
                130                 135                 140
Ser Ser Ala Ser Thr Gln Ser Pro Ser Val Phe Pro Leu Thr Arg Cys
145                             150                 155             160
Cys Lys Asn Ile Pro Ser Asn Ala Thr Ser Val Thr Leu Gly Cys Leu
                165                 170                 175
Ala Thr Gly Tyr Phe Pro Glu Pro Val Met Val Thr Trp Asp Thr Gly
                180                 185                 190
Ser Leu Asn Gly Thr Thr Met Thr Leu Pro Ala Thr Thr Leu Thr Leu
                195                 200                 205
Ser Gly His Tyr Ala Thr Ile Ser Leu Leu Thr Val Ser Gly Ala Trp
210                             215                 220
Ala Lys Gln Met Phe Thr Cys Arg Val Ala His Thr Pro Ser Ser Thr
225                             230                 235             240
Asp Trp Val Asp Asn Lys Thr Phe Ser Val Cys Ser Arg Asp Phe Thr
                245                 250                 255
Pro Pro Thr Val Lys Ile Leu Gln Ser Ser Cys Asp Gly Gly Gly His
                260                 265                 270
Phe Pro Pro Thr Ile Gln Leu Leu Cys Leu Val Ser Gly Tyr Thr Pro
275                             280                 285
Gly Thr Ile Asn Ile Thr Trp Leu Glu Asp Gly Gln Val Met Asp Val
                290                 295                 300
Asp Leu Ser Thr Ala Ser Thr Thr Gln Glu Gly Glu Leu Ala Ser Thr
305                             310                 315             320
Gln Ser Glu Leu Thr Leu Ser Gln Lys His Trp Leu Ser Asp Arg Thr
                325                 330                 335
Tyr Thr Cys Gln Val Thr Tyr Gln Gly His Thr Phe Glu Asp Ser Thr
                340                 345                 350
Lys Lys Cys Ala Asp Ser Asn Pro Arg Gly Val Ser Ala Tyr Leu Ser
                355                 360                 365
Arg Pro Ser Pro Phe Asp Leu Phe Ile Arg Lys Ser Pro Thr Ile Thr
                370                 375                 380
Cys Leu Val Val Asp Leu Ala Pro Ser Lys Gly Thr Val Asn Leu Thr
385                             390                 395             400
Trp Ser Arg Ala Ser Gly Lys Pro Val Asn His Ser Thr Arg Lys Glu
                405                 410                 415
Glu Lys Gln Arg Asn Gly Thr Leu Thr Val Thr Ser Thr Leu Pro Val
                420                 425                 430
```

```
Gly Thr Arg Asp Trp Ile Glu Gly Glu Thr Tyr Gln Cys Arg Val Thr
            435                 440                 445

His Pro His Leu Pro Arg Ala Leu Met Arg Ser Thr Thr Lys Thr Ser
        450                 455                 460

Gly Pro Arg Ala Ala Pro Glu Val Tyr Ala Phe Ala Thr Pro Glu Trp
465                 470                 475                 480

Pro Gly Ser Arg Asp Lys Arg Thr Leu Ala Cys Leu Ile Gln Asn Phe
                485                 490                 495

Met Pro Glu Asp Ile Ser Val Gln Trp Leu His Asn Glu Val Gln Leu
            500                 505                 510

Pro Asp Ala Arg His Ser Thr Thr Gln Pro Arg Lys Thr Lys Gly Ser
        515                 520                 525

Gly Phe Phe Val Phe Ser Arg Leu Glu Val Thr Arg Ala Glu Trp Glu
530                 535                 540

Gln Lys Asp Glu Phe Ile Cys Arg Ala Val His Glu Ala Ala Ser Pro
545                 550                 555                 560

Ser Gln Thr Val Gln Arg Ala Val Ser Val Asn Pro Gly Lys
                565                 570

<210> SEQ ID NO 38
<211> LENGTH: 93
<212> TYPE: PRT
<213> ORGANISM: Human (Homo sapiens)

<400> SEQUENCE: 38

Gly Leu Ala Gly Gly Ser Ala Gln Ser Gln Arg Ala Pro Asp Arg Val
1               5                   10                  15

Leu Cys His Ser Gly Gln Gln Gln Gly Leu Pro Arg Ala Ala Gly Gly
            20                  25                  30

Ser Val Pro His Pro Arg Cys His Cys Gly Ala Gly Arg Ala Asp Trp
        35                  40                  45

Pro Gly Pro Pro Glu Leu Asp Val Cys Val Glu Glu Ala Glu Gly Glu
    50                  55                  60

Ala Pro Trp Thr Trp Thr Gly Leu Cys Ile Phe Ala Ala Leu Phe Leu
65                  70                  75                  80

Leu Ser Val Ser Tyr Ser Ala Ala Leu Thr Leu Leu Met
                85                  90

<210> SEQ ID NO 39
<211> LENGTH: 27
<212> TYPE: PRT
<213> ORGANISM: Human (Homo sapiens)

<400> SEQUENCE: 39

Val Gln Arg Phe Leu Ser Ala Thr Arg Gln Gly Arg Pro Gln Thr Ser
1               5                   10                  15

Leu Asp Tyr Thr Asn Val Leu Gln Pro His Ala
            20                  25

<210> SEQ ID NO 40
<211> LENGTH: 136
<212> TYPE: PRT
<213> ORGANISM: Human (Homo sapiens)

<400> SEQUENCE: 40

Gly Ala Ala Val Pro Leu Ser His Ala Ala Gly Glu Ala Pro Asp Leu
1               5                   10                  15
```

```
Pro Arg Leu His Gln Arg Pro Ala Pro Arg Leu Gly Arg Gly Pro
            20                  25                  30

Leu Thr Leu His Gln Ala Gln Leu Phe Leu Cys Gln Arg Leu Ser Leu
        35                  40                  45

Pro Arg Ala Ala Pro Cys Pro Gly Trp Glu Lys Gly Ser Arg Gln Glu
 50                  55                  60

Lys Gly Ala Gln Gly His Tyr Cys Gly Leu Met Ala Ser Glu Pro Glu
 65                  70                  75                  80

Pro Arg Gly Ala Gly Ser Ala Ala Arg Leu Gln Ala Pro Arg Glu Pro
                85                  90                  95

Pro Val Ala Gly Pro Thr Arg Lys Pro Cys Leu Ser Leu Gln Gln Ser
            100                 105                 110

His Arg Gly Gly Val Ala Ala Ser Arg Ser Glu Leu Ile Pro Gly Pro
            115                 120                 125

Trp Val Ser Gly Ser Leu Pro Phe
    130                 135

<210> SEQ ID NO 41
<211> LENGTH: 109
<212> TYPE: PRT
<213> ORGANISM: Human (Homo sapiens)

<400> SEQUENCE: 41

Pro Arg Ala Ala Pro Glu Val Tyr Ala Phe Ala Thr Pro Glu Trp Pro
 1               5                  10                  15

Gly Ser Arg Asp Lys Arg Thr Leu Ala Cys Leu Ile Gln Asn Phe Met
            20                  25                  30

Pro Glu Asp Ile Ser Val Gln Trp Leu His Asn Glu Val Gln Leu Pro
        35                  40                  45

Asp Ala Arg His Ser Thr Thr Gln Pro Arg Lys Thr Lys Gly Ser Gly
     50                  55                  60

Phe Phe Val Phe Ser Arg Leu Glu Val Thr Arg Ala Glu Trp Glu Gln
 65                  70                  75                  80

Lys Asp Glu Phe Ile Cys Arg Ala Val His Glu Ala Ala Ser Pro Ser
                85                  90                  95

Gln Thr Val Gln Arg Ala Val Ser Val Asn Pro Gly Lys
            100                 105

<210> SEQ ID NO 42
<211> LENGTH: 107
<212> TYPE: PRT
<213> ORGANISM: Human (Homo sapiens)

<400> SEQUENCE: 42

Pro Arg Ala Ala Pro Glu Val Tyr Ala Phe Ala Thr Pro Glu Trp Pro
 1               5                  10                  15

Gly Ser Arg Asp Lys Arg Thr Leu Ala Cys Leu Ile Gln Asn Phe Met
            20                  25                  30

Pro Glu Asp Ile Ser Val Gln Trp Leu His Asn Glu Val Gln Leu Pro
        35                  40                  45

Asp Ala Arg His Ser Thr Thr Gln Pro Arg Lys Thr Lys Gly Ser Gly
     50                  55                  60

Phe Phe Val Phe Ser Arg Leu Glu Val Thr Arg Ala Glu Trp Glu Gln
 65                  70                  75                  80

Lys Asp Glu Phe Ile Cys Arg Ala Val His Glu Ala Ala Ser Pro Ser
                85                  90                  95
```

```
Gln Thr Val Gln Arg Ala Val Ser Val Asn Pro
            100                 105
```

<210> SEQ ID NO 43
<211> LENGTH: 71
<212> TYPE: PRT
<213> ORGANISM: Human (Homo sapiens)

<400> SEQUENCE: 43

```
Pro Arg Ala Ala Pro Glu Val Tyr Ala Phe Ala Thr Pro Glu Trp Pro
1               5                   10                  15

Gly Ser Arg Asp Lys Arg Thr Leu Ala Cys Leu Ile Gln Asn Phe Met
            20                  25                  30

Pro Glu Asp Ile Ser Val Gln Trp Leu His Asn Glu Val Gln Leu Pro
        35                  40                  45

Asp Ala Arg His Ser Thr Thr Gln Pro Arg Lys Thr Lys Gly Ser Gly
    50                  55                  60

Phe Phe Val Phe Ser Arg Leu
65                  70
```

<210> SEQ ID NO 44
<211> LENGTH: 27
<212> TYPE: PRT
<213> ORGANISM: Human (Homo sapiens)

<400> SEQUENCE: 44

```
Gly Ser Ile Gln Leu Cys Ser Gly Glu Asp Trp Pro Asp Leu Leu Ser
1               5                   10                  15

Thr Val Ala Met Thr Pro Gly Ser Tyr Pro Gln
            20                  25
```

<210> SEQ ID NO 45
<211> LENGTH: 279
<212> TYPE: DNA
<213> ORGANISM: Human (Homo sapiens)

<400> SEQUENCE: 45

```
gggctggctg gcggctccgc gcagtcccag agggccccgg atagggtgct ctgccactcc      60
ggacagcagc agggactgcc gagagcagca ggaggctctg tcccccaccc ccgctgccac     120
tgtggagccg ggagggctga ctggccaggt cccccagagc tggacgtgtg cgtggaggag     180
gccgagggcg aggcgccgtg gacgtggacc ggcctctgca tcttcgccgc actcttcctg     240
ctcagcgtga gctacagcgc cgccctcacg ctcctcatg                            279
```

<210> SEQ ID NO 46
<211> LENGTH: 81
<212> TYPE: DNA
<213> ORGANISM: Human (Homo sapiens)

<400> SEQUENCE: 46

```
gtgcagcggt tcctctcagc cacgcggcag gggaggcccc agacctccct cgactacacc      60
aacgtcctcc agccccacgc c                                                81
```

<210> SEQ ID NO 47
<211> LENGTH: 408
<212> TYPE: DNA
<213> ORGANISM: Human (Homo sapiens)

<400> SEQUENCE: 47

```
ggtgcagcgg ttcctctcag ccacgcggca ggggaggccc cagacctccc tcgactacac      60
```

```
caacgtcctc cagccccacg cctaggccgc gggccactca cgctccacca ggcccagctt      120
tttctctgcc agcgcctgag cctccctcgg gctgcaccct gccctgggtg ggaaaaggga      180
agcagacaag aaaaggggc acaaggtcac tactgtgggc tgatggccag tgaacctgag       240
cccagagggg ccggctcagc cgcaaggtta caggcgccga gagaaccacc agtcgcaggc      300
cccacccgaa aaccgtgtct gtcccttcaa cagagtcatc gaggaggggt ggctgctagc      360
cgttctgagc tcatcccagg cccctgggtc tccgggtcac tcccattc                   408

<210> SEQ ID NO 48
<211> LENGTH: 327
<212> TYPE: DNA
<213> ORGANISM: Human (Homo sapiens)

<400> SEQUENCE: 48
ccgcgtgctg ccccggaagt ctatgcgttt gcgacgccgg agtggccggg gagccgggac       60
aagcgcaccc tcgcctgcct gatccagaac ttcatgcctg aggacatctc ggtgcagtgg      120
ctgcacaacg aggtgcagct cccggacgcc cggcacagca cgacgcagcc ccgcaagacc      180
aagggctccg gcttcttcgt cttcagccgc ctggaggtga ccagggccga atgggagcag      240
aaagatgagt tcatctgccg tgcagtccat gaggcagcga gcccctcaca gaccgtccag      300
cgagcggtgt ctgtaaatcc cggtaaa                                          327

<210> SEQ ID NO 49
<211> LENGTH: 321
<212> TYPE: DNA
<213> ORGANISM: Human (Homo sapiens)

<400> SEQUENCE: 49
ccgcgtgctg ccccggaagt ctatgcgttt gcgacgccgg agtggccggg gagccgggac       60
aagcgcaccc tcgcctgcct gatccagaac ttcatgcctg aggacatctc ggtgcagtgg      120
ctgcacaacg aggtgcagct cccggacgcc cggcacagca cgacgcagcc ccgcaagacc      180
aagggctccg gcttcttcgt cttcagccgc ctggaggtga ccagggccga atgggagcag      240
aaagatgagt tcatctgccg tgcagtccat gaggcagcga gcccctcaca gaccgtccag      300
cgagcggtgt ctgtaaatcc c                                                321

<210> SEQ ID NO 50
<211> LENGTH: 215
<212> TYPE: DNA
<213> ORGANISM: Human (Homo sapiens)

<400> SEQUENCE: 50
ccgcgtgctg ccccggaagt ctatgcgttt gcgacgccgg agtggccggg gagccgggac       60
aagcgcaccc tcgcctgcct gatccagaac ttcatgcctg aggacatctc ggtgcagtgg      120
ctgcacaacg aggtgcagct cccggacgcc cggcacagca cgacgcagcc ccgcaagacc      180
aagggctccg gcttcttcgt cttcagccgc ctgga                                 215

<210> SEQ ID NO 51
<211> LENGTH: 82
<212> TYPE: DNA
<213> ORGANISM: Human (Homo sapiens)

<400> SEQUENCE: 51
gggctccatc cagctgtgca gtggggagga ctggccagac cttctgtcca ctgttgcaat       60
```
gaccccagga agctaccccc aa                                              82

<210> SEQ ID NO 52
<211> LENGTH: 24
<212> TYPE: DNA
<213> ORGANISM: Artificial sequence
<220> FEATURE:
<223> OTHER INFORMATION: Synthetic construct

<400> SEQUENCE: 52
ttgtttgtct gccgtgatgt atac                                            24

<210> SEQ ID NO 53
<211> LENGTH: 39
<212> TYPE: DNA
<213> ORGANISM: Artificial sequence
<220> FEATURE:
<223> OTHER INFORMATION: Synthetic construct

<400> SEQUENCE: 53
tgaggtaccg cgcgcaagaa tggaatcaaa cgtaacttc                            39

<210> SEQ ID NO 54
<211> LENGTH: 37
<212> TYPE: DNA
<213> ORGANISM: Artificial sequence
<220> FEATURE:
<223> OTHER INFORMATION: Synthetic construct

<400> SEQUENCE: 54
tgatctagac tgcaggatgg attcgttcaa ctagcag                              37

<210> SEQ ID NO 55
<211> LENGTH: 37
<212> TYPE: DNA
<213> ORGANISM: Artificial sequence
<220> FEATURE:
<223> OTHER INFORMATION: Synthetic construct

<400> SEQUENCE: 55
tgatgatgat gatgatagag ctcatccatg ccatgtg                              37

<210> SEQ ID NO 56
<211> LENGTH: 39
<212> TYPE: DNA
<213> ORGANISM: Human (Homo sapiens)

<400> SEQUENCE: 56
cacggtcccc ttgctgggtg ccaggtccac caccagaca                            39

<210> SEQ ID NO 57
<211> LENGTH: 36
<212> TYPE: DNA
<213> ORGANISM: Human (Homo sapiens)
<220> FEATURE:
<221> NAME/KEY: misc_feature
<222> LOCATION: (3)..(3)
<223> OTHER INFORMATION: n can be any nucleotide
<220> FEATURE:
<221> NAME/KEY: misc_feature
<222> LOCATION: (13)..(13)
<223> OTHER INFORMATION: n can be any nucleotide

<400> SEQUENCE: 57
cgngacggtt aangtcgcat tgcgctgctt ctcctc                               36

```
<210> SEQ ID NO 58
<211> LENGTH: 36
<212> TYPE: DNA
<213> ORGANISM: Human (Homo sapiens)

<400> SEQUENCE: 58
ccgcatgagg gccctgggca ggtggggtg ggtcac                              36

<210> SEQ ID NO 59
<211> LENGTH: 30
<212> TYPE: DNA
<213> ORGANISM: Human (Homo sapiens)

<400> SEQUENCE: 59
ggcgctcacc cctctcgggt tggaatctgc                                    30

<210> SEQ ID NO 60
<211> LENGTH: 54
<212> TYPE: DNA
<213> ORGANISM: Human (Homo sapiens)

<400> SEQUENCE: 60
gccggagccc ttggtcttgc ggggctgcgt cgtgctgtgc cgggcgtccg ggag         54

<210> SEQ ID NO 61
<211> LENGTH: 30
<212> TYPE: DNA
<213> ORGANISM: Human (Homo sapiens)

<400> SEQUENCE: 61
gatgaactca tctttctgct cccattcggc                                    30
```

IMMUNOGLOBULIN E VACCINES AND METHODS OF USE THEREOF

The present application claims benefit of priority to the following application, which is incorporated by reference in its entirety herein: U.S. Provisional Patent Application No. 60/312,120, entitled "Molecular Constructs of IgE Vaccines for Allergic Asthma and IgE-Medicated Allergic Diseases, and Methods of Use Thereof", filed on Aug. 13, 2001.

TECHNICAL FIELD

The present invention relates generally to the field of immunology and allergy, and more specifically concerns compositions useful in the prophylaxis or therapy of immunoglobulin E-mediated disease conditions, and methods for their use.

BACKGROUND

Immunoglobulin E (IgE) plays a central role in atopic hypersensitivity conditions including allergic rhinitis, allergic asthma, food allergies, and contact allergies (atopic dermatitis) and non-atopic hypersensitivity conditions including anaphylaxis, urticaria, and hives (Galli and Lantz, 1999, Fundamental Immunology, ed. Paul, p. 1127). IgE is identified as the presumptive causative agent responsible for passive transfer of cutaneous reactivity to allergens. Serum levels of IgE were shown to correlate closely with cutaneous reactivity to common allergens, as well as with bronchial hyper-responsiveness (Sears et al., 1991, *N. Engl. J. Med.*, 325:1067). Syndromes of allergic rhinitis and asthma are attenuated when levels of circulating IgE are neutralized by antibodies (Chang, 2000, *Nature Biotech*, 18:157).

IgE-mediated allergic inflammation is believed to be initiated upon triggering of IgE-sensitized mast cells with allergens. Inflammatory mediators include antihistamine and leukotrienes. The most common therapeutic approach to allergic inflammation is to block target organs from inflammatory mediators secreted by mast cells, for example through the use of antihistamines, which are believed to block the binding of histamine to their H1 receptors on vascular endothelial cells and vascular, respiratory, and gastrointestinal smooth muscle cells. Antihistamines are particularly helpful in allergic rhinitis, ocular allergies, urticaria, and atopic dermatitis. Newly developed non-sedating antihistamines are popular. However, antihistamines have been minimally beneficial in allergic asthma, and have little ability to affect the expression of chronic allergic inflammation in the airways of these patients. Several different leukotriene receptor antagonists are now available, and these agents show promise in reducing the signs and symptoms of chronic allergic asthma. Although these agents are generally preferred to antihistamines in this clinical setting, they only partially attenuate clinical evidence of the disease (Boushey, 2001, *J. Allergy Clin. Immunol.*, 108:S77) probably due to the multiple entities of mast cell small molecules mediators as well as a host of cytokines such as interleukin 4 (IL-4), interleukin 5 (IL-5), and tumor necrosis factor alpha (TNF-alpha), and eotaxin and other chemokines secreted by mast cells (Willis-Karp, 1999, *Annu. Rev. Immunol.*, 17:255).

As an alternative to the complexity of blocking the pharmacological effects of mast cell mediators, there have been various approaches to competitively inhibit IgE binding to and sensitization of its type I high affinity Fc receptor (FceRI). FceRI receptor antagonists can be for example, a long piece of IgE polypeptide of 72 amino acids in length derived from constant region heavy chain domains of CH2 to CH3 (Helm et al., 1988, *Nature,* 331:180). Moreover, there have been reports that short synthetic peptides from five to sixteen amino acid sequences from the CH4 domain interfere with direct IgE sensitization to FceRI on mast cells (Stanworth et al., U.S. Pat. No. 5,955,076).

Immunotherapy by allergen desensitization aims to shift the immune system response from developing Th2-type helper T-lymphocytes to Th1 helper T-lymphocytes. The general paradigm is that interleukin-4, secreted by Th2, plays a central role in initiating and augmenting allergen-specific IgE production. Interleukin-4 in turn plays a key role in skewing dichotomous T-lymphocyte development into the Th2 subset, thus further augmenting IgE production. Th2 commitment, in turn is believed to lead to production of more IL-4 (Mosmann and Coffman, 1989, *Ann Rev. Immunol.*, 7:145). A source of endogenous IL-4 is also believed to be contributed by mast cells and basophils, by a unique subset of IL-4 secreting CD8+T-lymphocytes, and by NK1.1+CD4 T-lymphocytes. There have been numerous attempts to downregulate Th2 development by administering recombinant allergens to patients, but due to the multiple sources of IL-4 and the complex cytokine feedback circuits in dichotomous CD4 T-lymphocyte development, this approach tends to yield variable results (Kay and Lessof, 1992, *Clin. Exp. Allergy*, S3:1; Seymour et al., 1998, *J. Exp. Med.*, 187:721).

Another approach to down-regulate the levels of circulating IgE resides is the administering of an anti-IgE antibody, that is to say, passive immunization against IgE. One such anti-IgE antibody recognizes a mast cell IgE binding site and thus blocks IgE sensitization to mast cells (Chang, 2000, *Nature Biotech.*, 18:157). The partially humanized monoclonal antibody E25 (MAb-E25) (Chang, U.S. Pat. No. 5,428, 133) is currently in a Phase III clinical trial. Passive immunization against anti-IgE results in the scavenging of circulating IgE, but would not be expected to substantially inhibit IgE production in atopic patients. Additionally, it has been shown that circulating IgE-anti-IgE complexes accumulate to a level ten-fold higher in passively immunized patients than that prior to treatment. This result is probably due to the increase in half-life of circulating IgE from about 2 days (circulating free IgE) to about 14 days (IgE-anti-IgE complexes), possibly because the humanized IgG used as the passive vaccine protects IgE from degradation. One concern from this is that IgE dissociated from the IgE-anti-IgE complex may sensitize mast cells. Another disadvantage to this passive vaccine is that a high dose of 300-500 mg per patient is routine. Benefits of anti-IgE treatment appear transiently during the period of intensive treatment, and the patient's condition significantly worsens two to three days after cession of injection of MAb-E25. Moreover, since MAb-E25 is not completely humanized (about 5% mouse sequence remains), neutralizing antibodies may be produced upon a second or subsequent treatments, thus further diminishing the efficacy of this approach (Corne et al., 1997, *J. Clin. Inv.*, 99:879; Milgrom et al., 1999, *N. Engl. J. Med.*, 341:1966). Furthermore, the paratope-specificity of MAb-E25 carries the additional risk of inducing anti-MAb-E25 antibodies, that is to say, anti-idiotypic antibodies (Vogel et al., 2000, *J. Mol. Biol.*, 298:729; Jerne, 1993, *Scan. J. Immunol.*, 38:1) bearing an internal image that mimics the original conformation of the FceRI binding site. Being bivalent, such antibodies can potentially cross-link FceRI and induce mast cell degranulation even in the absence of circulating IgE.

A long-term solution for IgE-mediated allergic diseases is urgently needed. One approach is to actively immunize against IgE. Existing approaches have focussed on using an entire IgE heavy chain domain as the immunogen (Hellman et al., U.S. Pat. No. 5,653,980). Although conceptually attractive, these approaches may lead to severe or even life-threatening IgE-mediated anaphylaxis, since antibodies raised against multiple antigenic epitopes across intact or largely intact IgE domains may cause extensive IgE-mediated mast cells/basophil activation. The contact region between the IgE heavy chain CH2 and CH3 domains and the FceRI receptor spans 5600 Ångstrøm according to the recent crystallographic structure obtained for the complex (Garman et al., 2000, *Nature*, 406:259). The safety of using MAb-E25 resides in its blocking of the binding to FceRI.

It is believed that conformation-sensitive B-lymphocyte epitopes are poorly represented by their corresponding synthetic, non-conformationally restricted peptides, even when these are coupled to a foreign carrier protein. There is at present no method for identifying and constructing IgE B-lymphocyte vaccines that correspond to constrained epitope such as those at mast cell binding sites. There is thus a great deal of unmet medical need to design other innovative means to reduce levels of IgE production.

In contrast, major histocompatibility class I (MHC class I)-restricted cytotoxic T-lymphocyte (CTL) epitopes are believed to be sequence-dependent. The present invention aims at developing a method of active immunization against IgE, using as immunogen a short stretch of sequence universally present on the IgE heavy chain constant region, independent of any conformation requirement.

BRIEF DESCRIPTION OF THE FIGURES

FIG. 3A: Effector cells were cytotoxic T-lymphocytes obtained from BALB/c mice (expressing murine MHC-I haplotype H-$2^d$) immunized with one of the test peptides p1 or p2, together with the co-stimulatory factor ovalbumin peptide (OVAp), in N-[1-(-2,3-dioleoyloxy)propyl]-N,N,N-trimethylammonium methylsulfate (DOTAP) liposomes. Target cells were P815 murine mastocytoma cells (expressing murine MHC-I haplotype H-$2^d$) pre-incubated with the appropriate test peptide (p1 or p2) and interferon-gamma. These results show that both IgE-derived test peptides p1 and p2, delivered with a co-stimulatory peptide and with liposomes, were able to elicit a CTL response in BALB/c mice that was cytotoxic to target cells displaying the peptides. FIG. 3B: Effector cells were cytotoxic T-lymphocytes obtained from BALB/c mice immunized with test peptide p3, with or without OVAp, in the presence or absence of DOTAP liposomes. Target cells were P815 murine mastocytoma cells that had been contacted with the test peptide p3 and interferon-gamma. These results show that immunization with p3 in the presence of the co-stimulatory peptide OVAp was able to induce a CTL response in BALB/c mice that was cytotoxic to the p3-treated P815 target cells; this CTL response was augmented by delivery of the peptides in liposomes. Immunization with the test peptide p3 alone, or with the co-stimulatory peptide OVAp in liposomes, did not induce a substantial CTL-response in BALB/c mice against the target cells; delivery of p3 in liposomes also amplified the CTL response relative to that seen with p3 alone.

FIG. 4 depicts the aligned amino acid sequences and sequence identification numbers for the test peptides p1, p2, p3, and p4. Underlined in the sequence of test peptide p3 are the two residues between which the serine endoproteinase Glu-C cleaves (marked by an arrow).

FIG. 6A: Target cells were P815 murine mastocytoma cells (murine MHC-I haplotype H$2^d$) that had been contacted with the test peptide p3 and treated overnight with 50 units per milliliter interferon-gamma. FIG. 6B: Target cells were IgE-secreting 26.82 hybridomas, which endogenously synthesize and naturally process and present murine immunoglobulin E peptides associated with the major histocompatibility complex class I molecule H-$2^d$. These results demonstrate that the test peptide p3 served as an immunogenic peptide when presented by antigen-presenting cells (dendritic cells that recognize p3) and were able to elicit in the DC-immunized mice a CTL response to naturally processed and presented IgE peptides. Dendritic cells incubated with p3 and OVAp were sufficient for inducing this CTL response. The magnitude of this CTL response was not amplified by either: (a) in vivo treatment of the DC-immunized mice with the anti-CD40 antibody FGK-45, or (b) incubation of the dendritic cells with p3 and OVAp with DOTAP liposomes.

An IgE peptide-specific CTL response was observed in 129/SvEv, IgE−/− mice immunized with p3 with OVAp in liposomes, or with DC treated with p3 and OVAp. Cytotoxic T-lymphocytes from these IgE−/− mice were able to lyse target cells that naturally processed and presented IgE peptides bound to H-2$^b$, regardless of whether the IgE peptides were biosynthesized endogenously (as in the B4 hybridoma cells, FIG. 7A) or were introduced exogenously (as in the EL-4 lymphoma cells, FIG. 7B).

Figure 7:
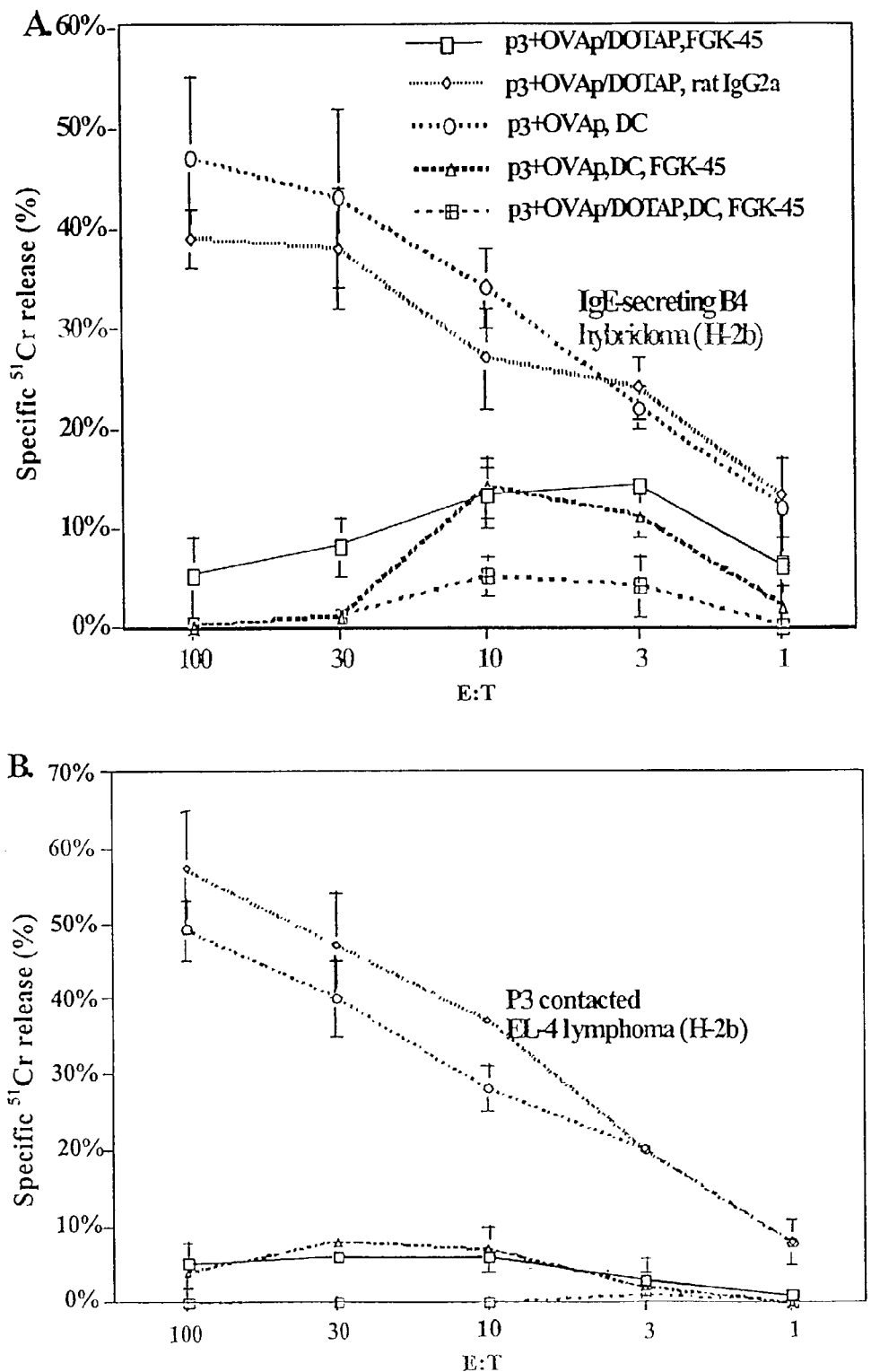
FIG. 7 depicts results of a standard chromium release assay using effector (E) cells at the indicated ratios to target (T) cells. Values shown are means of triplicate cultures with error bars indicating the standard deviation. Effector cells were cytotoxic T-lymphocytes obtained from 129/SvEv mice (murine MHC-I haplotype H2$^b$) that either carried the wild-type IgE gene (IgE+/+) (FIG. 7C and FIG. 7D), or that were defective in the IgE gene (IgE−/−) (FIG. 7A and FIG. 7B). The mice were immunized as indicated with the test peptide p3 in the presence of OVAp, and then treated in vivo with the anti-CD40 antibody FGK-45 or with rat IgG2a, or were immunized with dendritic cells (treated with p3 and OVAp in the presence or absence of DOTAP liposomes), and then treated or not in vivo with the anti-CD40 antibody FGK-45. Target cells were murine immunoglobulin E-secreting B4 hybridoma cells (murine MHC-I haplotype H-2$^b$) (FIG. 7A and FIG. 7C), or murine EL-4 lymphoma cells (murine MHC-I haplotype H-2$^b$), which had been contacted with the test peptide p3 and treated with interferon-gamma (FIG. 7B), or 26.82 hybridomas (which produce endogenous murine IgE associated with the murine MHC-I haplotype H-2$^d$) (FIG. 7D).

A similar IgE peptide-specific CTL response was observed in 129/SvEv, IgE+/+mice immunized with p3 with OVAp in liposomes, or with DC treated with p3 and OVAp. This CTL response was also specific for IgE peptides bound to a specific MHC-I haplotype as the CTL were able to lyse B4 hybridoma cells (H-2$^b$ haplotype) (FIG. 7C) but not 26.82 hybridoma cells (H-2$^d$ haplotype) (FIG. 7D). These results show that: a) MHC-I-restriction of the CTL response is observed at both the inductive phase and effector phase, b) immunization methods using different modes of co-stimulation were sufficient to overcome tolerance to self-IgE peptides in the IgE+/+ mice, c) IgE test peptides, processed and presented by DC, are at least similar to endogenously produced, naturally processed and presented IgE peptides that are bound to MHC-I of IgE-secreting plasma cell, and d) the CTL response induced by DC immunization was not amplified by treatment with anti-CD40 antibody.

Figure 8:
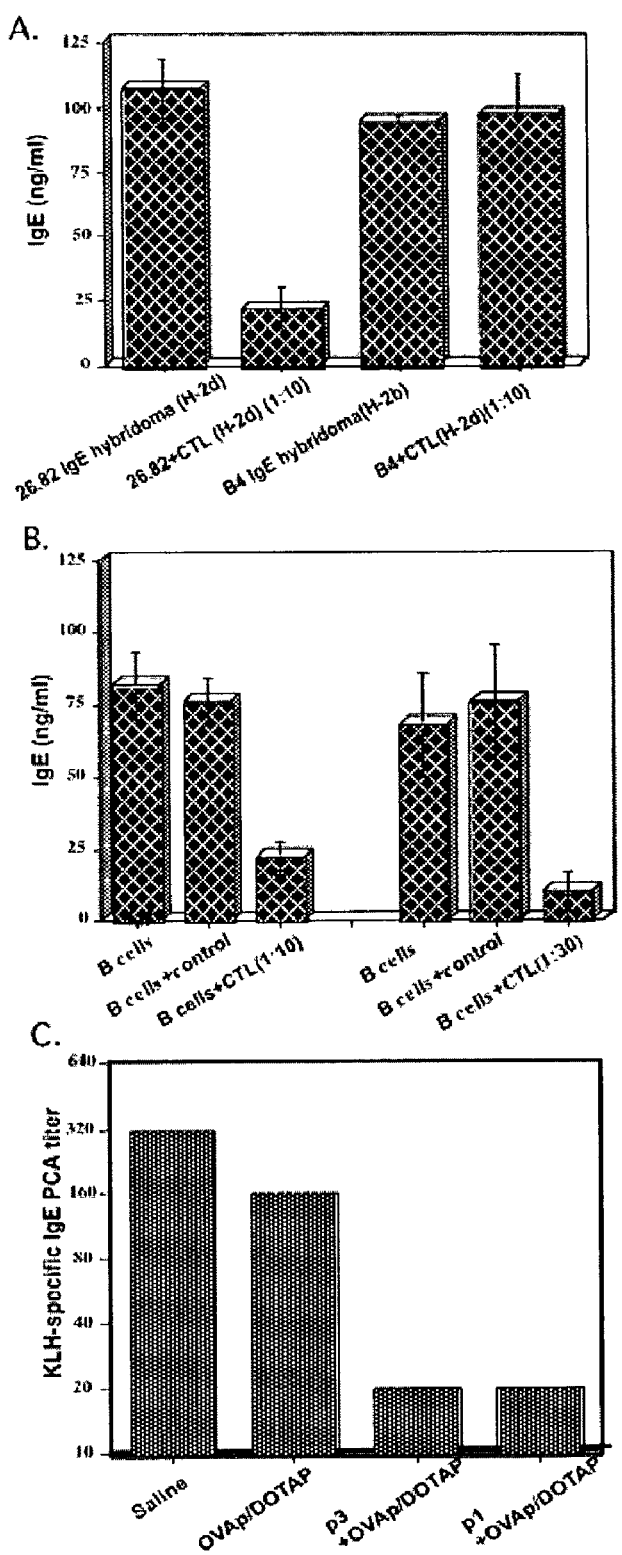

FIG. 8 depicts the inhibition of immunoglobulin E production in vitro and in vivo by immunoglobulin E-specific cytotoxic T-lymphocytes. FIG. 8A and FIG. 8B depict results of a commercial double-sandwich ELISA assay for immunoglobulin E. In FIG. 8A, cytotoxic T-lymphocytes (at an effector-to-target cell ratio of 10 to 1) elicited by p3 immunization of H-2$^d$ haplotypic mice decreased IgE production by H-2$^d$ haplotypic IgE-secreting cells (26.82 hybridoma cells) but did not appreciably decrease IgE production by H-2$^b$ haplotypic IgE-secreting cells (B4 hybridoma cells). These results show the MHC-I molecule specificity of the CTL response induced by a single test peptide. In FIG. 8B, cytotoxic T-lymphocytes from the p3-immunized mice markedly inhibited IgE production by LPS and IL-4 stimulated B-lymphocyte cultures in vitro at effector-to-target cell ratios of 1:10 or 1:30, whereas cytotoxic T-lymphocytes obtained from the mice immunized with only OVAp as a control did not decrease IgE production. These results show the test peptide-induced CTL response can inhibit IgE production by cells that produce IgE in situ. FIG. 8C depicts results of passive cutaneous anaphylaxis (PCA) measurements in BALB/c mice that had been immunized with p3 or p1 with OVAp in DOTAP liposomes, or with only OVAp in DOTAP liposomes, or with only saline. The mice were subsequently challenged with keyhole limpet hemocyanin (KLH), and the allergen-specific (KLH-specific) IgE in pooled blood was then determined by PCA titres. These results show that immunization with a test peptide, together with appropriate modes of co-stimulation, can substantially decrease allergen-induced IgE production in vivo.

Figure 9:
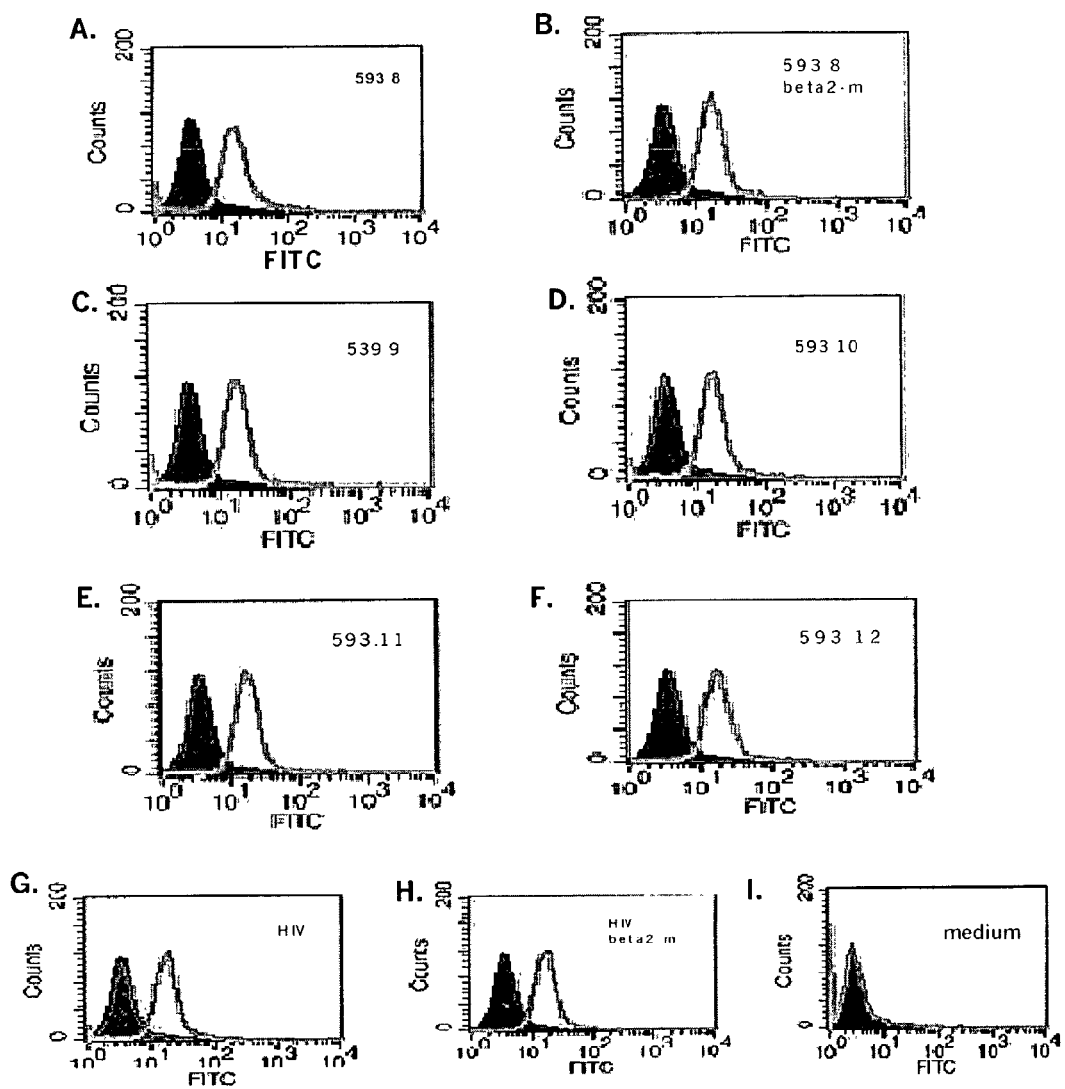

FIG. 9 depicts results of fluorescence-activated cell sorting (FACS) experiments. Five test peptides (peptide numbers 539.11, 539.12, 539.8, 539.9, and 539.10, representing three of the four CH domains of human IgE) from the panel of 12 high-, moderate-, and low-affinity test peptides shown in Table I were tested in RMA-S-A2.1 cells (murine TAP-deficient RMA-S cells that express HLA-A2.1). A nonameric peptide derived from the human immunodeficiency virus (HIV), was tested as an example of a nonameric HLA-A2.1-specific peptide that is not derived from human IgE. RMA-S-A2.1 cells were incubated with the individual test peptides, in the presence or absence of human beta-2 microglobulin. Cells were incubated with fluorescein isothiocyanate (FITC)-labelled anti-HLA-A2.1 antibody. FACS analysis was performed on a FACScan, with about ten thousand events collected and analyzed. Increase of HLA-A2.1-specific fluorescence intensity by one log was observed in cultures incubated with any of the five human IgE test peptides tested (test peptides number 539.8, 539.9, 539.10, 539.11, and 539.12, shown respectively in FIG. 9A, FIG. 9C, FIG. 9D, FIG. 9E, and FIG. 9F). In contrast, no appreciable increase of HLA-A2.1-specific fluorescence intensity was detected in cultures incubated with medium alone (FIG. 9I). These results show that the five IgE test peptides were able to phenotypically correct defective MHC-I molecule expression in RMA-S-A2.1 cells. The increase of HLA-A2.1-specific fluorescence intensity is comparable among the five IgE test peptides, and between the five IgE test peptides and the HIV control peptide (HIV) (FIG. 9G). These results show that different CH domains of human IgE can provide a plurality of therapeutic targets for IgE-specific cytotoxic T-lymphocytes. The addition of exogenous human beta-2 microglobulin ("beta2-m") did not substantially enhance surface expression of HLA-A2.1 (FIG. 9A versus FIG. 9B; FIG. 9G versus FIG. 9H), showing that these IgE peptides, which were predicted to bind strongly to HLA-A2.1, induced a high or possibly maximal expression of HLA-A2.1 at the cell surface.

Figure 10:
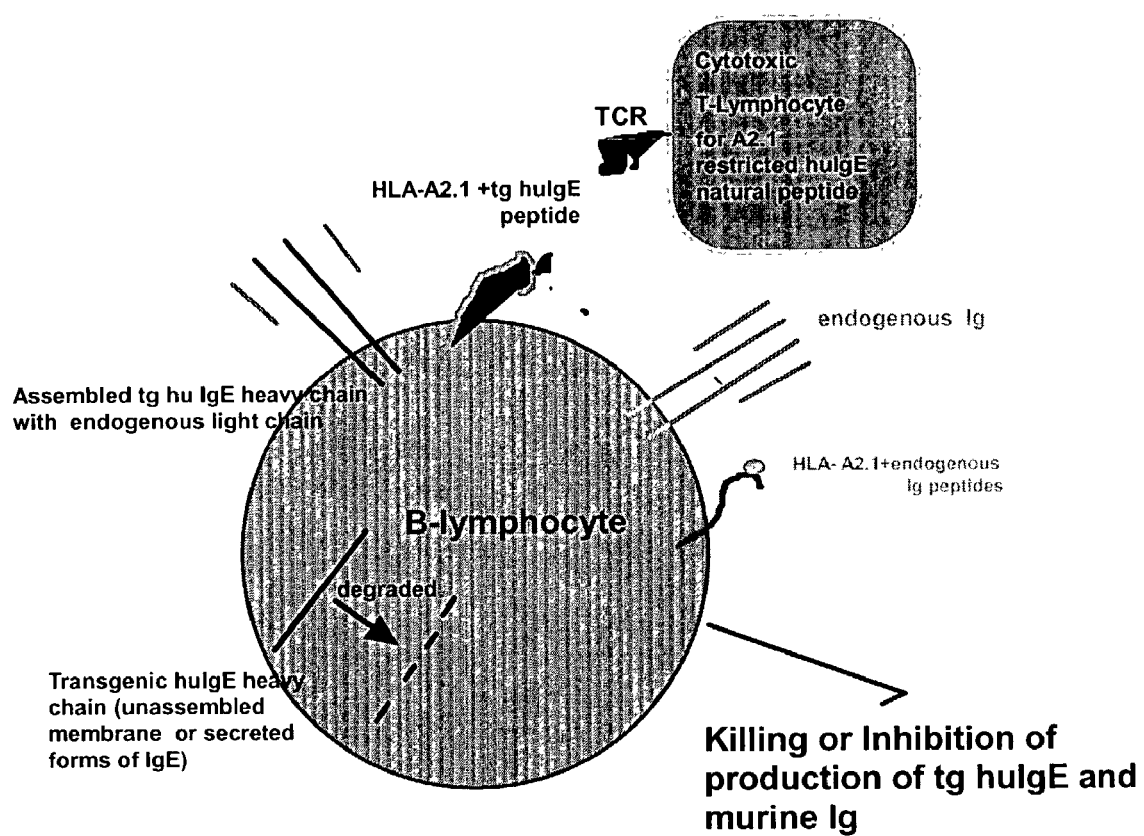

FIG. 10 schematically depicts a B-lymphocyte from mice that are transgenic for a human MHC-I molecule and for human immunoglobulin E. Mice were engineered to transgenically express both human HLA-A2.1 and human immunoglobulin E (tg huIgE) (heavy chain constant region and membrane domain, fused into the murine VH gene). The resulting animals express human HLA-A2.1 at the cell surface, and produce the chimeric human/murine immunoglobulin E (comprising human IgE heavy chain and the endogenous murine IgE light chain) as well as the endogenous murine IgE.

Figure 11:
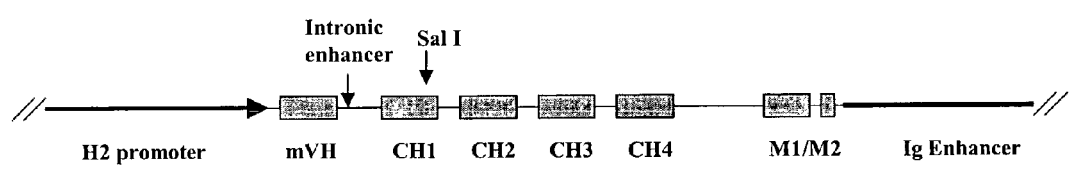

FIG. 11 schematically depicts construction of an antigen-specific, mouse/human chimeric immunoglobulin gene. The murine IgE VH segment (mVH) was ligated via the SalI restriction site near the beginning of the human IgE CH1 domain, followed by the remainder of the IgE heavy chain constant region domains (CH2, CH3, and CH4) and the membrane domains (M1 and M2). The resulting chimeric construct was cloned into the modified pUC19 vector, pHSE3', which contains the MHC-I H-2 promoter and immunoglobulin heavy chain enhancer region.

FIG. 12A depicts the different human immunoglobulin E isoforms cDNA amplified by reverse transcriptase-polymerase chain reaction from total RNA isolated from U266 cells (lane 2), and cloned into pGEM vectors (lanes 3-7 and 10). Three IgE isoforms are predominantly assembled by U266 cells: the classical membrane long isoform (lane 3), the membrane short isoform (lanes 4, 5, and 7), and the membrane long isoform (lane 6). In addition, the main IgE isoform secreted by U266 cells was amplified by RT-PCR (lane 9) and cloned into pGEM (lane 10). FIG. 12B depicts the adenoviral IgE construct consisting of the adenoviral vector pAd-lacZ, into which was cloned the full-length cDNA of human IgE membrane long form (pAd-IgEml).

Figure 13:
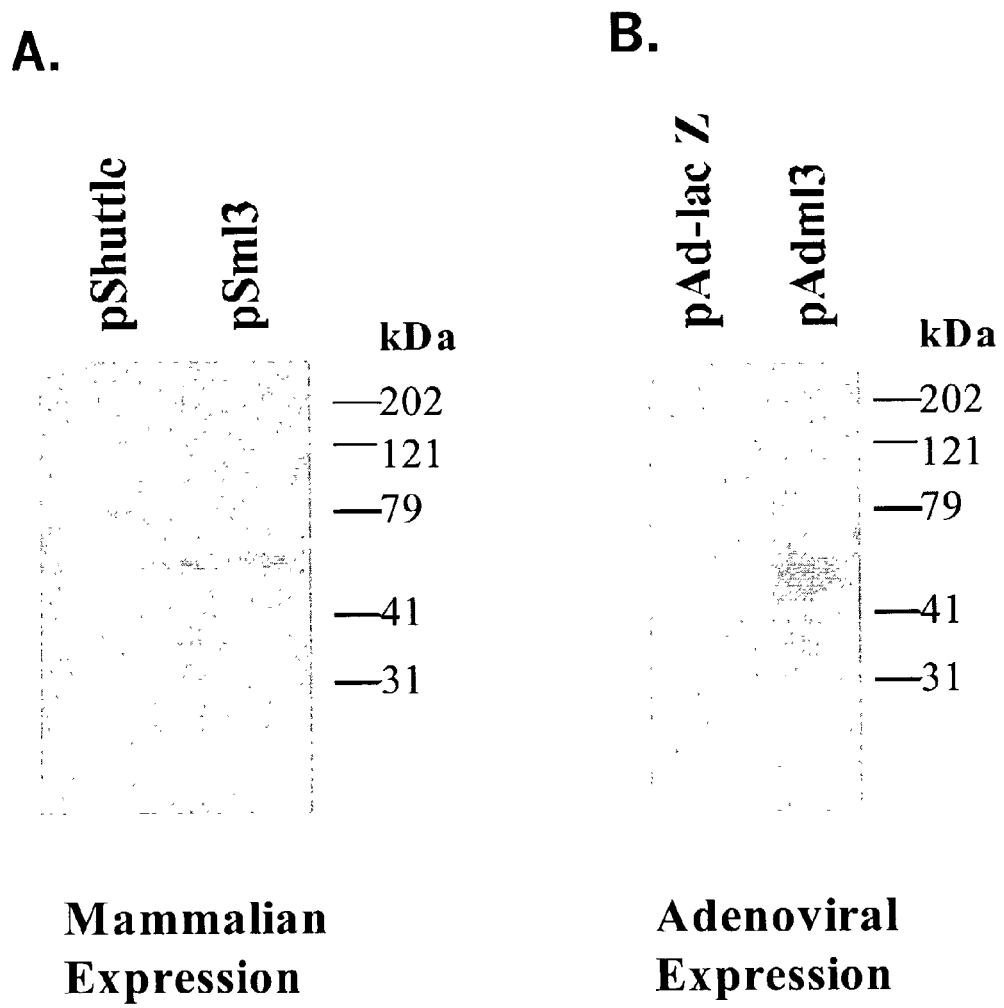

FIG. 13 depicts results of a Western blot using goat anti-human IgE IgG as the primary antibody, rabbit anti-goat IgG antibody, conjugated with horseradish peroxidase (HRP) as the secondary antibody, and 3,3',5,5'-tetramethylbenzidine as a substrate. The full-length cDNA of human IgE membrane long form was cloned into the mammalian expression vector pShuttle and the resulting construct used to transfect human kidney 293 cells. Transient expression of the pSm13 insert (pSm13) with full membrane-encoded exon sequences was confirmed by the presence of an immunoreactive protein transcript with the predicted molecular weight of about 65 kDa, which was absent in the null vector (pShuttle) (FIG. 13A). The adenoviral IgE construct pAd-IgEml, which also contained the full-length cDNA of human IgE membrane long form, was amplified and subjected to SDS-PAGE and Western blot. The heavy chain gene product expressed using pAd-IgEml appeared as the same molecular weight but migrated as a broader band, which was absent in the null vector (pAd-lacZ) (FIG. 13B).

Figure 14:
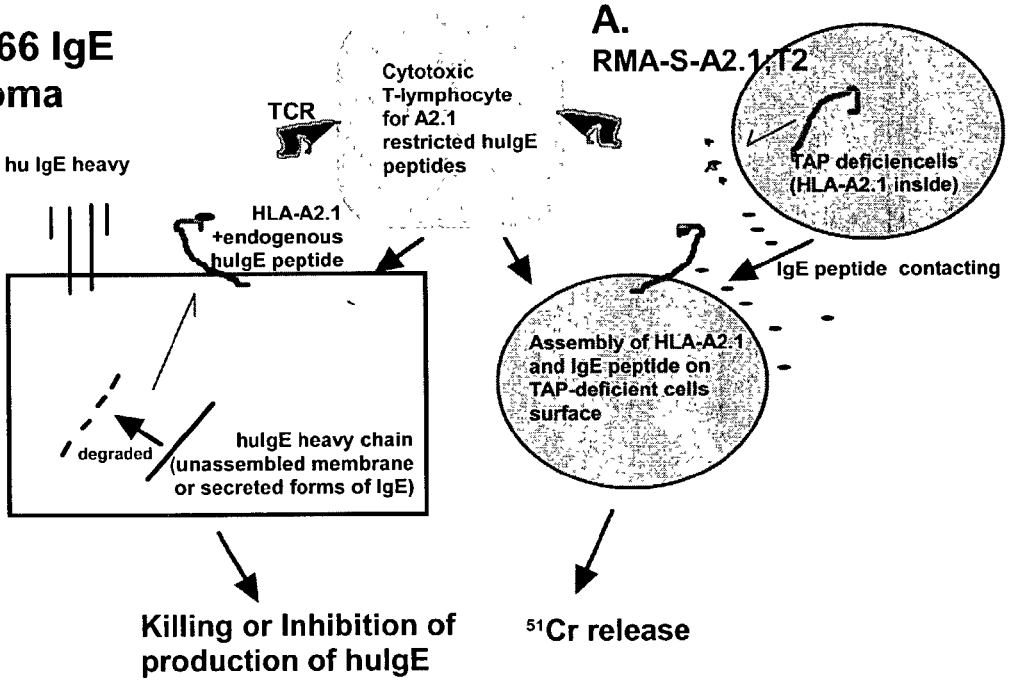
Figure 15C:
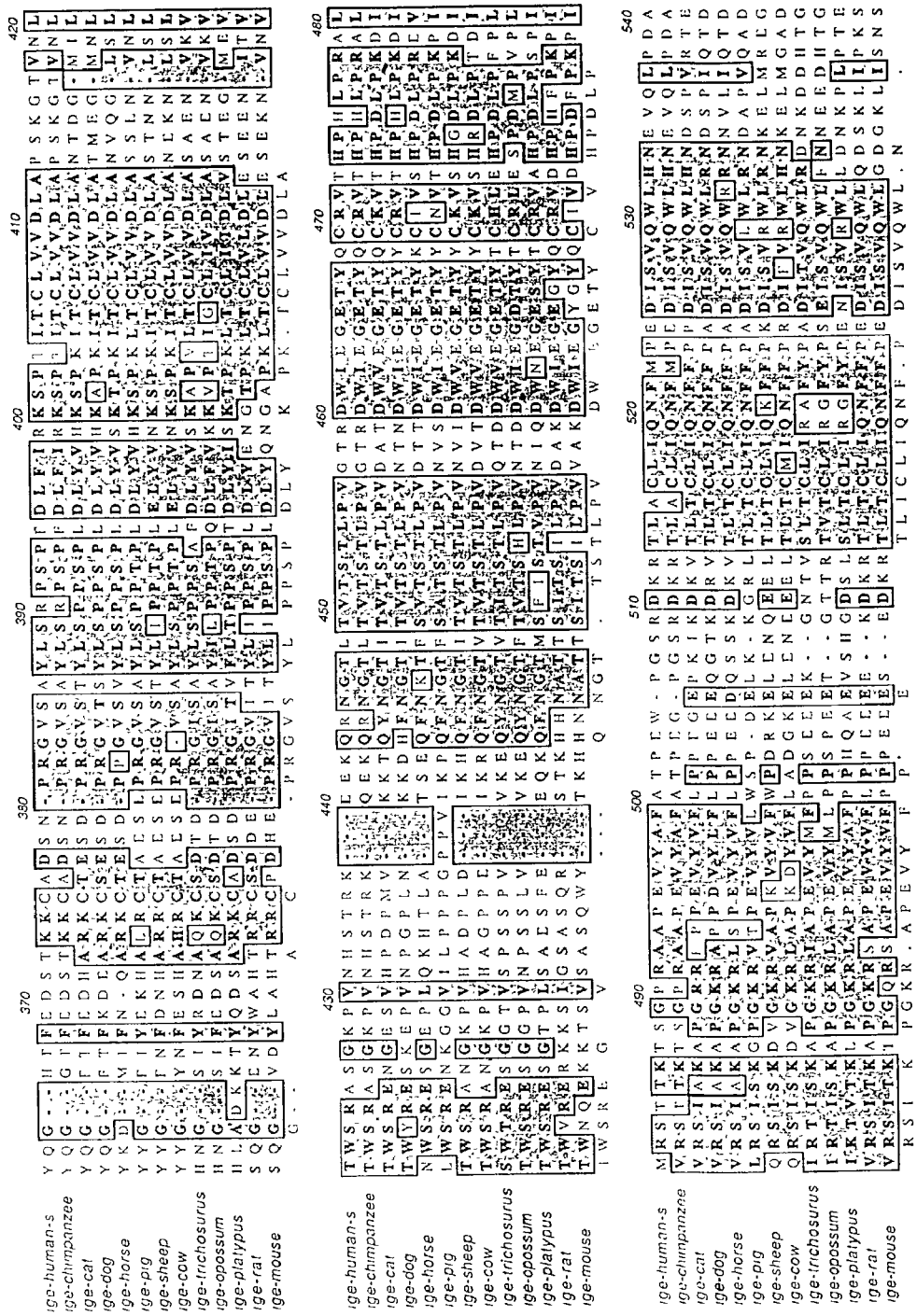
Figure 15D:
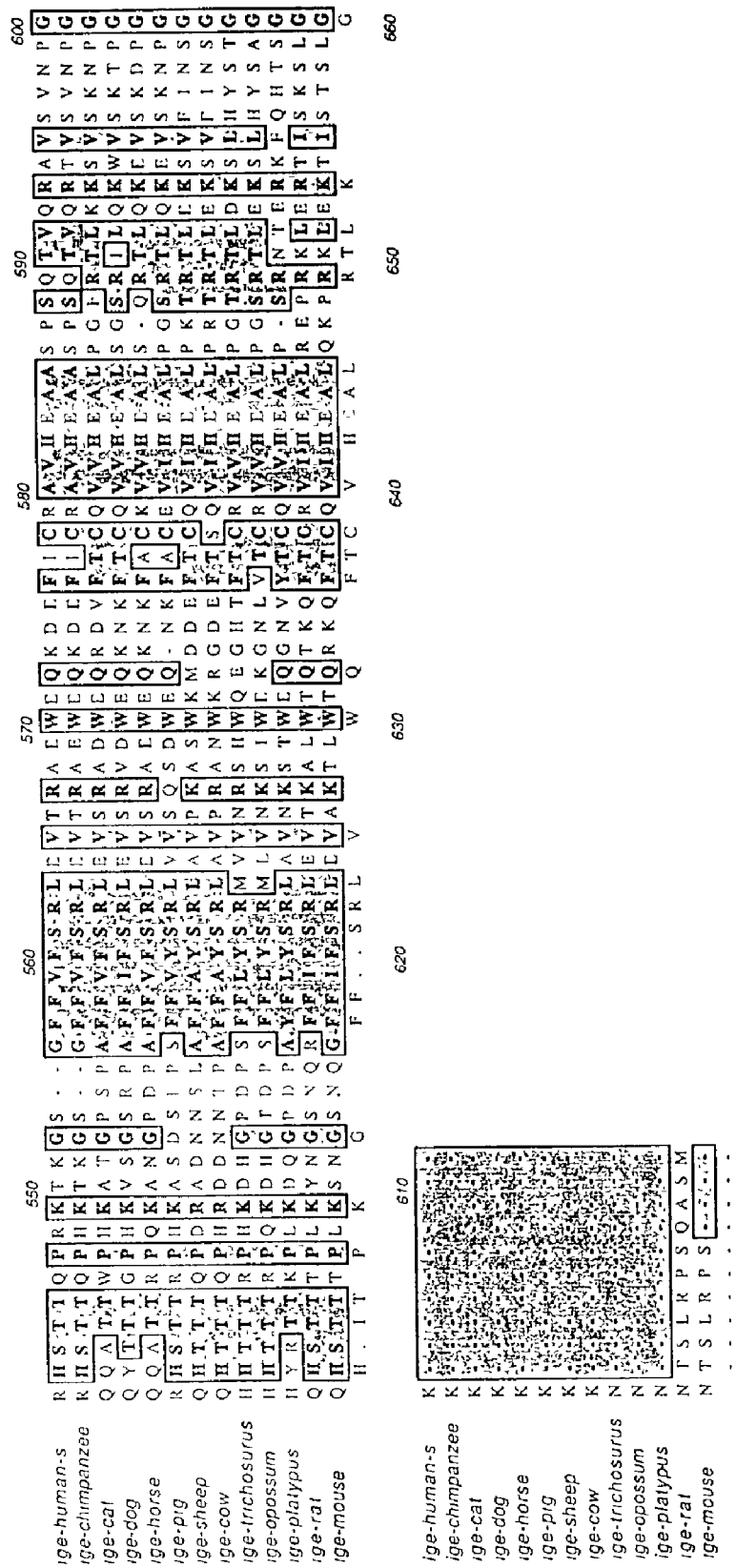

FIG. 14 depicts two approaches to testing cytotoxic T-lymphocytes, from transgenic mice that express HLA-A2.1 and that have been immunized (for example, with a selected immunogenic IgE peptide), for the ability to lyse IgE producing cells and to inhibit IgE production. The two approaches use different target cell types. In the first approach (depicted in FIG. 14A), the target cells are cells in which the MHC-I molecule is contacted with test peptide exogenously. As shown in FIG. 14A, a specific example of such target cells are TAP-deficient RMA-S cells transgenically expressing HLA-A2.1. Another example of such target cells are the human cells T2. The target cells are contacted (pulsed) with IgE peptides that bind to and induce cell-surface expression of HLA-A2.1, allowing the cytotoxic T-lymphocytes to recognize and lyse these target cells. In the second approach (depicted in FIG. 14B), the target cells are cells in which the MHC-I molecule presents endogenously produced IgE peptides. As shown in FIG. 14B, a specific example of such target cells are human U266 IgE myeloma cells, which have the HLA-A2.1 haplotype.

Figure 15A:
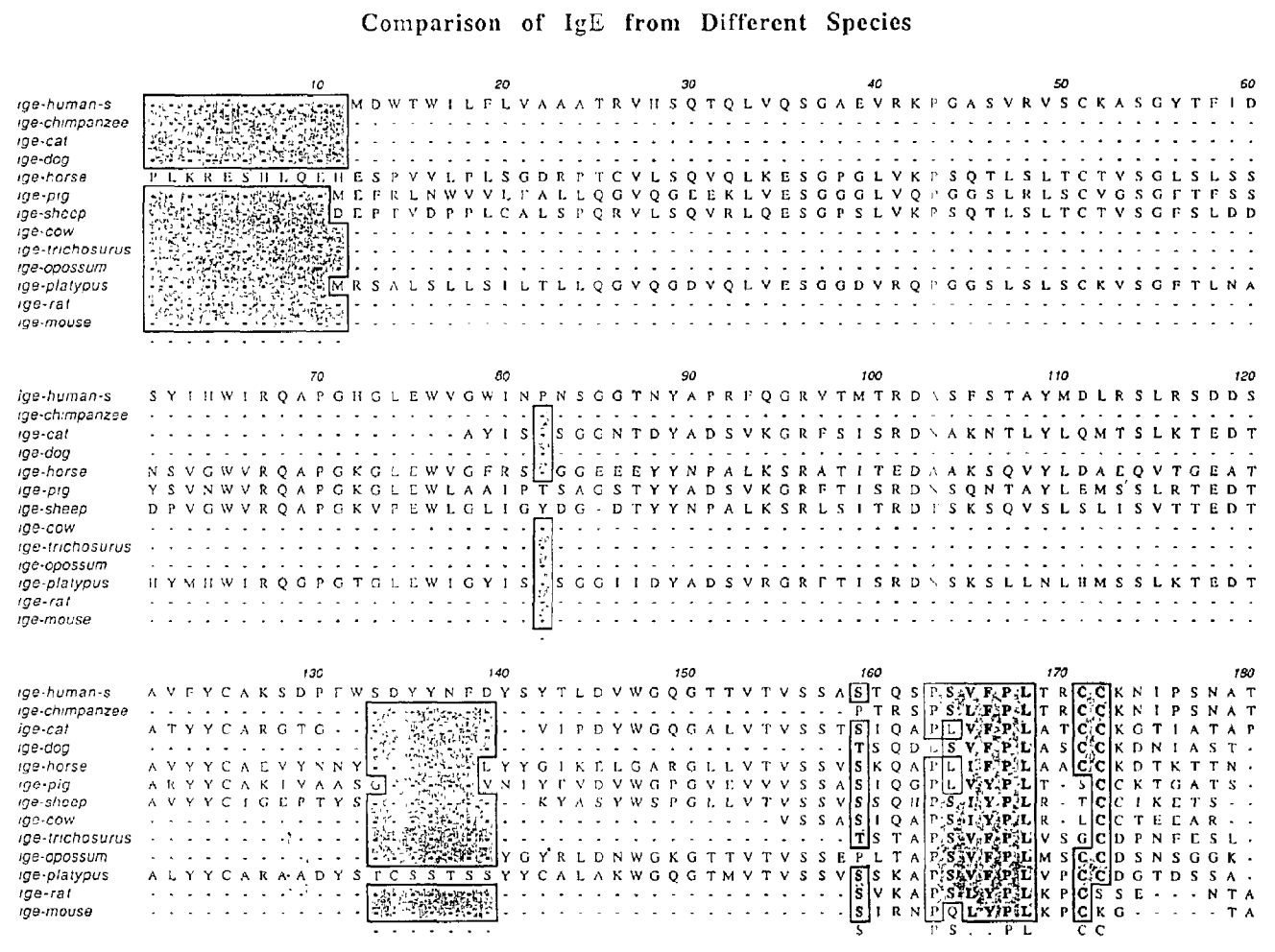
Figure 15B:
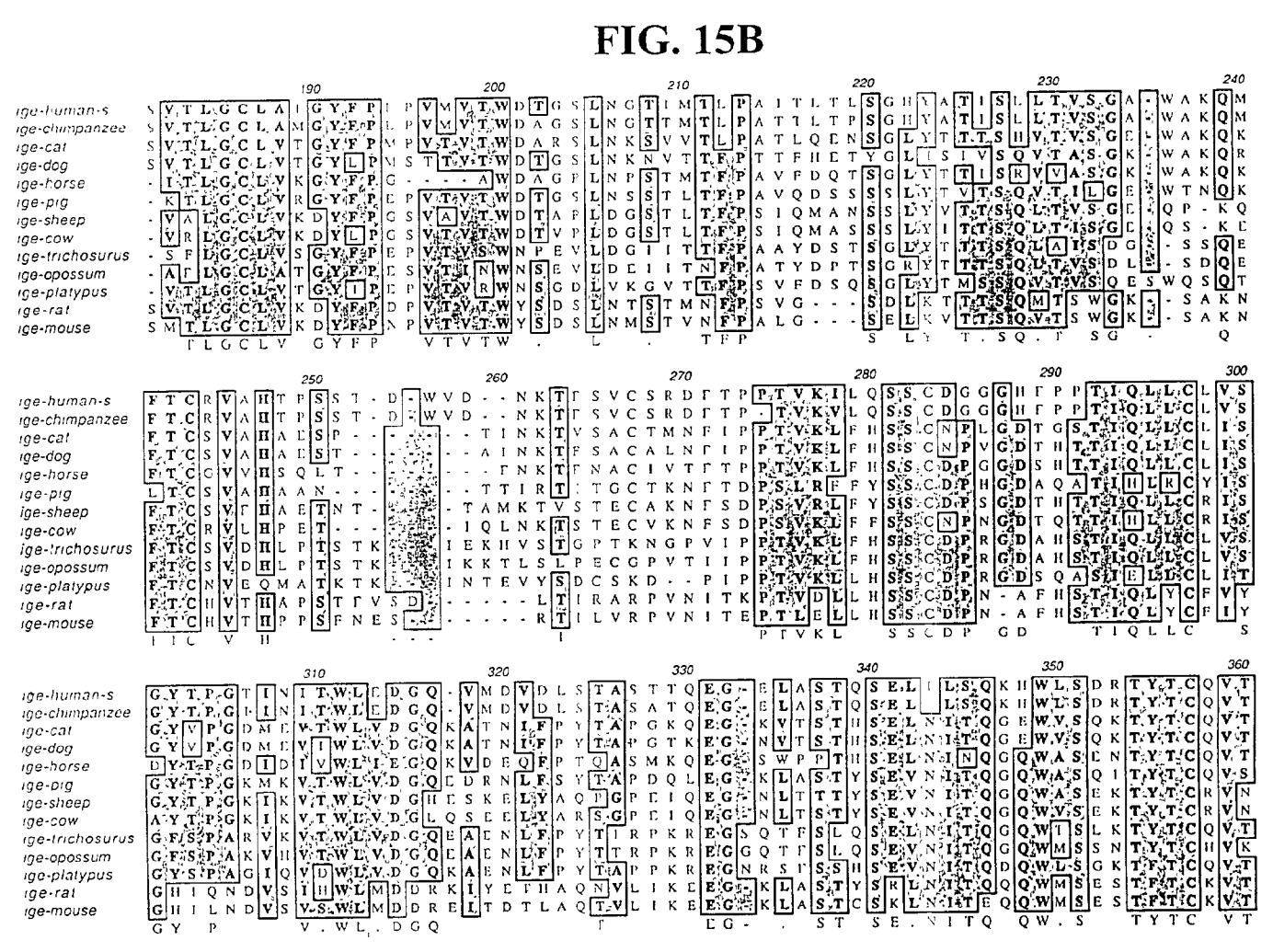

FIG. 15A, FIG. 15B, FIG. 15C, and FIG. 15D depict alignment of the immunoglobulin E heavy chain (including complete CH1 to CH4 constant region domains) amino acid sequences for human, sheep, rat, pig, mouse, horse, duck, dog, cow, chimpanzee, and cat. Shaded regions indicate regions of sequence homology.

Figure 16:
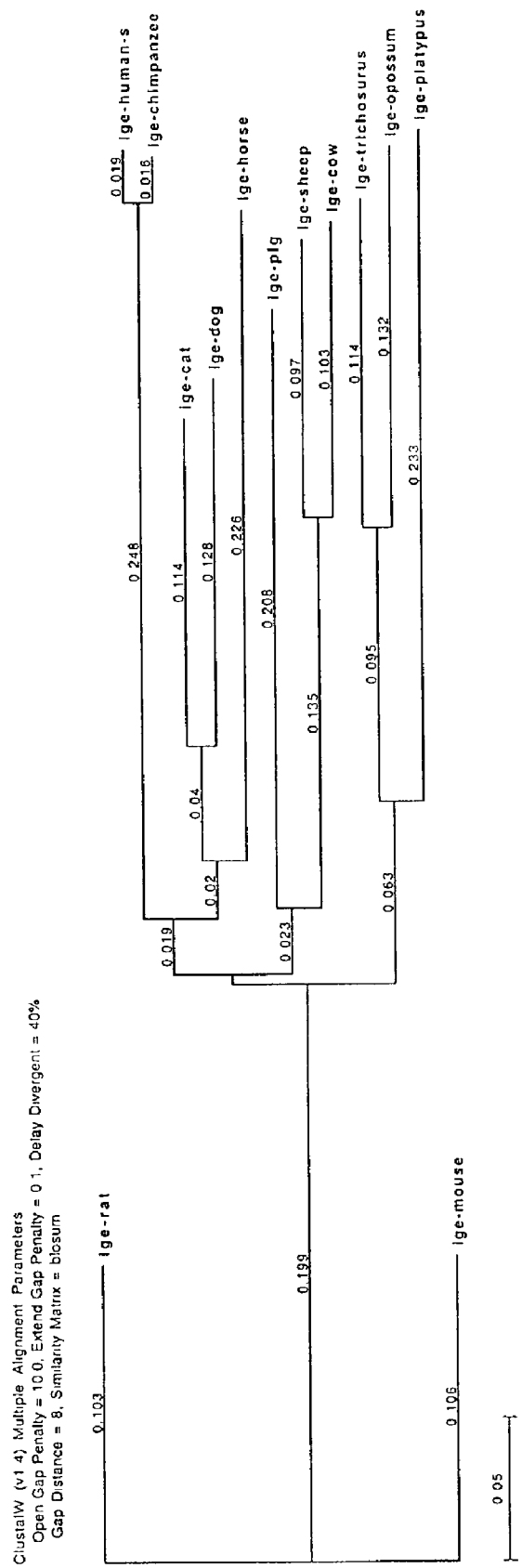

FIG. 16 depicts a phylogenetic tree representing the inferred evolutionary divergence between the immunoglobulin E heavy chain polypeptides of human, sheep, rat, pig, mouse, horse, duckbilled platypus, dog, cow, chimpanzee, Trichosurus (brushtail possum), and cat, calculated using the progressive multiple sequence alignment program ClustalW and using the alignment parameters given. The numerical value on top of each line indicates the evolutionary distance for that respective species from the most recent common ancestor of IgE.

Figure 17:
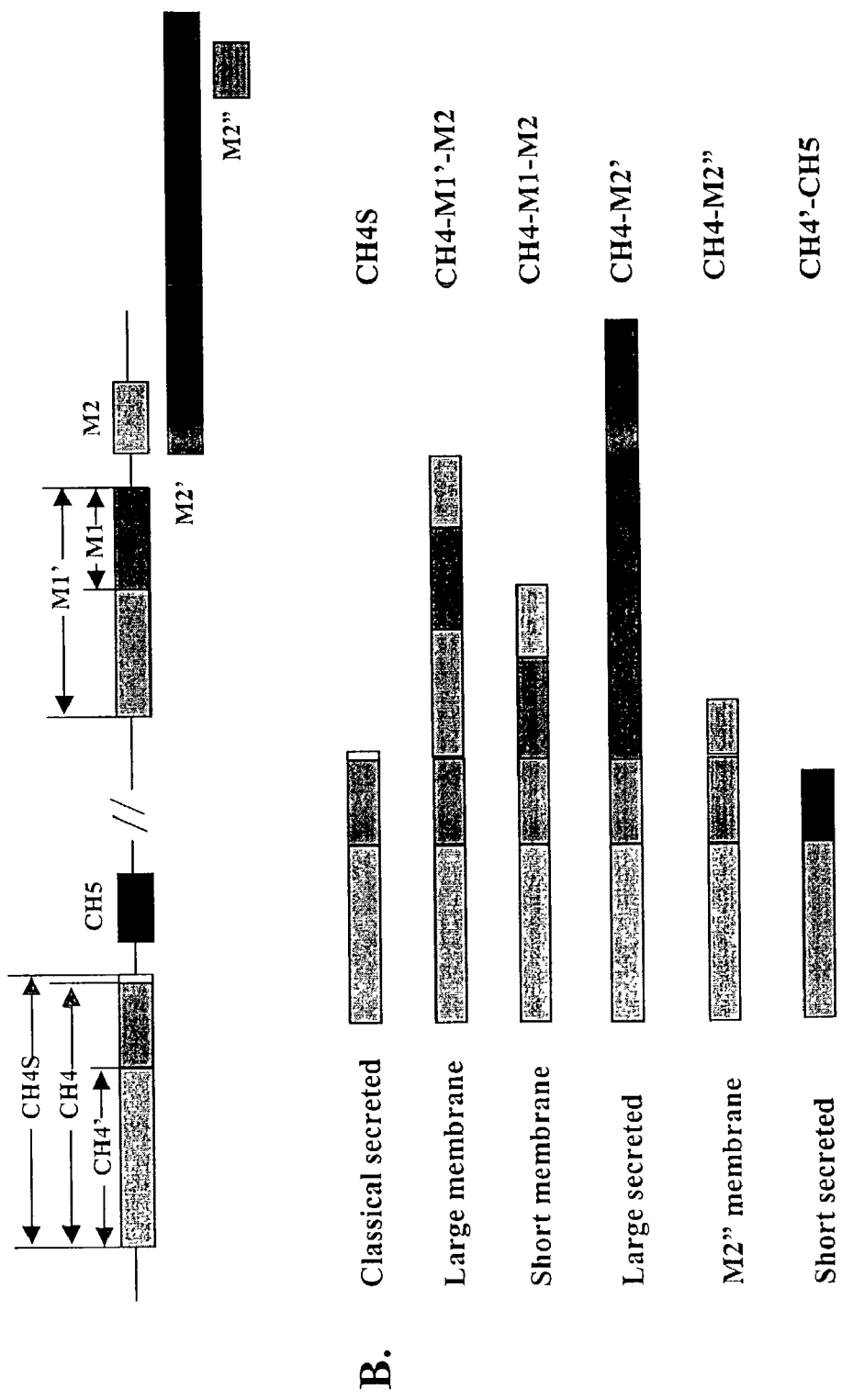

FIG. 17A depicts the different starting regions and combinations of membrane exons observed in differentially spliced human immunoglobulin E isoforms. FIG. 17B 1b depicts splicing maps diagramming the classical secreted IgE isoform (which lacks the membrane exons), as well as the large membrane isoform, the short membrane isoform, the long secreted isoform, the M2" membrane isoform, and the short secreted isoform. The fully assembled IgE products have differentially spliced frames, which can result in differing translated sequences due to shifting of the reading frame, even if the spliced messages overlap a large part of the exon sequence. IgE peptides generated by such different isoforms that differ in the amino acid sequences of membrane exons can provide additional therapeutic targets for cytotoxic T-lymphocytes.

Figure 18A:
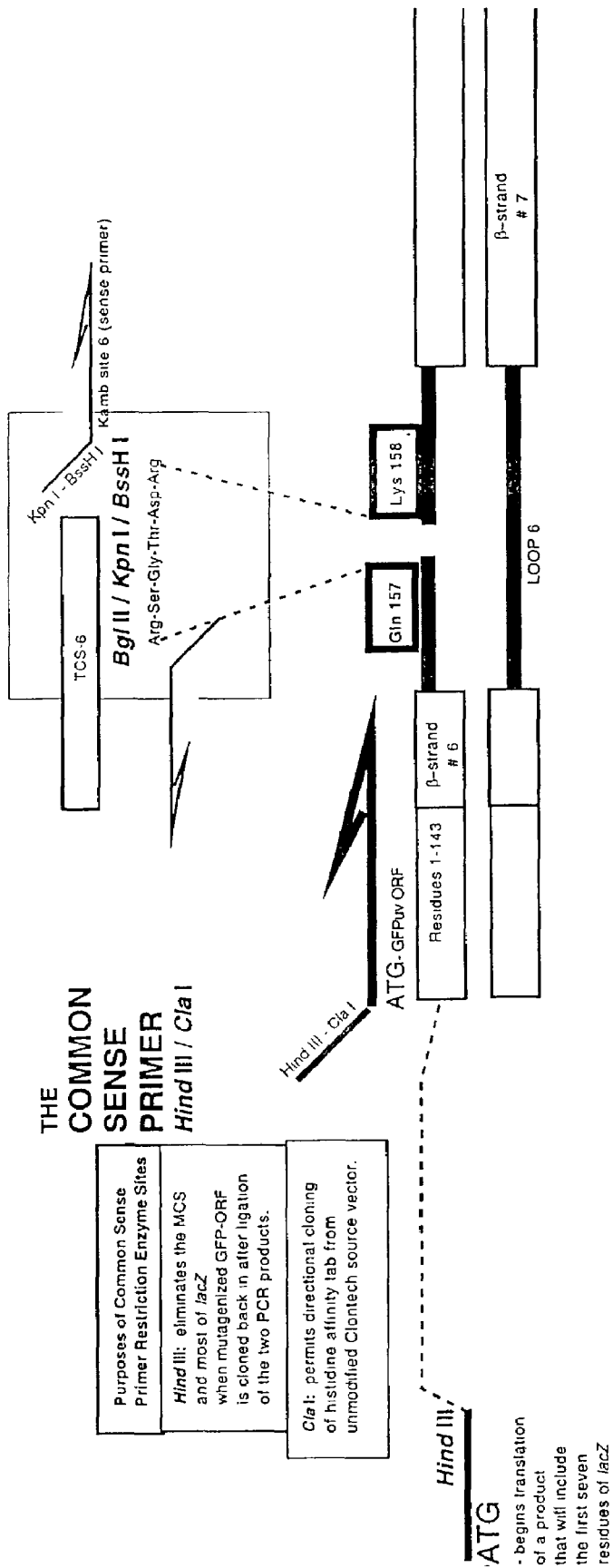
Figure 18B:
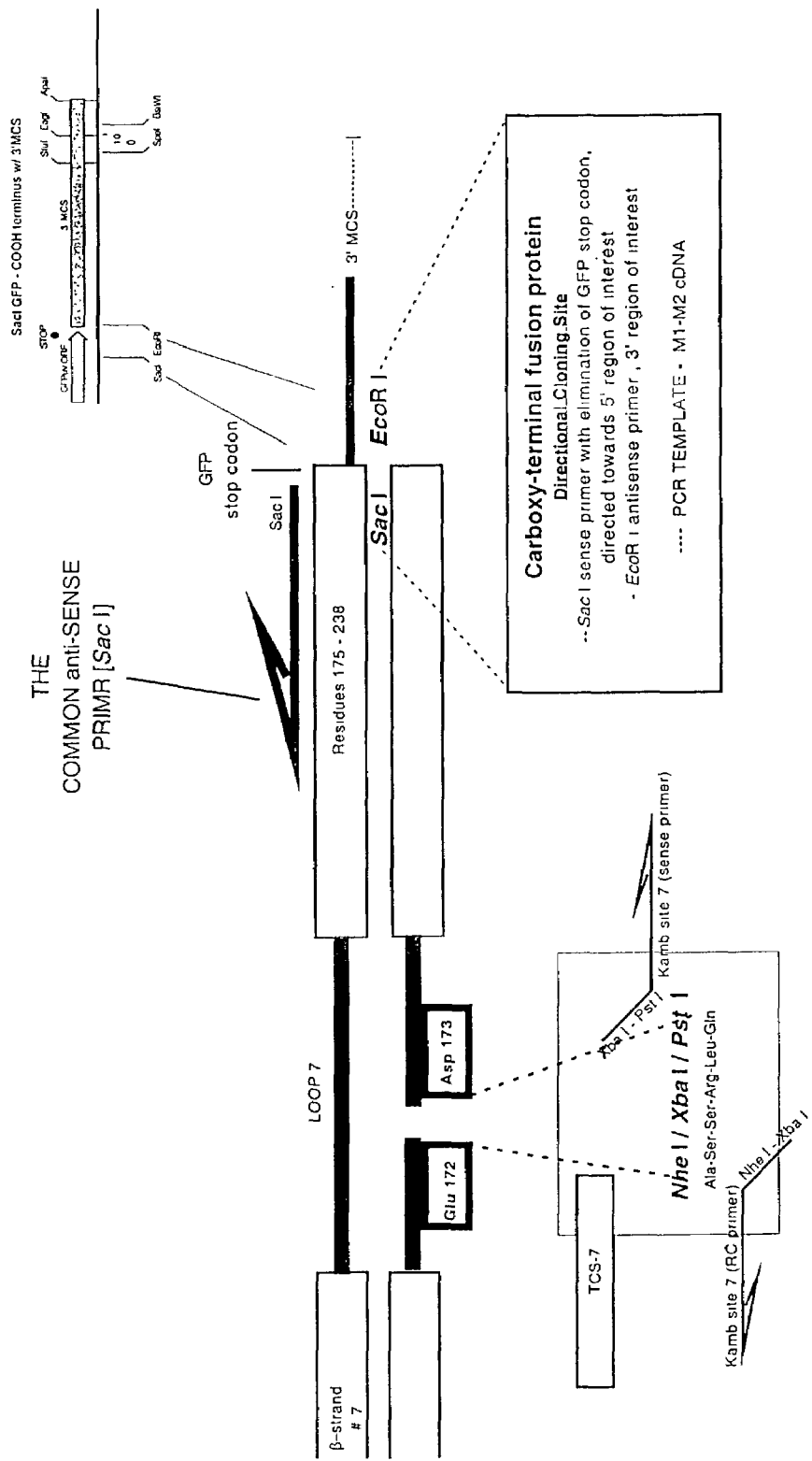

FIG. 18 depicts regions of the modified GFP$_{UV}$ vector used to express cytotoxic T-lymphocyte IgE peptides by a three-step PCR strategy. This GFP$_{UV}$ vector was modified by the additional of restriction enzyme sites into site 6 in loop 6 and site 7 in loop 7. FIG. 18A depicts site 6, which is located at Gln 157 in loop 6, and contains ligation sites for the restriction enzymes Bgl II, Kpn I and BssH I. FIG. 18B depicts site 7, which is located at Glu 172 in loop 7, and contains ligation sites for the restriction enzymes Nhe I, Xba I, and Pst I. Oligonucleotides specifying defined sequences were ligated into these sites.

Figure 19:
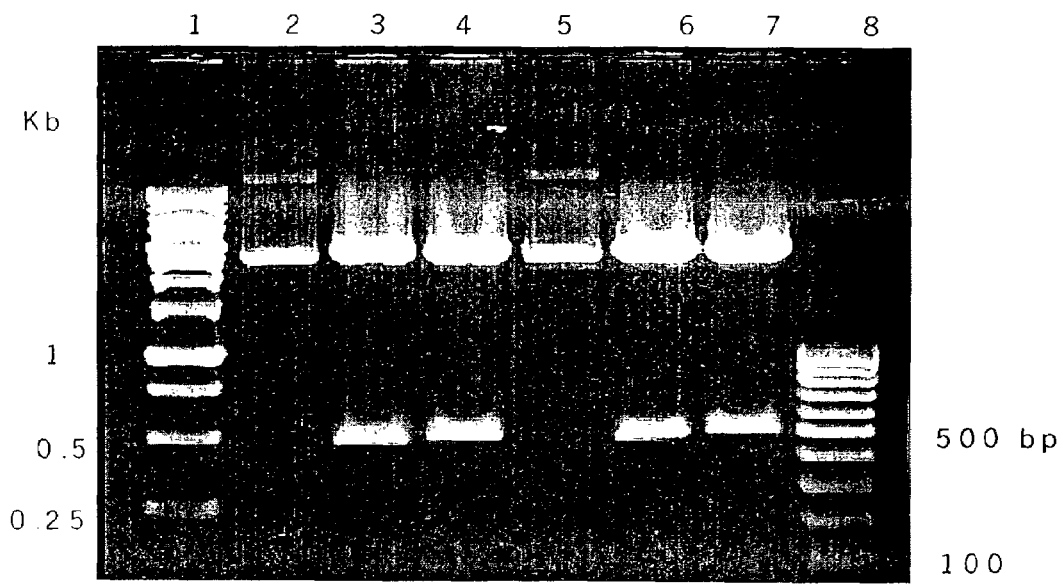

FIG. 19 depicts restriction enzyme digests of two clones (clone number 6/4 and clone number 6/5) obtained by the above three-step PCR strategy. These digests verified that the modified vector contained all the required sites as designed. Correct size of fragments, as predicted from the vector depicted in FIG. 18A and FIG. 18B, was observed for both clones following digestion by either SphI and Bgl II or by SphI and BssH I.

Figure 20:
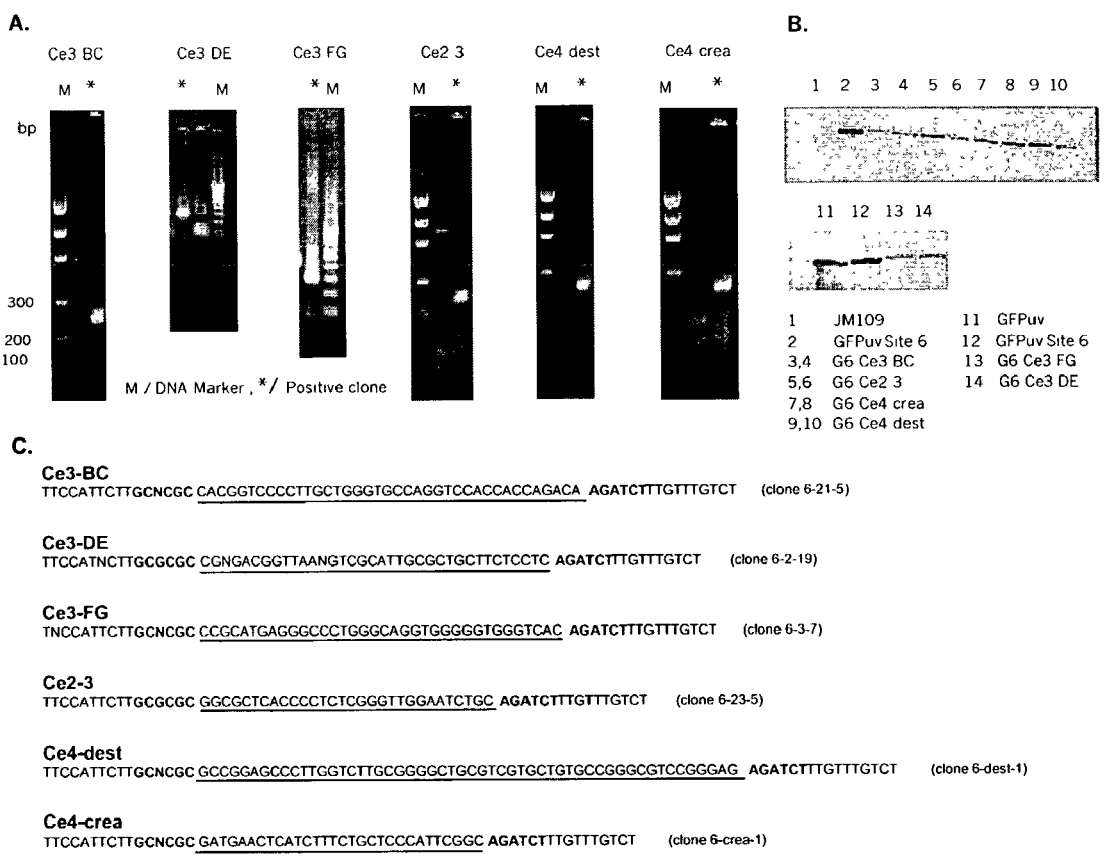

FIG. 20A depicts restriction digests of six clones (clones Ce3-BC, Ce3-DE, Ce3-FG, Ce2-3, Ce4-dest, and Ce4-crea) containing oligonucleotides encoding IgE cytotoxic T-lymphocyte epitopes, cloned as inserts into site 6 of the GFP$_{UV}$ vector. Lanes marked with "M" contain a DNA molecular weight ladder; lanes marked with "*" contain positive clones. The clones were expressed in JM109 cells and the cell lysates screened by Western blot, the results of which are depicted in FIG. 20B. Lane 1 contains lysates of the untransformed host E. Coli strain JM109; lanes 2 and 12 contain lysates of cells transformed with GFP$_{UV}$ vector with the site 6 modification; lanes 3 and 4 contain lysates of cells transformed with the Ce3-BC clone; lanes 5 and 6 contain lysates of cells transformed with the Ce2-3 clone; lanes 7 and 8 contain lysates of cells transformed with the Ce4-crea clone; lanes 9 and 10 contain lysates of cells transformed with the Ce4-dest clone; lane 11 contains lysates of cells transformed with GFP$_{UV}$ vector; lane 13 contains lysates of cells transformed with the Ce3-FG clone; and lane 14 contains lysates of cells transformed with the Ce3-DE clone. FIG. 20C depicts the nucleotide sequence (underlined nucleotides) of the six IgE cytotoxic T-lymphocyte epitopes cloned into site 6: Ce3-BC (SEQ ID NO. 56), Ce3-DE (SEQ ID NO. 57), Ce3-FG (SEQ ID NO. 58), Ce2-3 (SEQ ID NO. 59), Ce4-dest (SEQ ID NO. 60), and Ce4-crea (SEQ ID NO. 61).

SUMMARY

Figure 1:
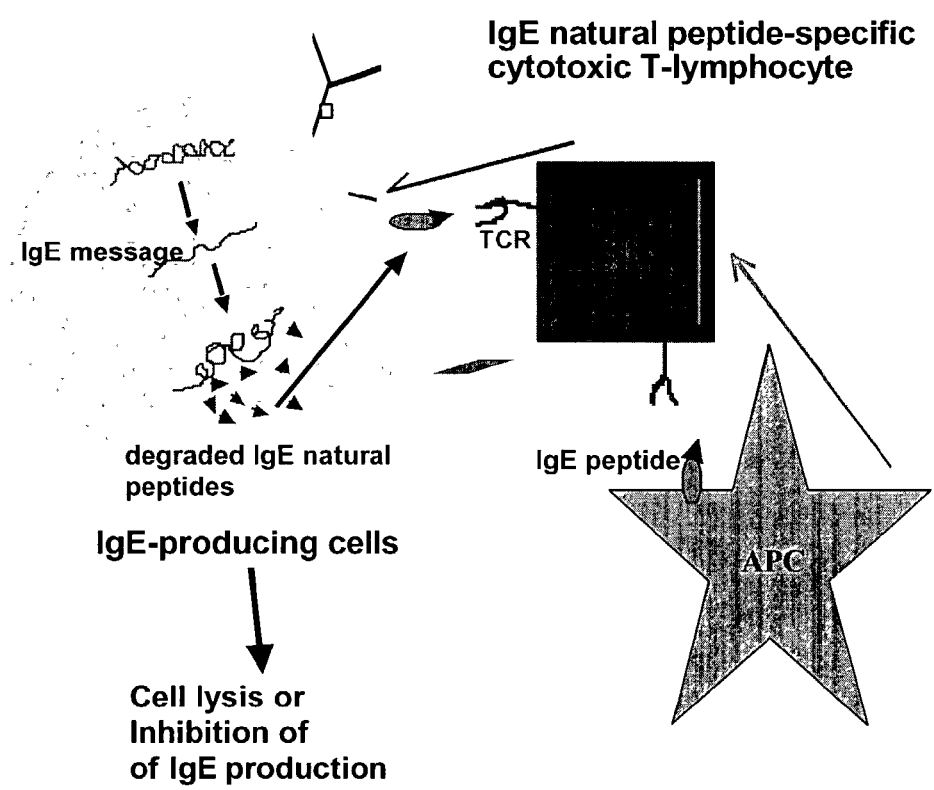
FIG. 1 depicts a schematic of an example of a vaccine of the present invention, consisting of immunogenic peptides derived from immunoglobulin E (IgE) that induce a cytotoxic T-lymphocyte (CTL) response against IgE peptides (depicted by shaded triangles) naturally processed and presented by a major histocompatibility complex class I (MHC-I) protein (depicted by shaded oval on cell surfaces). Such peptide-MHC-I complexes can be recognized by cytotoxic T-lymphocytes via T-cell receptors (TCR). For example, in IgE-producing cells, IgE peptides are naturally processed from the IgE heavy (H) chain, and presented on the MHC-I protein. Alternatively, an antigen-presenting cell (APC) can present naturally processed IgE peptides on the MHC-I protein. Such an immunized cytotoxic T-lymphocyte or "killer cell" recognizes and lyses cells presenting the IgE peptides on the MHC-I molecule.
Figure 2:
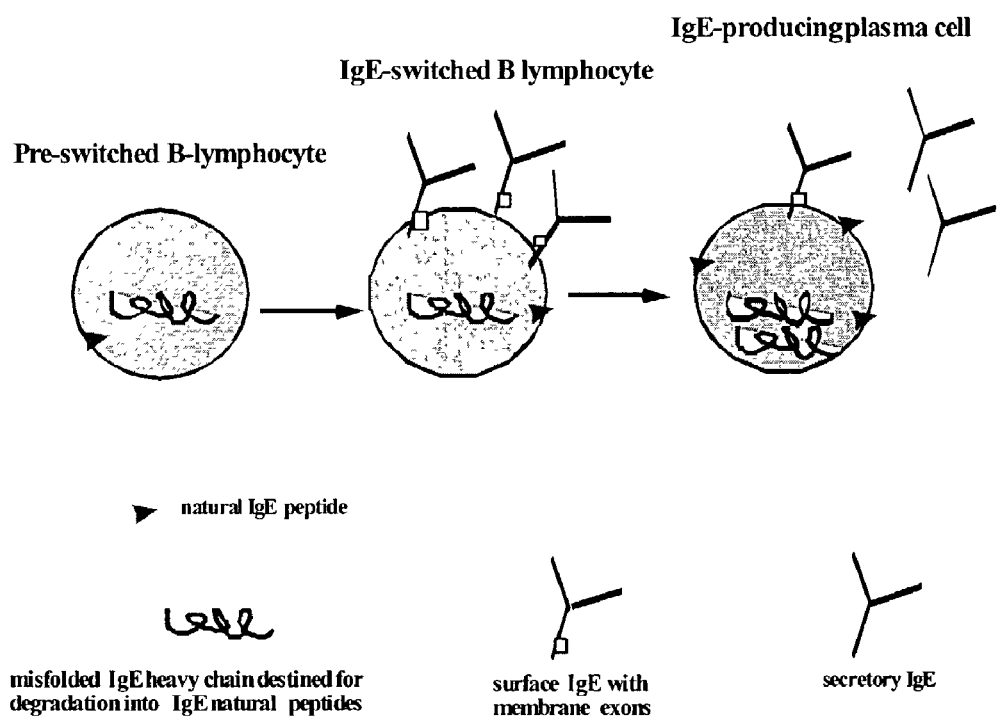
FIG. 2 depicts the three differentiation stages of IgE-producing B-lymphocytes, which are examples of targets for IgE-specific cytotoxic T-lymphocytes. Pre-switched B-lymphocytes express IgE heavy chain germ line transcripts under the influence of allergenic stimulations and may express low levels of IgE heavy chain prior to gene rearrangement. IgE-switched B-lymphocytes exhibit a high density of surface IgE anchored to the cell membrane via IgE membrane exons 1 and 2. IgE-secreting plasma cells express the highest levels of secretory IgE and thus the highest levels of naturally processed and presented IgE on MHC-I molecules. All three B-lymphocytes stages can serve as targets for an IgE-specific CTL response. Shaded triangles represent IgE peptides naturally processed and presented on the cell surface by an MHC-I molecule.

FIG. 1 illustrates one aspect of the present invention, which enables one to identify IgE peptides that are naturally processed and presented by MHC-I molecules and can elicit cytotoxic T-lymphocytes that are able to lyse cells displaying such peptides. The present invention is believed to promote the afferent limb of the immune system by inducing a cytotoxic T lymphocyte response to naturally processed and presented IgE peptides, using any necessary and appropriate modes of T-lymphocyte co-stimulation. It is known that there are at least five differentially spliced IgE mRNAs, which encode different translated products in IgE-producing plasma cells or normal human peripheral blood lymphocytes (PBL) (Batista et al., 1995, *J. Immunol.,* 154:209).

FIG. 2 diagrammatically illustrates that IgE molecules with the correctly encoded sequences and proper polypeptide folding can be secreted or assembled on cell surface via the IgE membrane exons. Misfolded IgE heavy chains, or products encoded by alternatively spliced, incomplete messages, are processed or degraded via a proteolytic pathway in the endoplasmic reticulum (ER). Peptides may be further exported outside for processing by proteosomes and re-transported into the ER (Pamer & Cresswell, 1998, *Annu. Rev. Immunol.,* 16:323; Shatri et al., 2002, *Annu. Rev. Immunol.,* 20:463). Homeostatic levels of these naturally processed IgE peptides are constantly produced and maintained. Along with peptides derived from other catabolized somatic proteins, naturally processed IgE peptides play a key role in the assembly and expression on the cell surface of MHC-I molecules by IgE-committed B-lymphocytes and plasma cells. Cells displaying such naturally processed IgE peptides, presented at the cell surface by MHC-I molecules, can become the targets for cytotoxic T-lymphocytes as an intrinsic physiological process of immunosurveillance. Since the IgE heavy chain does not vary isotypically in a given mammalian species, peptides naturally processed and presented from it can serve as a universal vaccine against IgE-mediated diseases in that mammalian species. Highly differentiated cell types, such as IgE-producing B-lymphocytes, display such IgE heavy chain peptides, and are lysed by these IgE-specific cytotoxic T-lymphocytes.

Existing anti-IgE therapy using anti-IgE antibodies aims at neutralizing circulating IgE only after the IgE response has been induced, but is not capable of inhibiting IgE production. Small molecule therapeutics, such as anti-histamines or leukotriene antagonists, are aimed at events downstream of the IgE response, and are believed to block the effect of mediators of allergen-IgE activated mast cells and basophils. The present invention has distinct advantages over these two earlier therapeutic approaches by interrupting or diminishing IgE-mediated allergic inflammation at its inception, that is, at the level of IgE production. The present invention's immunoglobulin E-specific cytotoxic T-lymphocyte response decreases undesirably high levels of circulating IgE by directly targetting IgE production by lysing IgE-producing cells, which are the presumptive source of circulating IgE in serum and mucosal fluid.

FIG. 2 illustrates three stage-specific IgE-producing targets of the IgE-specific CTL response: (1) pre-switched B-lymphocytes (Stage I B-lymphocytes), (2) IgE-switched B-lymphocytes (Stage II B-lymphocytes), and (3) IgE-producing plasma cells (Stage III B-lymphocytes). Pre-switched B-lymphocytes are mature cell surface IgM/IgD-positive B-lymphocytes expressing IgE heavy chain germ line transcripts under the influence of allergenic stimulations such as allergens and cytokines (Gauchat, 1990, *J. Exp. Med.,* 172:463). They may express low levels of IgE heavy chain prior to gene rearrangement (Yaoita et al., 1982, *Nature,* 297:697). The transition from Stage I to Stage II, is preceded by switching from germ-line IgE transcript to differentially spliced IgE messages (Jung et al., 1993, *Science,* 259:984). Naturally processed IgE peptides are already present in this transition process. The present invention's IgE-specific cytotoxic T-lymphocyte response impedes the transition from Stage I to Stage II. Stage II B-lymphocytes exhibit a high density of surface IgE anchored to the cell membrane via IgE membrane exons 1 and 2 (Achatz et al., 1997, *Science,* 276:409), and are lysed by the present invention's IgE-specific cytotoxic T-lymphocytes. Following allergen and IL-4 stimulation, Stage II B-lymphocytes are transformed into Stage III, IgE-secreting plasma cells. The present invention's IgE-specific cytotoxic T-lymphocytes lyse allergen-activated Stage II B-lymphocytes in the process of transforming to Stage III cells. Stage III cells are IgE-secreting plasma cells. These cells expressed the highest levels of secretory IgE and thus the highest levels of naturally processed and presented IgE on MHC-I molecules. These are therefore the most conspicuous cellular targets for the present invention's IgE-specific cytotoxic T-lymphocytes.

The present invention's immunoglobulin E-specific cytotoxic T-lymphocyte response also targets other cells that display naturally processed and presented IgE peptides, such as mast cells or basophils that have IgE bound to their surface via the FceRI receptor, and thus decreases the level of mast cells or basophils in blood and in allergy-affected tissues. FIG. 1 and FIG. 2 depict the exocytic pathway of IgE peptides processing and presentation on MHC-I molecules. IgE peptides recognized as epitopes by cytotoxic T-lymphocytes can also be generated by the endocytic pathway (Watts, 1997, *Annu. Rev. Immunol.,* 15:821; Rock and Gamble, 1990, *Science,* 249:918). Mast cells are known to process exogenous antigens on MHC-I molecules (Malaviya et al., 1996, *J. Immunol.,* 156:1490). Mast cells and basophils that bind IgE-allergen complexes via the FceRI receptor can also display naturally processed and presented IgE peptides on MHC-I molecules, and are thus susceptible to lysis by the present invention's IgE-specific cytotoxic T-lymphocytes.

The present invention concerns, among other things, novel approaches to the therapy or prophylaxis of immunoglobulin E-mediated disease conditions. The present invention provides a method for identifying peptides that induce a cytotoxic T-lymphocyte response against immunoglobulin E.

The present invention also provides compositions that include at least one isolated immunogenic peptide identified by a method of the present invention, such as those able to bind to at least one major histocompatibility complex class I molecule and to elicit in a mammal a cytotoxic T-lymphocyte response to naturally processed and presented immunoglobulin E peptides. The present invention further provides compositions that include at least one isolated polynucleotide encoding the sequence for an immunogenic peptide identified by a method of the present invention, such as those able to bind to at least one major histocompatibility complex class I molecule and to elicit in a mammal a cytotoxic T-lymphocyte response to naturally processed and presented immunoglobulin E peptides. The present invention further provides compositions that include antigen-presenting cells that recognize at least one isolated immunogenic peptide identified by a method of the present invention, such as those able to bind to at least one major histocompatibility complex class I molecule and to elicit in a mammal a cytotoxic T-lymphocyte response to naturally processed and presented immunoglobulin E peptides.

The present invention also provides methods for modulating an immunoglobulin E-mediated condition in a mammal, including providing to the mammal a composition that elicits in the mammal a cytotoxic T-lymphocyte response to naturally processed and presented immunoglobulin E peptides, in an amount sufficient to elicit a cytotoxic T-lymphocyte response in the mammal. These compositions can include one or more peptides, nucleic acid molecules, and cells, and combinations thereof, optionally with one or more co-stimulatory factors.

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art. Where there are discrepancies in terms and definitions used in references that are incorporated by reference, the terms used in this application shall have the definitions given herein. Other technical terms used herein have their ordinary meaning in the art that they are used, as exemplified by a variety of technical dictionaries (Delves and Roitt, "Encyclopedia of Immunology", 2nd ed., Academic Press, New York, N.Y., 1998; Rosen et al., "Dictionary of Immunology", Stockton Press, New York, N.Y., 1989). The inventors do not intend to be limited to a mechanism or mode of action. Reference thereto is provided for illustrative purposes only.

I. Methods for Identifying Peptides

The present invention provides methods for identifying peptides that induce a cytotoxic T-lymphocyte response against immunoglobulin E. The peptides identified by such methods are useful in the production of active vaccines for therapy or prophylaxis in a mammal of immunoglobulin E-mediated conditions, including, for example, atopic hypersensitivity conditions and non-atopic hypersensitivity conditions. The method can include the steps of: a) providing at least one test peptide suspected of being able to bind to at least one major histocompatibility complex class I molecule, and b) evaluating the at least one test peptide for the ability to elicit in a mammal a cytotoxic T-lymphocyte response to naturally processed and presented immunoglobulin E peptides. Preferably, a peptide that induces such a response is identified.

Test Peptide

The test peptide can be provided by any suitable means or method known in the art. The test peptide can be naturally occurring, synthesized, combinatorially synthesized, or biologically or recombinantly produced, or an active fragment or active fragments thereof. An active fragment is a fragment of a peptide that retains at least one activity of a parent peptide such as but not limited to the ability to bind to a major histocompatibility class I molecule or the ability to elicit in a mammal a cytotoxic T-lymphocyte response, preferably the ability to elicit in a mammal a cytotoxic T-lymphocyte response to naturally processed immunoglobulin E peptides that are presented on a major histocompatibility class I molecule. Such active fragments are part of the present invention. A naturally occurring peptide may be isolated from any natural source, such as for example from whole blood, plasma, serum, or bone marrow. The test peptide can be made from digests of such naturally occurring peptides or other fragments such as active fragments thereof. The test peptide can be synthesized, for example chemically synthesized by conventional peptide synthesis. The test peptide can be synthesized by combinatorial synthesis, which may be based on conventional organic chemical synthesis, or on biochemical synthesis (using for example enzymes to catalyze reactions), or on both. The test peptide can also be biologically produced, for example by recombinant expression of the test peptide using a vector in a host cell by means known in the art (Sambrook et al., Molecular Biology: A Laboratory Manual (Third Edition) Cold Spring Harbor Press, Cold Spring Harbor, N.Y., (2001)), or by use of directed evolution methods such as yeast two-hybrid systems, protein fragment complementation assay, phage display, ribosome display, yeast surface display, and bacterial surface display techniques as described for example by Mössner and Plückthun (Mössner and Plückthun, 2001, *Chimia*, 55:324). Test peptides can contain amino acids that commonly occur in nature, that is to say those such as alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine, and valine. Test peptides can contain amino acids that rarely occur or do not occur in nature, such as but not limited to 2-aminoadipic acid, 3-aminoadipic acid, beta-alanine (beta-aminopropionic acid), 2-aminobutyric acid, 4-aminobutyric acid (piperidinic acid), 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine (sarcosine), N-methylisoleucine, N-methylvaline, norvaline, norleucine and ornithine. Test peptides can contain all L-amino acids, all D-amino acids, or a mixture of L- and D-amino acids. Test peptides can be additionally modified, for example by acylating the amino terminus or amidating the carboxy terminus to increase stability or half-life (Lipton, U.S. Pat. No. 5,028,592). Test peptides can be optionally labelled with a detectable moiety. Any suitable detectable moiety that renders the test peptide detectable can be used. Examples of detectable moieties include but are not limited to radioactive isotopes, non-radioactive isotopes, biotin, antigens detectable by specific antibodies, enzymes, particles (such as metal, polymer, latex, or magnetic particles), chromophores, fluorophores, or dyes. Such detectable moieties can be directly attached to the test peptide, or attached through a linker, or attached by non-covalent methods as are known in the art.

The test peptide can be a peptide of between about five to about two thousand amino acids in length, or a peptide of between about five to about one thousand four hundred amino acids in length, or a peptide of between about five to about one thousand amino acids in length, or a peptide of between about five to about five hundred amino acids in length, or an oligopeptide of between about five to about forty amino acids in length, or an oligopeptide of between about five to about seventeen amino acids in length. Shorter peptides (oligopeptides), such as those of between about five to about forty amino acids in length, or between about five and about twenty amino acids in length, in particular those of six, seven, eight, nine, ten, eleven, twelve, thirteen, fourteen, fifteen, sixteen, or seventeen amino acids in length, or between about five and about ten amino acids in length, can be more suitable to binding assays since the MHC-I binding site usually binds a peptide of between eight to ten amino acids in length (Pamer and Cresswell, 1998, *Annu. Rev. Immunol.,* 16:323; Shatri et al., 2002, *Annu. Rev. Immunol.,* 20:463). However, the addition of amino acids to the N-terminus or to the C-terminus of such an oligopeptide can be advantageous, for example, by increasing the peptide's stability and half-life in vitro or in circulation in vivo. Longer peptides can be more useful as vaccines. Test peptides can be linear or non-linear (for example, circular or branched).

The test peptide can contain an amino acid sequence derived from immunoglobulin E, for example, a sequence derived from the heavy chain of immunoglobulin E. For developing a vaccine against IgE for a particular species such as humans, the test peptide preferably contains an amino acid sequence derived from any of the constant region domains (CH1, CH2, CH3, or CH4 domains), or from the membrane exons of that species' IgE heavy chain, such as human IgE heavy chain.

Peptides identified as useful for one species can be used as guidance for identifying peptides useful for another species. For example, peptides identified in a mouse can be used to identify peptides as presumptively useful in humans. Identification of such presumptive peptides can be guided by, for example, predictive algorithms, such as those described herein or known in the art. The usefulness of such peptides can be confirmed by screening in vitro, in vivo, or ex vivo, or combinations thereof, using methods described herein. Such confirmed peptides can be further modified in sequence or structure and further screened for desirable activity. Such modification of sequence or structure can be guided by, for example, predictive algorithms, such as those described herein or known in the art.

Mammal

Mammals that can be used in the identification of the test peptide, or in which the test peptide may be used for prophylaxis or therapy of an IgE-mediated condition, can be any mammal with an immunoglobulin E and a major histocompatibility complex class I molecule of interest. Particularly useful in this regard are mammals of economic importance such as those used in food production (including cattle, swine, sheep, and goats), or for mammals of domestic importance such as those that are common companion animals or pets (including dogs, cats, horses, ferrets, mice, rats, rabbits, guinea pigs, gerbils, and hamsters). Also particularly useful are mammals that are non-human primates, such as lemurs, lorises, tarsiers, monkeys, and apes. Humans are included as mammals. Humans are also particularly useful for identification of the test peptide where the test peptide is to be used for prophylaxis or therapy of an IgE-mediated condition specific to humans.

Major Histocompatibility Complex Class I Molecule

The major histocompatibility complex class I (MHC-I) molecule to which the test peptide is suspected to bind can be any MHC-I molecule, including a mammalian MHC-I molecule, or an MHC-I molecule specific to humans such as a human leukocyte antigen (HLA). Preferably, the human leukocyte antigen is one that corresponds to a specific HLA haplotype, such as a particular HLA-A, HLA-B, HLA-C, and HLA-Cw serotype, or more specifically, a particular HLA genotype where more than one HLA genotype exists for a HLA serotype. Lists of known HLA serotypes and genotypes are publicly available, for example on the Internet website hiv.basic.nwu.edu/HLA/Reports/DoSeraGenoList.cfm.

The binding of the test peptide to the major histocompatibility complex class I molecule can optionally be predicted by an algorithm when the binding motif for that particular MHC-I molecule is known (Schueler-Furman et al, 2000, *Protein Sci.,* 9:1838; Andersen et al., 2000, *Tissue Antigens,* 55:519; Gulukota et al., 1997, *J. Mol. Biol.,* 267:1258; Brusic et al., 2002, *Immunol. Cell Biol.,* 80:280; Dzuris et al., 2000, *J. Immunol.,* 164:283; Rammensee et al., 1999, *Immunogenetics,* 50:213; Chelvanayagam, 1996, *Immunogenetics,* 45:15; Stryhn et al., 1996, *Eur. J. Immunol.,* 26:1911; Hammer, 1995, *Curr. Opin. Immunol.,* 7:263; Falk et al., 1993, *Semin. Immunol.,* 5:81). For example, about 180 binding motifs are known to date for the human MHC-I molecules HLA-A, HLA-B, HLA-C, and HLA-Cw. These HLA binding motifs are publicly available, for example on the Internet website hiv.basic.nwu.edu/HLA/Reports/DoMotifList.cfm. The algorithms are also publicly available, for example on the Internet websites bimas.dcrt.nih.gov/molbio/hla_bind/index.html, hiv.basic.nwu.edu/HLA/MotifScanner.cfm, and www.uni-tuebingen.de/uni/kxi/. A similar analysis can be performed for any MHC-I molecule for which the binding motif and algorithm is known. Other algorithms known in the art can also be used for this purpose.

Evaluation of Test Peptide-A

The methods of the present invention identify those test peptides that can be useful in the production of active vaccines for therapy or prophylaxis in a mammal of immunoglobulin E-mediated conditions. Test peptides are evaluated for the ability to elicit in a mammal a cytotoxic T-lymphocyte response to naturally processed and presented immunoglobulin E peptides. A variety of approaches can be used to evaluate a test peptide for this IgE-specific, CTL-inducing ability, examples of which follow.

One approach to evaluate a test peptide for the ability to elicit in a mammal a cytotoxic T-lymphocyte response to naturally processed and presented immunoglobulin E peptides includes the steps of: a) contacting the test peptide with mammalian cells defective in the expression of a chosen cell surface MHC-I molecule, and b) selecting from the test peptides those that cause expression of that MHC-I molecule on the cell surface of the defective cells. The defect in the mammalian cells can be for example a mutation of the transporter associated with antigen processing (TAP) proteins such as but not limited to TAP1 or TAP2.

Another approach to evaluate a test peptide for the ability to elicit in a mammal a cytotoxic T-lymphocyte response to naturally processed and presented immunoglobulin E peptides includes the steps of: a) contacting the test peptides with a chosen MHC-I molecule, and b) selecting from the test peptides those that bind to the MHC-I molecule. In practice the MHC-I molecule to be used in such a direct binding assay can be an isolated "MHC-I Moiety". This MHC-I Moiety can be for example a native protein (for example, an isolated intact MHC-I molecule), a complexed protein (for example, an MHC-I molecule complexed with beta-2 microglobulin, or an MHC-I molecule that is non-covalently bound to avidin), or an engineered protein (for example, a chimeric protein consisting in part of an MHC-I molecule), or active fragment thereof, so long as the MHC-I binding site is present and available for binding by the test peptide. Alternatively, the MHC-I molecule can be expressed on a cell surface. The test peptides can be tested for the ability to bind to such MHC-I expressing cells in vivo, ex vivo, or in vitro, or combinations thereof, using methods described herein or as known in the art. The MHC-I molecule expressed by these cells can be endogenous or exogenous (for example, as the result of transfecting the cell with the gene for a foreign MHC-I molecule). The ability of a test peptide to bind to a MHC-I molecule can be tested by any suitable technique (see for example Phizicky and Fields, 1995, *Microbiol Rev.*, 59:94). For example, the equilibrium dissociation constant $K_d$ can be calculated from measuring labelled test peptide that directly binds to the MHC-I molecule. As one alternative, unlabelled test peptide can be competed with the corresponding labelled test peptide for binding to the MHC-I molecule, and the binding affinity of each test peptide to the MHC-I molecule can be calculated from the inhibition concentrations ($IC_{50}$). As another alternative, the on rate and off rate of unlabelled test peptide binding to the MHC-I molecule can be measured, for example by surface plasmon resonance (SPR) techniques.

A further approach to evaluate a test peptide for the ability to elicit in a mammal a cytotoxic T-lymphocyte response to naturally processed and presented immunoglobulin E peptides includes the steps of: a) contacting the test peptides with mammalian cells defective in the expression of a chosen cell surface MHC-I molecule, b) selecting from the test peptides those that cause expression of that MHC-I molecule on the cell surface of the defective cells, c) preparing cytotoxic T-lymphocytes that recognize the selected peptide(s), and d) testing these cytotoxic T-lymphocytes for the ability to lyse target cells. The defect in the mammalian cells may be for example a mutation of the transporter associated with antigen processing (TAP) proteins such as but not limited to TAP1 or TAP2.

Preparation of Cytotoxic T-Lymphocytes

Cytotoxic T-lymphocytes (CTL) can be prepared by any of a number of ways. Illustrative methods are described herein, although alternative methods can be used. For example, cytotoxic T-lymphocytes can be prepared by immunizing a mammal that expresses the chosen cell surface MHC-I molecule with a selected peptide, and harvesting cytotoxic T-lymphocytes from the immunized mammal. The mammal can express the MHC-I molecule from an endogenous gene or from an exogenous gene. The immunization can include, in addition to the selected peptide, at least one co-stimulatory factor (Frauwirth and Thompson, 2002, *J. Clin. Invest.,* 109: 295). Suitable co-stimulatory factors include, for example, cytokines, mitogens, antibodies, antigen-presenting cells (Mayordomo et al., 1997, *Stem Cells,* 15:94), and peptides derived from a helper T-lymphocyte epitope foreign to the immunized mammal. Co-stimulatory factors may be delivered together with the peptide used for immunization, for example as a fusion with the peptide, or separately, for example, as a peptide encoded by a nucleic acid molecule. Cytotoxic T-lymphocytes can also be prepared by immunizing peripheral blood lymphocytes with a selected peptide, and harvesting cytotoxic T-lymphocytes from the immunized peripheral blood lymphocytes. As is the case for immunizing a mammal, the immunization of peripheral blood lymphocytes may include, in addition to the selected peptide, at least one co-stimulatory factor as described above, such as peptides derived from a helper T-lymphocyte epitope foreign to the immunized peripheral blood lymphocytes. Co-stimulatory factors may be delivered together with the peptide used for immunization, for example as a fusion with the peptide, or separately, for example, as a peptide encoded by a nucleic acid molecule.

Target Cells

The cytotoxic T-lymphocytes prepared by the above methods can be tested for their ability to lyse target cells. Target cells are any cell type that is recognized by the cytotoxic T-lymphocytes as having an immunoglobulin E molecule or fragment of an immunoglobulin E molecule, such as an IgE peptide that is naturally processed and presented by an MHC-I molecule on the cell's surface. The target cells and the cytotoxic T-lymphocytes can each be derived from the same mammalian species, or can each be derived from different mammalian species. One example of suitable target cells are mammalian cells defective in the expression of the chosen cell surface MHC-I molecule, where the cells have been contacted with the selected peptide or peptides, and where the selected peptide(s) cause(s) the MHC-I molecule to be expressed on the surface of the cells. The defect in the mammalian cells can be, for example, a mutation of the transporter associated with antigen processing (TAP) proteins TAP1 or TAP2. Another example of suitable target cells are mammalian cells that express the chosen cell surface MHC-I molecule, where the cells have been contacted with the selected peptide or peptides, and where the selected peptide(s) bind to the cell surface MHC-I molecule. The MHC-I molecule expressed by these cells can be expressed from an endogenous gene or from an exogenous gene. Another example of suitable target cells are immunoglobulin E-bearing cells, such as transitional (Stage I to Stage II) B-lymphocytes and Stage II B-lymphocytes. Another example of suitable target cells are immunoglobulin E-producing cells, such as IgE-secreting plasma cells or IgE-secreting tumor cells (for example, IgE myeloma cells). Particularly useful in developing a vaccine against IgE for humans are target cells that produce human immunoglobulin E. Another example of suitable target cells are cells that have immunoglobulin E bound to their surface, such as IgE-activated mast cell or basophils.

Evaluation of Test Peptide—B

Yet another approach to evaluate a test peptide for the ability to elicit in a mammal a cytotoxic T-lymphocyte response to naturally processed and presented immunoglobulin E peptides utilizes steps that resemble procedures outlined above, but includes the additional element of establishing a binding motif for the chosen MHC-I molecule. This approach includes the steps of: a) identifying and selecting test peptides that bind to the chosen MHC-I molecule, b) determining the amino acid sequence of the selected peptides, c) establishing an amino acid binding motif for the chosen MHC-I molecule from these determined amino acid sequences, d) providing second generation test peptides that have amino acid sequences derived from immunoglobulin E and that are predicted by an algorithm to bind to the established amino acid binding motif, and e) testing the second generation test peptides for the ability to elicit in a mammal a cytotoxic T-lymphocyte response to naturally processed and presented immunoglobulin E peptides, wherein a peptide that induces such a response is identified.

Identifying and Selecting

Step a) of the above approach can use any suitable process to identify and select test peptides that bind to the chosen MHC-I molecule. Such processes are described herein, although other approaches can be used.

One example of a suitable process to identify and select test peptides that bind to the chosen MHC-I molecule includes the steps of: a) contacting the test peptides with mammalian cells defective in the cell surface expression of the chosen MHC-I molecule, and b) selecting from the test peptides those that causes expression of the MHC-I molecule at the surface of the cells. The defect in the mammalian cells can be for example a mutation of the transporter associated with antigen processing (TAP) proteins such as but not limited to TAP1 or TAP2.

Another example of a suitable process to identify and select test peptides that bind to the chosen MHC-I molecule includes the steps of: a) contacting the test peptides with a chosen MHC-I molecule, and b) selecting from the test peptides those that bind to the MHC-I molecule. The MHC-I molecule to be used in such a direct binding assay can be any isolated MHC-I Moiety as described above, or active fragment thereof, so long as the MHC-I binding site is present and available for binding by the test peptide. Alternatively, the MHC-I molecule can be expressed on a cell surface from an exogenous or an endogenous gene as described above. The test peptides can be tested for the ability to bind to such MHC-I expressing cells in vivo, ex vivo, or in vitro. The ability of a test peptide to bind to a MHC-I molecule can be tested as described herein or by any suitable technique such as those known in the art.

Another example of a suitable process to identify and select test peptides that bind to the chosen MHC-I molecule includes the steps of: a) contacting a display scaffold that displays the test peptide with mammalian cells defective in the cell surface expression of the chosen MHC-I molecule, and b) selecting from these test peptides those that cause expression of the MHC-I molecule at the surface of the cells. The display scaffold that displays the test peptide can be any suitable supporting macromolecule or macromolecular assemblage, such as a polypeptide (Kamb, et al., U.S. Pat. No. 6,025,485; Christmann et al., 1999, *Protein Eng.*, 12:797; Abedi et al., 1998, *Nucleic Acids Res.*, 26:623; Peelle et al., 2001, *J. Protein Chem.*, 20:507), a phage (He, 1999, *J. Immunol. Methods*, 231:105; Smith, 1985, *Science*, 228:1315), a ribosome (Schaffitzel et al., 1999, *Immunol. Methods*, 231: 119; Roberts, 1999, *Curr. Opin. Chem. Biol.*, 3:268), an mRNA (Wilson et al., 2001, *Proc. Natl. Acad Sci.*, 98:3750), or a yeast cell surface (Yeung and Wittrup, 2002, *Biotechnol. Prog.*, 18:212; Shusta et al., 1999, *J. Mol. Biol.*, 292:949), a bacterial cell surface (Leenhouts et al., 1999, *Antonie Van Leeuwenhoek*, 76:367; Christmann et al., 2001, *Immunol. Methods*, 257:163), or a bacterial spore surface (Wittrup, 2001, *Curr. Opin. Biotechnol.*, 12:395; Boder and Wittrup, 1998, *Biotechnol. Prog.*, 14:55). For example, test peptides can be displayed as inserts within exposed loops of a peptide such as a conformationally constrained polypeptide such as green fluorescent protein (Abedi et al., 1998, *Nucleic Acids Res.*, 26:623), displayed as inserts within the phage coat proteins PiII or PVIII of a filamentous bacteriophage, such as M13, fd, or fl phage (Smith, 1985, Science, 228:13 15), displayed as an mRNA-peptide fusion (Wilson et al., 2001, *Proc. Natl. Acad Sci.*, 98:3750), or displayed as a heterologous or chimeric peptide expressed on the surface of bacterial cells (Gunneriusson et al., 1999, *Appl. Env. Microbiol.*, 65:4134). The defect in the mammalian cells can be for example a mutation of the transporter associated with antigen processing (TAP) proteins TAP1 or TAP2.

Another example of a suitable process to identify and select test peptides that bind to the chosen MHC-I molecule includes the steps of: a) contacting a display scaffold that displays the test peptide with the chosen MHC-I molecule, and b) selecting from these test peptides those that bind to the MCH-I molecule. Any suitable display scaffold as described above can be used to display the test peptides. The MHC-I molecule to be used in such a direct binding assay can be any isolated MHC-I Moiety as described above, or active fragment thereof, so long as the MHC-I binding site is present and available for binding by the test peptide. Alternatively, the MHC-I molecule can be expressed on a cell surface from an exogenous or an endogenous gene as described above. The test peptides can be tested for the ability to bind to such MHC-I expressing cells in vivo, ex vivo, or in vitro. The ability of a test peptide to bind to a MHC-I molecule can be tested as described herein or by any suitable technique such as those known in the art.

Testing

Step e) of the above approach can use any suitable method to test the second generation test peptides for the ability to elicit in a mammal a cytotoxic T-lymphocyte response to naturally processed and presented immunoglobulin E peptides, wherein a peptide that induces such a response is identified. Such methods are described herein, although other approaches can be used.

One suitable method of testing the second generation test peptides includes the steps of: a) preparing cytotoxic T-lymphocytes that recognize a second generation test peptide, and b) testing these cytotoxic T-lymphocytes for their ability to lyse target cells. Cytotoxic T-lymphocytes that recognize a second generation test peptide can be prepared by any of a number of ways. Cytotoxic T-lymphocytes can be prepared by immunizing a mammal that expresses the chosen cell surface MHC-I molecule with a selected second generation test peptide, and harvesting cytotoxic T-lymphocytes from the immunized mammal. The mammal can express the MHC-I molecule from an endogenous gene or from an exogenous gene. The immunization can include, in addition to the selected second generation test peptide, at least one co-stimulatory factor (Frauwirth and Thompson, 2002, *J. Clin. Invest.,* 109:295). Suitable co-stimulatory factors include, for example, cytokines, mitogens, antibodies, antigen-presenting cells (Mayordomo et al., 1997, *Stem Cells,* 15:94), and peptides derived from a helper T-lymphocyte epitope foreign to the immunized mammal. Co-stimulatory factors may be delivered together with the second generation peptide used for immunization, for example as a fusion with the second generation peptide, or separately, for example, as a peptide encoded by a nucleic acid molecule. Cytotoxic T-lymphocytes that recognize a second generation test peptide can also be prepared by immunizing peripheral blood lymphocytes with a selected second generation test peptide and harvesting cytotoxic T-lymphocytes from the immunized peripheral blood lymphocytes. As is the case for immunizing a mammal, the immunization of peripheral blood lymphocytes can include, in addition to the selected second generation test peptide, at least one co-stimulatory factor as described above, such as peptides derived from a helper T-lymphocyte epitope foreign to the immunized peripheral blood lymphocytes. Co-stimulatory factors may be delivered together with the second generation peptide used for immunization, for example as a fusion with the second generation peptide, or separately, for example, as a peptide encoded by a nucleic acid molecule.

The cytotoxic T-lymphocytes that recognize a second generation test peptide are tested for their ability to lyse target cells. Target cells are any cell type that is recognized by the cytotoxic T-lymphocytes as having an immunoglobulin E molecule or fragment of an immunoglobulin E molecule, as described above. One example of suitable target cells are mammalian cells defective in the expression of the chosen cell surface MHC-I molecule, where the cells have been contacted with the selected second generation test peptide or peptides, and where the selected second generation test peptide(s) cause(s) the MHC-I molecule to be expressed on the surface of the cells. The defect in the mammalian cells can be for example a mutation of the transporter associated with antigen processing (TAP) proteins such as but not limited to TAP1 or TAP2.

Another example of suitable target cells are mammalian cells that express the chosen cell surface MHC-I molecule, where the cells have been contacted with the selected second generation test peptide or peptides, and where the selected peptide(s) bind to the cell surface MHC-I molecule. The MHC-I molecule expressed by these cells can be expressed from an endogenous gene or from an exogenous gene. Other examples of suitable target cells are immunoglobulin E-bearing cells, immunoglobulin E-producing cells (such as IgE-secreting plasma cells or IgE-secreting tumor cells), and cells that have immunoglobulin E bound to their surface (such as IgE-activated mast cell or basophils). Particularly useful in developing a vaccine against IgE for humans are target cells that produce human immunoglobulin E.

Another suitable method of testing the second generation test peptides includes the steps of: a) contacting the second generation test peptide the chosen MHC-I molecule, and b) selecting from these second generation test peptides those that bind to the chosen MHC-I molecule. The MHC-I molecule to be used in such a direct binding assay can be any isolated MHC-I Moiety as described above, or active fragment thereof, so long as the MHC-I binding site is present and available for binding by the second generation test peptide. Alternatively, the MHC-I molecule can be expressed on a cell surface from an exogenous or an endogenous gene as described above. The second generation test peptides can be tested for the ability to bind to such MHC-I expressing cells in vivo, ex vivo, or in vitro. The ability of a second generation test peptides to bind to a MHC-I molecule can be tested as described herein or by any suitable technique such as those known in the art.

II. Compositions Eliciting IgE-Specific Cytotoxic T-Lymphocytes

Immunogenic Peptides

The present invention also provides compositions that include at least one isolated immunogenic peptide identified by a method of the present invention as able to bind to at least one major histocompatibility complex class I molecule and to elicit in a mammal a cytotoxic T-lymphocyte response to naturally processed and presented immunoglobulin E peptides. Such compositions can be provided in pharmaceutically acceptable carriers, and can be provided to be administered using an appropriate dose, route of administration, and regime, to provide an appropriate end-point, such as prophylaxis, palliation, or amelioration of symptoms of immunoglobulin E-mediated disease conditions. Such dose, route of administration, regime, and end-point can be determined using methods known in the art. Appropriate toxicity and efficacy evaluation can also be evaluated using methods known in the art. Appropriate in vitro, in vivo, or ex vivo methods, or combinations thereof, can be utilized.

Pharmaceutically Acceptable Carriers

Compositions of the present invention can include, in addition to the immunogenic peptide or peptides, a pharmaceutically acceptable carrier. Suitable pharmaceutically acceptable carriers include diluents, excipients, or carrier materials, selected according to the intended form of administration and consistent with conventional pharmaceutical practice. Examples of suitable carriers include water, physiological saline, phosphate-buffered saline, saline buffered with a physiologically compatible salt, a water-in-oil emulsion, and an oil-in-water emulsion. The pharmaceutically acceptable carrier can also include appropriate stabilizers, disintegrating agents, binders, preservatives, flavoring agents, or coloring agents, as is consistent with conventional pharmaceutical practice ("Remington: The Science and Practice of Pharmacy", 20$^{th}$ edition, Gennaro (ed.) and Gennaro, Lippincott, Williams & Wilkins, 2000; Miller et al., U.S. Pat. No. 6,355,619; Adams et al., U.S. Pat. No. 6,342,220). The immunogenic peptide or peptides of the present invention can be formulated and used as tablets, capsules or elixirs for oral administration, suppositories for rectal administration, ointments, creams, or lotions for topical administration, sprays, aerosols, or inhalants, sterile solutions, suspensions or injectables, and the like. Injectables can be prepared in conventional forms either as liquid solutions or suspensions, as solid forms suitable for solution or suspension in liquid prior to injection, or as emulsions. Suitable excipients include, for example, water, saline, dextrose, mannitol, lactose, lecithin, albumin, sodium glutamate, cysteine hydrochloride, and the like. In addition, if desired, the injectable pharmaceutical compositions can contain minor amounts of nontoxic auxiliary substances, such as wetting agents, pH buffering agents and the like. If desired, an absorption enhancing preparation, such as liposomes, can be used.

Co-stimulatory Factors

The compositions can include, in addition to the immunogenic peptide or peptides, at least one co-stimulatory factor (Frauwirth and Thompson, 2002, *J. Clin. Invest.*, 109:295). Suitable co-stimulatory factors include, for example, such molecules as B7 and CD40, cytokines, mitogens, antibodies, antigen-presenting cells (Carreno and Collins, 2002, *Annu. Rev. Immunol.*, 20:29; Mayordomo et al., 1997, *Stem Cells*, 15:94), and peptides derived from a helper T-lymphocyte epitope foreign to the immunized mammal. Co-stimulatory factors can be delivered together with the immunogenic peptide used for immunization, for example as a fusion with the peptide, or separately, for example, as a peptide encoded by a nucleic acid molecule. In the case where the co-stimulatory factor is a peptide, the co-stimulatory peptide and the immunogenic peptide can be provided together on one or more "polypeptide framework" (Skerra, 2000, *J. Mol. Recognit.*, 13:167). Suitable polypeptide frameworks preferably contain at least one exposed loop region that is exposed to the hydrophilic environment, preferably is thermodynamically stable, and preferably can accept insertion of the immunogenic peptide or of the co-stimulatory peptide. Examples of such polypeptide frameworks include green fluorescent protein (GFP), staphylococcal nuclease, fibronectin, immunoglobulin (Ig), and heat shock protein (HSP).

Immunogenic Peptides

The immunogenic peptide or peptides used in the compositions of the present invention can be naturally occurring, synthesized, combinatorially synthesized, or biologically or recombinantly produced, or an active fragment or active fragments thereof, as described herein. An active fragment is a fragment of a peptide that retains at least one activity of a parent peptide such as but not limited to the ability to bind to a major histocompatibility class I molecule or the ability to elicit in a mammal a cytotoxic T-lymphocyte response, preferably the ability to elicit in a mammal a cytotoxic T-lymphocyte response to naturally processed immunoglobulin E peptides that are presented on a major histocompatibility class I molecule. A naturally occurring immunogenic peptide may be isolated from any natural source, such as for example from whole blood, plasma, serum, or bone marrow. The immunogenic peptide can be made from digests of such naturally occurring peptides or other fragments such as active fragments thereof. A naturally occurring immunogenic peptide can be isolated from any natural source, such as for example from whole blood, plasma, serum, or bone marrow. The immunogenic peptide can be synthesized, for example chemically synthesized by conventional peptide synthesis. The immunogenic peptide can be synthesized by combinatorial synthesis, which may be based on conventional organic chemical synthesis, or on biochemical synthesis (using for example enzymes to catalyze reactions), or on both. The immunogenic peptide can also be biologically produced, for example by recombinant expression of the immunogenic peptide using a vector in a host cell by means known in the art. Immunogenic peptides can contain amino acids that commonly occur in nature, amino acids that rarely occur or do not occur in nature, or a mixture. Immunogenic peptides can contain all L-amino acids, all D-amino acids, or a mixture of L- and D-amino acids. Immunogenic peptides can be additionally modified as described herein.

The immunogenic peptide can be a peptide of between about five to about two thousand amino acids in length, or a peptide of between about five to about one thousand four hundred amino acids in length, or a peptide of between about five to about one thousand amino acids in length, or a peptide of between about five to about five hundred amino acids in length, or an oligopeptide of between about five to about forty amino acids in length, or an oligopeptide of between about five to about seventeen amino acids in length. Shorter peptides (oligopeptides), such as those of between about five to about forty amino acids in length, or between about five and about twenty amino acids in length, in particular those of six, seven, eight, nine, ten, eleven, twelve, thirteen, fourteen, fifteen, sixteen, or seventeen amino acids in length, or between about five and about ten amino acids in length, can be more suitable to binding assays since the MHC-I binding site usually binds a peptide of between eight to ten amino acids in length (Pamer and Cresswell, 1998, Annu. Rev. Immunol., 16:323; Shatri et al., 2002, Annu. Rev. Immunol., 20:463). However, the addition of amino acids to the N-terminus or to the C-terminus of such an oligopeptide can be advantageous, for example, by increasing the peptide's stability and half-life in vitro or in circulation in vivo. The length of the immunogenic peptide takes into consideration the overall in vivo immunogenicity of the peptide, which can be influenced by the peptide's stability and half-life in vivo. Thus, while short oligopeptides can bind more readily to a major histocompatibility complex class I molecule in in vitro binding assays, longer immunogenic peptides can be more useful as vaccines. Longer immunogenic peptides can be cleaved in vivo to yield the actively immunogenic sequence. Immunogenic peptides can be linear or non-linear (for example, circular or branched), or can be inserted into a suitable polypeptide framework as described herein. Immunogenic peptides inserted into a polypeptide framework, such as an immunoglobulin, can be processed through the endogenous degradative pathway and are presented to T-lymphocytes in the context of MHC class I molecules (Billetta et al., 1995, Eur. J. Immunol., 25:776).

The immunogenic peptide can contain an amino acid sequence derived from immunoglobulin E, for example, a sequence derived from the heavy chain of immunoglobulin E. For developing a vaccine against IgE for a particular species such as humans, the immunogenic peptide preferably contains an amino acid sequence derived from any of the constant region domains (CH1, CH2, CH3, or CH4 domains), or from the membrane exons of that species' IgE heavy chain, such as human IgE heavy chain.

The immunogenic peptide or peptides of the composition are preferably able to bind to a major histocompatibility complex class I molecule, which can be any MHC-I molecule, including a mammalian MHC-I molecule. For use as a vaccine against IgE in humans, the immunogenic peptide preferably binds to an MHC-I molecule specific to humans such as a human leukocyte antigen (HLA). Preferably, the human leukocyte antigen is one that corresponds to a specific HLA haplotype, such as a particular HLA-A, HLA-B, HLA-C, and HLA-Cw serotype, or more specifically, a particular HLA genotype where more than one HLA genotype exists for a HLA serotype. For use as a vaccine, the immunogenic peptide can be delivered as a complexed peptide, for example, as an immunogenic peptide complexed with an MHC-I Moiety such as is described herein, whereby the immunogenic peptide is protected from proteases and thus exhibits a desirable gain in half-life. For cell- or tissue-specific delivery, the immunogenic peptide or complexed immunogenic peptide can optionally be covalently or non-covalently bound to a targetting or "homing" molecule, that is to say, a molecule, such as an integrin, that targets or "homes to" a particular type of tissue or cell, such as an antigen-presenting cell.

Formulations

The compositions containing the immunogenic peptide or peptides can be provided in any formulation suitable to the intended form of administration and consistent with conventional pharmaceutical practice ("Remington: The Science and Practice of Pharmacy", $20^{th}$ edition, Gennaro (ed.) and Gennaro, Lippincott, Williams & Wilkins, 2000). Examples of suitable formulations include a solid, a powder, a gel, a solution, a suspension, an emulsion, liposomes, microspheres, injectable particles, inhalable particles, or a dissolvable matrix (Miller et al., U.S. Pat. No. 6,355,619).

Polynucleotides

The present invention further provides compositions that include at least one isolated polynucleotide encoding the sequence for an immunogenic peptide identified by a method of the present invention as able to bind to at least one major histocompatibility complex class I molecule and to elicit in a mammal a cytotoxic T-lymphocyte response to naturally processed and presented immunoglobulin E peptides. Such compositions can be provided in pharmaceutically acceptable carriers, and can be provided to be administered using an appropriate dose, route of administration, and regime, to provide an appropriate end-point, such as prophylaxis, palliation, or amelioration of symptoms of immunoglobulin E-mediated disease conditions. Such dose, route of administration, regime, and end-point can be determined using methods known in the art. Appropriate toxicity and efficacy evaluation can also be evaluated using methods known in the art. Appropriate in vitro, in vivo, or ex vivo methods, or combinations thereof, can be utilized.

Pharmaceutically Acceptable Carriers

Compositions of the present invention can include, in addition to the isolated polynucleotide encoding the sequence for an immunogenic peptide, a pharmaceutically acceptable carrier. Suitable pharmaceutically acceptable carriers include diluents, excipients, or carrier materials, selected according to the intended form of administration and consistent with conventional pharmaceutical practice. Examples of suitable carriers include water, physiological saline, phosphate-buffered saline, saline buffered with a physiologically compatible salt, a water-in-oil emulsion, and an oil-in-water emulsion. The pharmaceutically acceptable carrier can also include appropriate stabilizers, disintegrating agents, binders, preservatives, flavoring agents, or coloring agents, as is consistent with conventional pharmaceutical practice ("Remington: The Science and Practice of Pharmacy", 20th edition, Gennaro (ed.) and Gennaro, Lippincott, Williams & Wilkins, 2000). The isolated polynucleotide encoding the sequence for an immunogenic peptide of the present invention can be formulated and used as tablets, capsules or elixirs for oral administration, suppositories for rectal administration, ointments, creams, or lotions for topical administration, sprays, aerosols, or inhalants, sterile solutions, suspensions or injectables, and the like. Injectables can be prepared in conventional forms either as liquid solutions or suspensions, as solid forms suitable for solution or suspension in liquid prior to injection, or as emulsions. Suitable excipients include, for example, water, saline, dextrose, mannitol, lactose, lecithin, albumin, sodium glutamate, cysteine hydrochloride, and the like. In addition, if desired, the injectable pharmaceutical compositions can contain minor amounts of nontoxic auxiliary substances, such as wetting agents, pH buffering agents and the like. If desired, an absorption enhancing preparation, such as liposomes, can be used.

Polynucleotide

"Polynucleotide" refers to a polymeric form of nucleotides of at least ten bases in length, either ribonucleotides or deoxyribonucleotides or a modified form of either type of nucleotide. The polynucleotides of the present invention can be a DNA molecule or an RNA molecule. Compositions of the invention where the polynucleotide is a DNA molecule are termed DNA vaccines (Felgner et al., U.S. Pat. No. 6,413, 942; Content et al., U.S. Pat. No. 6,384,018; Felgner et al., U.S. Pat. No. 6,214,804; Huebner et al., U.S. Pat. No. 5,846, 946; Felgner et al., U.S. Pat. No. 5,703,055; Felgner et al., U.S. Pat. No. 5,589,466; Hasan et al., 1999, *J. Immunol. Methods*, 229:1; Lewis and Babiuk, 1999, *Adv. Virus Res.*, 54:129; Gurunathan et al., 2000, *Annu. Rev. Immunol.*, 18:927). Compositions of the invention where the polynucleotide is a RNA molecule are termed RNA vaccines (McKenzie et al., 2001, *Immunol. Res.*, 24:225; Hoerr et al., 2000, *Eur. J. Immunol.*, 30:1; Ying et al., 1999, *Nature Med.*, 5:823). The polynucleotide of the invention can be single-stranded or double-stranded or any combination of both. The polynucleotide of the invention can be a naked polynucleotide or a complexed polynucleotide (Pachuk et al., 2000, *Curr. Opin. Mol. Ther.*, 2:188; Hoerr et al., 2000, *Eur. J. Immunol.*, 30:1). The polynucleotide of the invention can include a suitable vector, such as a mammalian expression vector or a viral vector. Suitable vectors include, but are not limited to, a phage, cosmid, retrovirus, vaccinia, adenovirus, adeno-associated virus, herpes simplex virus, papillomavirus, Epstein Barr virus (EBV), and the like (Nabel et al., U.S. Pat. No. 5,910,488). Preferably, the vector is defective in that it lacks functional virulence genes, such that it is not infective after introduction into the target cell (Zeng et al., 1998, *Cell Biol. Toxicol.*, 14:105; Sorma et al., 1999, *Nature Biotechnol.*, 17:224; Stratford-Perricaudet et al., 1992, *J. Clin. Invest.*, 90:626; Samulski et al., 1989, *J. Virol.*, 63:3822; Kaplitt et al., 1991, *Molec. Cell. Neurosci.*, 2:320). Alternatively, polynucleotides of the present invention may be introduced by lipofection in vivo using liposomes (Felgner et al., 1987, *Proc. Natl. Acad. Sci.*, 84:7413). Liposomes may be targeted to particular tissues or cell types by coupling lipids to other molecules, for example, receptor ligands or antibodies that bind to a particular cell type. Polynucleotides of the present invention, in vectors or not in vectors, may also be applied to or formulated within a matrix, such as a polymeric solid matrix, a semisolid or gel, or a membrane, which is introduced into or applied externally to the mammal or cell to be treated.

Polynucleotides of the present invention for gene therapy, in viral vectors, in liposomes, or not in a vector, may be also be introduced into cells ex vivo. Target cells may be removed from the body, the polynucleotides of the present invention, in or not in a vector, may be introduced into the cells by any appropriate method, such as by infection, as a calcium phosphate precipitate, by lipofection, electroporation, or other methods known or developed in the art. After introduction of the nucleic acid into the cells, the cells can be reintroduced into the body.

Co-stimulatory Factors

The compositions can include, in addition to the polynucleotide encoding the sequence for an immunogenic peptide, at least one co-stimulatory factor (Frauwirth and Thompson, 2002, *J. Clin. Invest.*, 109:295). Suitable co-stimulatory factors include, for example, such molecules as B7 and CD40, cytokines, mitogens, antibodies, antigen-presenting cells (Mayordomo et al., 1997, *Stem Cells*, 15:94), and peptides derived from a helper T-lymphocyte epitope foreign to the immunized mammal. Co-stimulatory factors can be delivered together with the polynucleotide used for immunization, for example as a fusion with the polynucleotide, or separately, for example as a peptide or a nucleic acid molecule encoding a peptide. These co-stimulatory factors can be delivered as genes, for example, as genes for a co-stimulatory cytokine or other co-stimulatory factor (Scheerlinck, 2001, *Vaccine*, 19:2647; Cohen et al., 1998, *FASEB J.*, 12:1611).

Encoded Immunogenic Peptide

The immunogenic peptide encoded by the polynucleotide of the present invention can be a peptide of between about five to about two thousand amino acids in length, or a peptide of between about five to about one thousand four hundred amino acids in length, or a peptide of between about five to about one thousand amino acids in length, or a peptide of between about five to about five hundred amino acids in length, or an oligopeptide of between about five to about forty amino acids in length, or an oligopeptide of between about five to about seventeen amino acids in length. Shorter peptides (oligopeptides), such as those of between about five to about forty amino acids in length, or between about five and about twenty amino acids in length, in particular those of six, seven, eight, nine, ten, eleven, twelve, thirteen, fourteen, fifteen, sixteen, or seventeen amino acids in length, or between about five and about ten amino acids in length, can be more suitable to binding assays since the MHC-I binding site usually binds a peptide of between eight to ten amino acids in length (Pamer and Cresswell, 1998, *Annu. Rev. Immunol.*, 16:323; Shatri et al., 2002, *Annu. Rev. Immunol.*, 20:463). However, the addition of amino acids to the N-terminus or to the C-terminus of such an oligopeptide can be advantageous, for example, by increasing the peptide's stability and half-life in vitro or in circulation in vivo. The length of the immunogenic peptide encoded by the polynucleotide of the present invention takes into consideration the overall in vivo immugenicity of the peptide, which may be influenced by the peptide's stability and half-life in vivo. Thus, while short oligopeptides can bind more readily to a major histocompatibility complex class I molecule in in vitro binding assays, longer immunogenic peptides can be more useful as vaccines. Longer encoded immunogenic peptides can be cleaved in vivo to yield the actively immunogenic sequence. Immunogenic peptides encoded by the polynucleotide of the present invention can be linear or non-linear (for example, circular or branched), or can be inserted into a suitable polypeptide framework itself encoded by the polynucleotide. Examples of such polypeptide frameworks include but are not limited to green fluorescent protein (GFP), staphylococcal nuclease, fibronectin, immunoglobulin (Ig), and heat shock protein (HSP). Immunogenic peptides inserted into a polypeptide framework, such as an immunoglobulin, can be processed through the endogenous degradative pathway and are presented to T-lymphocytes in the context of MHC-I molecules (Billetta et al., 1995, *Eur. J. Immunol.*, 25:776). The peptides encoded by the polynucleotides of the present invention can be screened for immunogenicity by methods described herein.

A polynucleotide of the present invention can also encode a fusion protein that includes at least a portion of the immunogenic peptide of the present invention and a polypeptide of interest. A polypeptide of interest can be any polypeptide, for example a detectable polypeptide, such as green fluorescent protein (GFP), or a sequence that aids in the purification of a polypeptide, such as the FLAG epitope. A polynucleotide that encodes a fusion protein can be made by operably linking a nucleic acid molecule that encodes a polypeptide of interest with a nucleic acid molecule that encodes at least a portion of the immunogenic peptide of the present invention. The operable linking can be direct or indirect, such as in the case where a linker connects the immunogenic peptide of the present invention with a polypeptide of interest. The polynucleotide of the present invention and the nucleic acid that encodes a polypeptide of interest are preferably operably linked in frame such that an immunogenic polypeptide of the present invention and an functional polypeptide of interest are translated from the nucleic acid, but that need not be the case.

The immunogenic peptide encoded by the polynucleotide of the invention can contain an amino acid sequence derived from immunoglobulin E, for example, a sequence derived from the heavy chain of immunoglobulin E. For use as a vaccine against IgE for a particular species such as humans, the polynucleotide of the invention preferably encodes an immunogenic peptide that contains an amino acid sequence derived from any of the constant region domains (CH1, CH2, CH3, or CH4 domains), or from the membrane exons of that species' IgE heavy chain, such as human IgE heavy chain.

The immunogenic peptide encoded by the polynucleotide of the present invention is preferably able to bind to a major histocompatibility complex class I molecule, which may be any MHC-I molecule, including a mammalian MHC-I molecule. For use as a vaccine against IgE in humans, the polynucleotide of the invention preferably encodes an immunogenic peptide that binds to an MHC-I molecule specific to humans such as a human leukocyte antigen (HLA). Preferably, the human leukocyte antigen is one that corresponds to a specific HLA haplotype, such as a particular HLA-A, HLA-B, HLA-C, and HLA-Cw serotype, or more specifically, a particular HLA genotype where more than one HLA genotype exists for a HLA serotype.

Formulations

Compositions of the present invention containing the polynucleotide encoding an immunogenic peptide can be provided in any formulation suitable to the intended form of administration and consistent with conventional pharmaceutical practice ("Remington: The Science and Practice of Pharmacy", 20$^{th}$ edition, Gennaro (ed.) and Gennaro, Lippincott, Williams & Wilkins, 2000). Examples of suitable formulations include a solid, a powder, a gel, a solution, a suspension, an emulsion, liposomes, microspheres, injectable particles, inhalable particles, or a dissolvable matrix (O'Hagan, 1998, *J. Pharm. Pharmacol.*, 50:1; Pachuk et al., 2000, *Curr. Opin. Mol. Ther.*, 2:188; Gurunathan et al., 2000, *Annu. Rev. Immunol.*, 18:927; Cohen et al., 1998, *FASEB J.*, 12:1611). Optionally, a suitable adjuvant, such as an immunostimulatory oligonucleotide can be included (Norman et al., 1999, *Meth. Mol. Med.*, 29:185; Klinman et al., 1999, *Vaccine*, 17:19; Davis et al., U.S. Pat. No. 6,406,705).

Antigen-Presenting Cells

The present invention further provides compositions that include antigen-presenting cells that recognize at least one isolated immunogenic peptide identified by a method of the present invention as able to bind to at least one major histocompatibility complex class I molecule and to elicit in a mammal a cytotoxic T-lymphocyte response to naturally processed and presented immunoglobulin E peptides. Such compositions can be provided in pharmaceutically acceptable carriers, and can be provided to be administered using an appropriate dose, route of administration, and regime, to provide an appropriate end-point, such as prophylaxis, palliation, or amelioration of symptoms of immunoglobulin E-mediated disease conditions. Such dose, route of administration, regime, and end-point can be determined using methods known in the art. Appropriate toxicity and efficacy evaluation can also be evaluated using methods known in the art. Appropriate in vitro, in vivo, or ex vivo methods, or combinations thereof, can be utilized.

Pharmaceutically Acceptable Carriers

Such compositions can include, in addition to the antigen-presenting cells that recognize the immunogenic peptide, a pharmaceutically acceptable carrier. Suitable pharmaceutically acceptable carriers include diluents, excipients, or carrier materials, selected according to the intended form of administration and consistent with conventional pharmaceutical practice. Examples of suitable carriers include water, physiological saline, phosphate-buffered saline, saline buffered with a physiologically compatible salt, cell culture medium, serum, or plasma. The pharmaceutically acceptable carrier can also include appropriate stabilizers, disintegrating agents, binders, preservatives, flavoring agents, or coloring agents, as is consistent with conventional pharmaceutical practice ("Remington: The Science and Practice of Pharmacy", 20$^{th}$ edition, Gennaro (ed.) and Gennaro, Lippincott, Williams & Wilkins, 2000). The isolated antigen-presenting cells that recognize the immunogenic peptide of the present invention can be formulated and used as suspensions for oral administration, suppositories or suspensions for rectal administration, ointments, creams, or lotions for topical administration, sprays, aerosols, or inhalants, sterile suspensions or injectables, and the like. Injectables can be prepared in conventional forms as suspensions, as solid forms suitable for suspension in liquid prior to injection, or as emulsions. Suitable excipients include, for example, water, saline, dextrose, mannitol, lactose, lecithin, albumin, sodium glutamate, cysteine hydrochloride, and the like. In addition, if desired, the injectable pharmaceutical compositions can contain minor amounts of nontoxic auxiliary substances, such as wetting agents, pH buffering agents and the like. If desired, an absorption enhancing preparation, such as liposomes, can be used.

Antigen-Presenting Cells

The antigen-presenting cells of the present invention can be any cells that recognize the immunogenic peptide and can elicit in a mammal a cytotoxic T-lymphocyte response to naturally processed and presented immunoglobulin E peptides. Preferably, the antigen-presenting cells are dendritic cells (Steinman and Pope, 2002, *J. Clin. Invest.*, 109:1519;

Bhardwaj, 2001, *Trends Mol. Med.,* 7:388; Mitchell and Nair, 2000, *Curr. Opin. Mol. Ther.,* 2:176; Morse and Lyerly, 2000, *Curr. Opin. Mol. Ther.,* 2:20).

Co-stimulatory Factors

The compositions can include, in addition to the antigen-presenting cells that recognize the immunogenic peptide, at least one co-stimulatory factor (Frauwirth and Thompson, 2002, *J. Clin. Invest.,* 109:295). Suitable co-stimulatory factors include, for example, such molecules as B7 and CD40, cytokines, mitogens, antibodies, other antigen-presenting cells (Mayordomo et al., 1997, *Stem Cells,* 15:94), and peptides derived from a helper T-lymphocyte epitope foreign to the immunized mammal. Co-stimulatory factors can be delivered together with the antigen-presenting cells used for immunization, or separately, for example as a peptide or a nucleic acid molecule encoding a peptide.

Recognized Immunogenic Peptide

The immunogenic peptide recognized by the antigen-presenting cells of the present invention can be a peptide of between about five to about two thousand amino acids in length, or a peptide of between about five to about one thousand four hundred amino acids in length, or a peptide of between about five to about one thousand amino acids in length, or a peptide of between about five to about five hundred amino acids in length, or an oligopeptide of between about five to about forty amino acids in length, or an oligopeptide of between about five to about seventeen amino acids in length. Shorter peptides (oligopeptides), such as those of between about five to about forty amino acids in length, or between about five and about twenty amino acids in length, in particular those of six, seven, eight, nine, ten, eleven, twelve, thirteen, fourteen, fifteen, sixteen, or seventeen amino acids in length, or between about five and about ten amino acids in length, can be more suitable to binding assays since the MHC-I binding site usually binds a peptide of between eight to ten amino acids in length (Pamer and Cresswell, 1998, *Annu. Rev. Immunol.,* 16:323; Shatri et al., 2002, *Annu. Rev. Immunol.,* 20:463). However, the addition of amino acids to the N-terminus or to the C-terminus of such an oligopeptide can be advantageous, for example, by increasing the peptide's stability and half-life in vitro or in circulation in vivo. The length of the immunogenic peptide recognized by the antigen-presenting cells takes into consideration the overall in vivo immugenicity of the peptide, which may be influenced by the peptide's stability and half-life in vivo. Thus, while short oligopeptides can bind more readily to a major histocompatibility complex class I molecule in in vitro binding assays, longer immunogenic peptides can be more useful as vaccines. Longer immunogenic peptides recognized by the antigen-presenting cells can be cleaved in vivo to yield the actively immunogenic sequence. Immunogenic peptides recognized by the antigen-presenting cells can be linear or nonlinear (for example, circular or branched), or can be inserted into a suitable polypeptide framework as described herein. Immunogenic peptides inserted into a polypeptide framework, such as an immunoglobulin, can be processed through the endogenous degradative pathway and are presented to T-lymphocytes in the context of MHC class I molecules (Billetta et al., 1995, *Eur. J. Immunol.,* 25:776).

The immunogenic peptide recognized by the antigen-presenting cells of the invention can contain an amino acid sequence derived from immunoglobulin E, for example, a sequence derived from the heavy chain of immunoglobulin E. For use as a vaccine against IgE for a particular species such as humans, the antigen-presenting cells of the invention preferably recognize an immunogenic peptide that contains an amino acid sequence derived from any of the constant region domains (CH1, CH2, CH3, or CH4 domains), or from the membrane exons of that species' IgE heavy chain, such as human IgE heavy chain.

The immunogenic peptide recognized by the antigen-presenting cells of the present invention is preferably able to bind to a MHC-I molecule, which can be any MHC-I molecule, including a mammalian MHC-I molecule. For use as a vaccine against IgE in humans, the antigen-presenting cells preferably recognize an immunogenic peptide that binds to an MHC-I molecule specific to humans such as a human leukocyte antigen (HLA). Preferably, the human leukocyte antigen is one that corresponds to a specific HLA haplotype, such as a particular HLA-A, HLA-B, HLA-C, and HLA-Cw serotype, or more specifically, a particular HLA genotype where more than one HLA genotype exists for a HLA serotype.

Formulations

The compositions containing the antigen-presenting cells that recognize an immunogenic peptide can be provided in any formulation suitable to the intended form of administration and consistent with conventional pharmaceutical practice ("Remington: The Science and Practice of Pharmacy", 20$^{th}$ edition, Gennaro (ed.) and Gennaro, Lippincott, Williams & Wilkins, 2000). The antigen-presenting cells can be intact cells, or cells that have been further processed, for example, into membranes preparations or subcellular fractions. Examples of suitable formulations include a cell suspension, a suspension of crude membrane extracts, a suspension of purified membranes, a suspension of subcellular membrane organelle fractions, and membrane preparations mixed with liposomes.

III. Methods for Modulating IgE-Mediated Conditions

The present invention also provides methods for modulating an immunoglobulin E-mediated condition in a mammal, comprising providing to the mammal a composition that elicits in the mammal a cytotoxic T-lymphocyte response to naturally processed and presented immunoglobulin E peptides, in an amount sufficient to elicit a cytotoxic T-lymphocyte response in the mammal.

Compositions

The compositions used by these methods can be any of the compositions described above, that is to say, any of the following: a) compositions that include at least one isolated immunogenic peptide identified by a method of the present invention, such as those as able to bind to at least one major histocompatibility complex class I molecule and to elicit in a mammal a cytotoxic T-lymphocyte response to naturally processed and presented immunoglobulin E peptides, b) compositions that include at least one isolated polynucleotide encoding the sequence for an immunogenic peptide identified by a method of the present invention, such as those as able to bind to at least one major histocompatibility complex class I molecule and to elicit in a mammal a cytotoxic T-lymphocyte response to naturally processed and presented immunoglobulin E peptides, and c) compositions that include antigen-presenting cells that recognize at least one isolated immunogenic peptide identified by a method of the present invention, such as those as able to bind to at least one major histocompatibility complex class I molecule and to elicit in a mammal a cytotoxic T-lymphocyte response to naturally processed and presented immunoglobulin E peptides. The compositions used by these methods may optionally include one or more co-stimulatory factor. The compositions used by these methods may also be a combination of the immunogenic peptides, nucleic acid molecules, or antigen-presenting cells described herein, optionally with one or more co-stimulatory factors.

Modulation

The methods of the present invention can modulate immunoglobulin E-mediated conditions in a mammal preferably by decreasing the level of circulating secreted immunoglobulin E in the mammal, by decreasing the level of circulating immunoglobulin E-bearing B-lymphocytes in the mammal, by decreasing the level of resident mucosal immunoglobulin E-bearing B-lymphocytes in tissues such as the bronchus-associated lymphoid tissues (BALT) and gut-associated lymphoid tissues (GALT), by decreasing the level of mast cells or basophilic granulocytes sensitized to immunoglobulin E in the mammal, or by decreasing the level of immunoglobulin E-producing cells in the mammal. Preferably, clinical endpoints such as, but not limited to, reduction of immunoglobulin E-mediated disease symptoms (for example, itching or burning eyes, nose, or throat; vomiting, constipation or diarrhea; sneezing, rhinorrhea, coughing or wheezing; dermatitis, eczema, or hives; asthma, shortness of breath, edema, or anaphylaxis) are achieved.

Immunoglobulin E-Mediated Conditions

The immunoglobulin E-mediated conditions modulated by the methods of the invention include but are not limited to atopic hypersensitivity conditions (such as allergic rhinitis, allergic asthma, food allergies, and contact allergies or atopic dermatitis), non-atopic hypersensitivity conditions (such as anaphylaxis, urticaria, and hives), and immunoglobulin E myeloma.

Mammals

Mammals in which modulation of an immunoglobulin E-mediated condition can be desirable include mammals of economic or domestic importance (such as cattle, swine, sheep, goats, dogs, cats, horses, ferrets, mice, rats, rabbits, guinea pigs, gerbils, and hamsters), non-human primates (such as lemurs, lorises, tarsiers, monkeys, and apes). It is particularly desirable to modulate immunoglobulin E-mediated conditions in humans.

Amounts, Route of Administration, and Regime

The amount of the composition sufficient to elicit a cytotoxic T-lymphocyte response in the mammal, and to thereby modulate an immunoglobulin E-mediated condition in that mammal, will necessarily vary according to the specific composition, the specific IgE-mediated condition, the species of the mammal, and possibly the individual mammal. The dose can be tailored to achieve a desired effect, but will depend on such factors as weight, diet, concurrent medication and other factors, which those skilled in the medical arts will recognize. In practicing the methods of the present invention, the compositions of the present invention can be used alone or in combination with one another, or in combination with other therapeutic agents (such as, but not limited to, antihistamines, leukotriene receptor antagonists, mast cell stabilizers, steroids, epinephrine, decongestants, antibiotics, and allergy desensitization treatments), or in combination with other diagnostic agents (such as, but not limited to, allergen skin tests, allergen blood tests, and histological examination). These products can be utilized in vivo, preferably in a mammalian patient, preferably in a human, or ex vivo or in vitro. In employing them in vivo, the compositions of the present invention can be administered to the patient in a variety of ways, including orally, parenterally, intravenously, subcutaneously, intramuscularly, colonically, rectally, nasally, ocularly, topically, or intraperitoneally, using a variety of appropriate doses and regimes to modulate the IgE-mediated condition. Such methods can also be used in testing bioactivities in vivo.

As will be readily apparent to one skilled in the art, the useful in vivo dosage to be administered and the particular mode of administration will vary depending upon the age, weight, and type of patient being treated, the particular composition of the present invention that is employed, and the specific use for which the composition is employed. The determination of effective dosage levels, that is to say, the dose levels necessary to achieve the desired result, can be accomplished by one skilled in the art using routine methods known to those of skill in the art. Typically, human clinical applications of products are commenced at lower dosage levels, with the dosage level being increased until the desired effect is achieved. Alternatively, acceptable in vitro or ex vivo studies or combinations thereof can be used to establish useful doses, routes of administration, and regimes of the compositions of the present invention. In non-human animal studies, applications of a composition of the present invention can be commenced at higher dose levels, with the dosage being decreased until the desired effect is no longer achieved, or adverse side effects are reduced or disappear. The efficacy of a given combination of a dosage level, mode of administration, and adminstration regime for a composition of the present invention can be monitored by any suitable method, for example, by measuring levels of immunoglobulin E in the patient (using, for example, ELISAs for IgE), by measuring levels of mediators (such as histamine or leukotrienes) or by monitoring symptoms of allergic disease (such as the severity of atopic dermatitis or atopic rhinitis).

The dosage for the compositions of the present invention can range broadly depending upon the desired effects, the therapeutic indication, route of administration, regime, and purity and activity of the composition. Where the composition is one that includes at least one isolated immunogenic peptide identified by a method of the present invention as able to bind to at least one major histocompatibility complex class I molecule and to elicit in a mammal a cytotoxic T-lymphocyte response to naturally processed and presented immunoglobulin E peptides, this amount can be between about 0.01 milligrams per kilogram body weight to about 10 milligrams per kilogram body weight, or between about 0.05 milligrams per kilogram body weight to about 10 milligrams per kilogram body weight, or between about 0.05 milligrams per kilogram body weight to about 5 milligrams per kilogram body weight, or between about 0.1 milligrams per kilogram body weight to about 5 milligrams per kilogram body weight, or between about 0.5 milligrams per kilogram body weight to about 5 milligrams per kilogram body weight, or between about 0.5 milligrams per kilogram body weight to about 1 milligrams per kilogram body weight of the isolated immunogenic peptide. Where the composition is one that includes at least one isolated polynucleotide encoding the sequence for an immunogenic peptide identified by a method of the present invention as able to bind to at least one major histocompatibility complex class I molecule and to elicit in a mammal a cytotoxic T-lymphocyte response to naturally processed and presented immunoglobulin E peptides, this amount can be between about 0.01 milligrams per kilogram body weight to about 10 milligrams per kilogram body weight, or between about 0.05 milligrams per kilogram body weight to about 10 milligrams per kilogram body weight, or between about 0.05 milligrams per kilogram body weight to about 5 milligrams per kilogram body weight, or between about 0.1 milligrams per kilogram body weight to about 5 milligrams per kilogram body weight, or between about 0.5 milligrams per kilogram body weight to about 5 milligrams per kilogram body weight, or between about 0.5 milligrams per kilogram body weight to about 1 milligrams per kilogram body weight of said at least one isolated polynucleotide. Where the composition is one that includes antigen-presenting cells that recognize at least one isolated immunogenic peptide identified by a method of the present invention as able to bind to at least one major histocompatibility complex class I molecule and to elicit in a mammal a cytotoxic T-lymphocyte response to naturally processed and presented immunoglobulin E peptides, this amount can be between about $1\times10^3$ antigen-presenting cells per kilogram body weight and $1\times10^8$ antigen-presenting cells per kilogram body weight, or between about $1\times10^4$ antigen-presenting cells per kilogram body weight and $1\times10^8$ antigen-presenting cells per kilogram body weight, or between about $1\times10^5$ antigen-presenting cells per kilogram body weight and $1\times10^8$ antigen-presenting cells per kilogram body weight, or between $1\times10^5$ antigen-presenting cells per kilogram body weight and $1\times10^7$ antigen-presenting cells per kilogram body weight.

The exact formulation, route of administration, regime, and dosage can be chosen by the individual physician in view of the patient's condition ("Goodman & Gilman's The Pharmacological Basis of Therapeutics", $10^{th}$ edition, Hardman (ed.) and Limberd, McGraw-Hill Professional Publishing, New York, N.Y., 2001). It should be noted that the attending physician would know how to and when to terminate, interrupt, or adjust administration due to toxicity, organ dysfunction, or other adverse effects. Conversely, the attending physician would also know to adjust treatment to higher levels if the clinical response were not adequate. The magnitude of an administrated dose in the management of the disorder of interest will vary with the severity of the condition to be treated and to the route of administration. The severity of the condition may, for example, be evaluated in part by standard prognostic evaluation methods for that condition. Further, the dose, and perhaps the dose frequency, will also vary according to the age, body weight, and response of the individual patient, including veterinary patients.

Depending on the specific conditions being treated, compositions of the present invention can be formulated and administered systemically or locally. Techniques for formation and administration can be found in "Remington: The Science and Practice of Pharmacy" ($20^{th}$ edition, Gennaro (ed.) and Gennaro, Lippincott, Williams & Wilkins, 2000). Suitable routes of administration can include oral, rectal, transdermal, otic, ocular, vaginal, transmucosal, or intestinal administration, or parenteral delivery, including intramuscular, subcutaneous, or intramedullary injections, as well as intrathecal, direct intraventricular, intravenous, intraperitoneal, intranasal, or intraocular injections.

For injection, the compositions of the present invention can be formulated in aqueous solutions, preferably in physiologically compatible buffers such as Hanks' solution, Ringer's solution, or physiological saline. For such transmucosal administration, penetrans appropriate to the barrier to be permeated are used in the formulation. Such penetrans are generally known in the art. Use of pharmaceutically acceptable carriers to formulate the compositions disclosed herein, for the practice of the methods of the invention, into dosages suitable for systemic administration is within the scope of the invention. With proper choice of carrier and suitable manufacturing practice, the compositions of the present invention, in particular, those formulated as solutions or suspensions, can be administered parenterally, such as by intravenous injection. The compositions of the present invention can be formulated readily using pharmaceutically acceptable carriers well known in the art into dosages suitable for oral administrations. Such carriers enable the compositions of the present invention to be formulated as tables, pills, capsules, liquids, gels, syrups, slurries, suspensions and the like, for oral ingestion by a patient to be treated.

Compositions of the present invention that are intended to be administered intracellularly may be administered using techniques well known to those of ordinary skill in the art. For example, such compositions may be encapsulated into liposomes, then administered as described above. Substantially all molecules present in an aqueous solution at the time of liposome formation are incorporated into or within the liposomes thus formed. The liposomal contents are both protected from the external micro-environment and, because liposomes fuse with cell membranes, are efficiently delivered into the cell cytoplasm. Additionally, due to their hydrophobicity, small organic molecules such as some peptides can be directly administered intracellularly.

Compositions of the present invention suitable for use in the methods described herein include compositions wherein the active ingredients are contained in an effective amount to achieve the composition's intended purpose. Preferably, the composition is provided in an amount sufficient to achieve a desired result, such as, but not limited to, prophylaxis, palliation, or amelioration of symptoms of immunoglobulin E-mediated disease conditions (for example, itching or burning eyes, nose, or throat; vomiting, constipation or diarrhea; sneezing, rhinorrhea, coughing or wheezing; dermatitis, eczema, or hives; asthma, shortness of breath, edema, or anaphylaxis). Appropriate regimes and routes of administration to achieve such results can be determined using methods described herein or known in the art. Determination of the effective amount of a composition of the present invention is well within the capability of those skilled in the art, especially in light of the detailed disclosure provided herein. In addition to the active ingredients (such as the immunogenic peptides, polynucleotides encoding immunogenic peptides, and antigen-presenting cells recognizing immunogenic peptides described in detail herein, or combinations thereof), compositions of the present invention can contain suitable pharmaceutically acceptable carriers including but not limited to excipients and auxiliaries that facilitate processing of the active ingredients into preparations which can be used pharmaceutically. The preparations formulated for oral administration may be in the form of tables, dragees, capsules, or solutions. The compositions of the present invention can be manufactured in a manner that is itself known, for example by means of conventional mixing, dissolving, granulating, dragee-making, emulsifying, encapsulating, entrapping or lyophilizing processes. Pharmaceutical formulations for parenteral administration include aqueous solutions of active ingredients in water-soluble form.

Additionally, suspensions of the active ingredients may be prepared as appropriate oily injection suspensions. Suitable lipophilic solvents or vehicles include fatty oils such as sesame oil, or synthetic fatty acid esters, such as ethyl oleate or triglycerides or liposomes. Aqueous injection suspensions may contain substances what increase the viscosity of the suspension, such as sodium carboxymethyl cellulose, sorbitol, or dextran. Optionally, the suspension can also contain suitable stabilizers or agents that increase the solubility of the active ingredients to allow for the preparation of highly concentrated solutions.

Compositions of the present invention for oral use can be obtained by combining the active ingredient with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol, cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone. If desired, disintegrating agents can be added, such as cross-linked polyvinylpyrrolidone, agar, or alginic acid or a salt thereof such as sodium alginate. Dragee cores can be provided with suitable coatings. Dyes or pigments can be added to the tablets or dragee coatings for identification or to characterize different combinations of active doses.

EXAMPLES

Example 1

Induction of an Immunoglobulin E-specific, Major Histocompatibility Complex Class I-restricted Cytotoxic T-lymphocyte Response by Test Peptides The following example describes the induction of an immunoglobulin E-specific, major histocompatibility complex class I-restricted cytotoxic T-lymphocyte response by test peptides.

The sequences of murine immunoglobulin E (IgE) test peptides suspected of being able to bind to specific murine major histocompatibility complex class I (MHC-I) molecules were predicted by algorithms for the MHC-I molecules publicly available on the world wide web at bimas.dcrt.nih.gov/molbio/hla_bind/index.html, syfpeithi.de, and hiv.basic.nw-u.edu/HLA/Reports/DoMotifList.cfm. The test peptide p1 for the murine MHC-I molecules H-2K$^d$ and H-2K$^b$ consisted of the nonameric amino acid sequence: Leu Tyr Cys Phe Ile Tyr Gly His Ile (SEQ ID NO. 1). The test peptide p2 for the murine MHC-I molecule H-2D$^d$ consisted of the nonameric amino acid sequence: Ile Tyr Gly His Ile Leu Asn Asp Val (SEQ. ID. NO. 2). Both test oligopeptides were synthesized by conventional 9-fluorenylmethoxycarbonyl (Fmoc) peptide chemistry.

Figure 3:
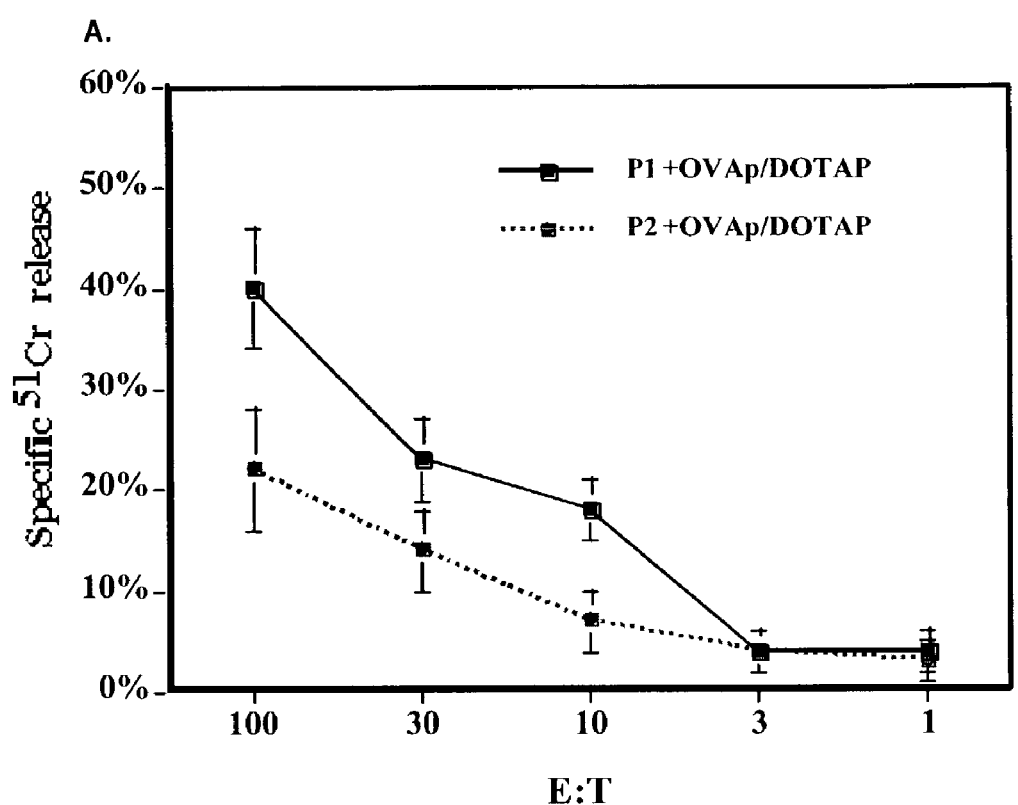
FIG. 3 depicts results of a standard chromium release assay using effector (E) cells at the indicated ratios to target (T) cells. Values shown are means of triplicate cultures with error bars indicating the standard deviation.
Figure 3:
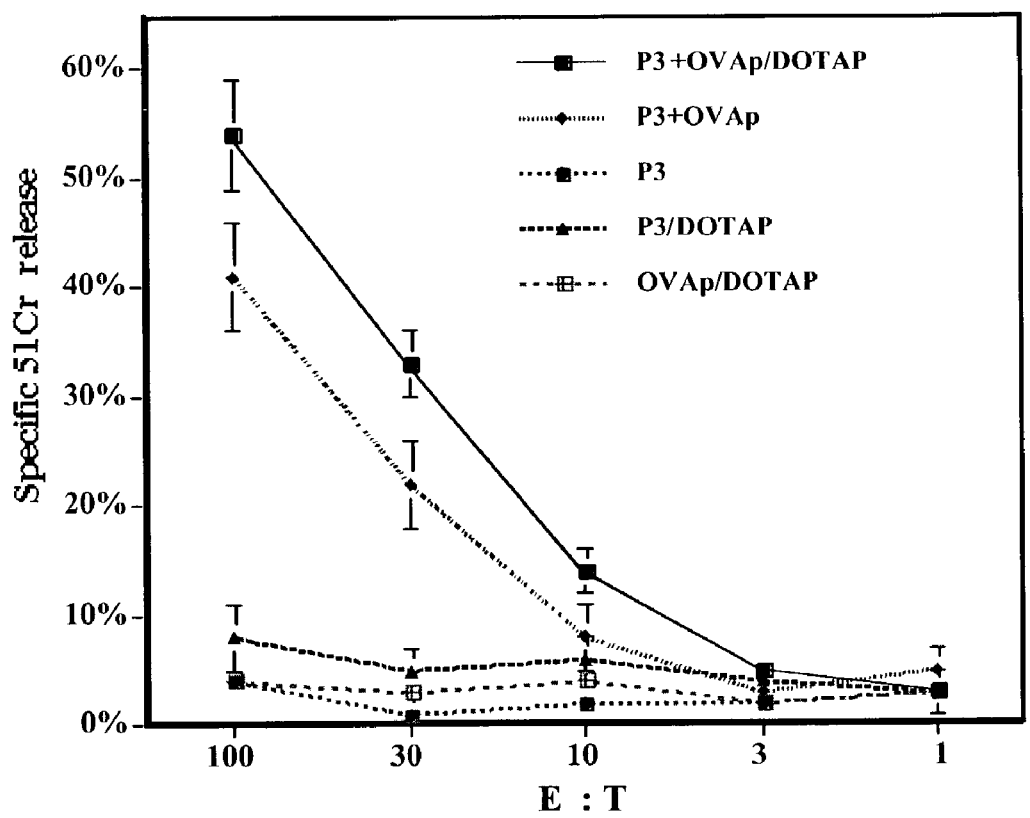
Figure 5:
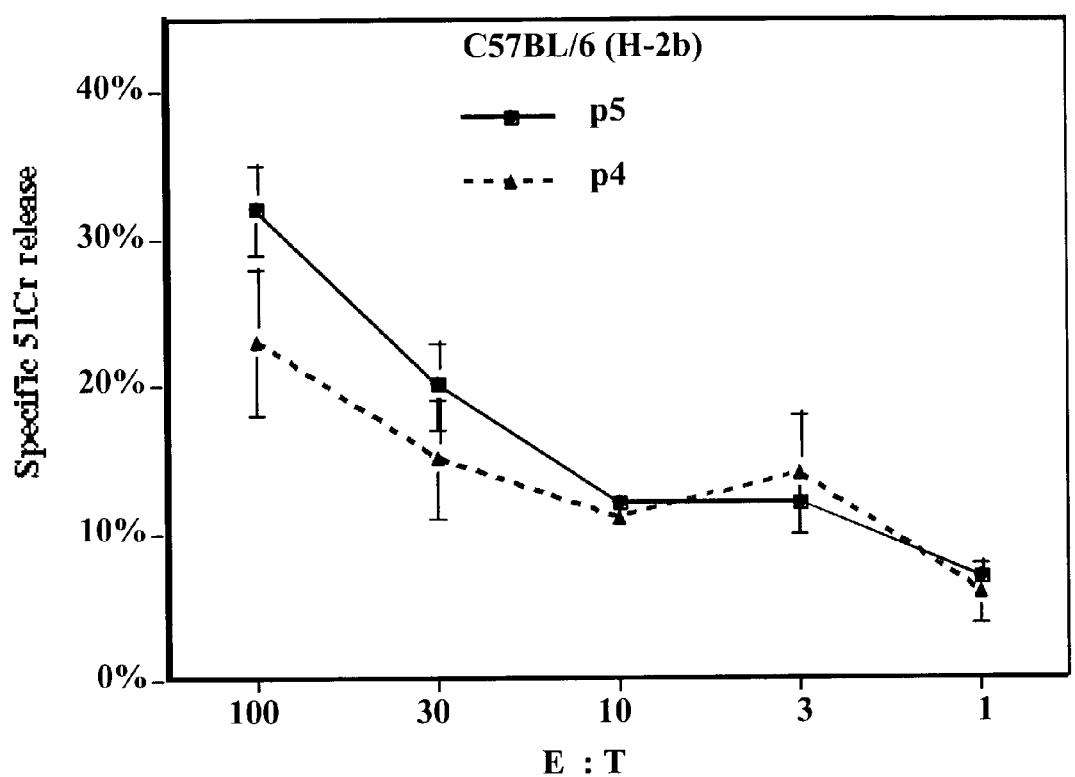
FIG. 5 depicts results of a standard chromium release assay using effector (E) cells at the indicated ratios to target (T) cells. Values shown are means of triplicate cultures with error bars indicating the standard deviation. Effector cells were cytotoxic T-lymphocytes obtained from C57BL/6 mice (expressing murine MHC-I haplotype H-$2^b$) that had been immunized with either the test peptide p4 with OVAp, or with the test peptide p5 in liposomes. Target cells were murine EL-4 lymphoma cells (expressing murine MHC-I haplotype H-$2^b$) that had been contacted with the test peptide p4 and interferon-gamma. These results show that mice immunized with either of the test peptides p4 or p5 developed comparable levels of immunoglobulin E-specific CTL response. This showed that p5 had been efficiently internalized into antigen-presenting cells, naturally processed and presented through the exogenous major histocompatibility complex class I pathway to yield immunogenic p4-derived peptide-MHC-I molecule complexes.

The test peptides p1 and p2 were evaluated for the ability to elicit in mice a cytotoxic T-lymphocyte response to naturally presented immunoglobulin E peptides. Eight-week old BALB/c mice in groups of four were each immunized with 30 micrograms of one of the test peptides p1 or p2, together with 30 micrograms of the co-stimulatory factor OVAp (ovalbumin peptide) (Schimokevitz, 1984, *J. Immunol.*, 133:2067), an oligopeptide consisting of the sequence Ile Ser Gln Ala Val His Ala Ala His Ala Glu Ile Asn Glu Ala Gly Arg (SEQ ID NO. 3), in N-[1-(-2,3-dioleoyloxy)propyl]-N,N,N-trimethylammonium methylsulfate (DOTAP, purchased from Boehringer Mannheim, Indianapolis, Ind.) cationic liposomes. Two weeks after the first immunization, mice in each respective group were immunized a second time with the appropriate test peptide (p1 or p2) that had been used in the initial immunization. Two weeks after the second immunization, 5×10$^6$ spleen cells were removed from a pool of two to four mice, established in vitro, and re-stimulated with the respective test peptide in vitro for seven days. The cytotoxic T-lymphocytes thus obtained were tested using a standard chromium release assay (Colligan et al. 2002, Current Protocols in Immunology, 3.11) for their ability as effector cells to lyse target cells. The target cells consisted of P815 murine mastocytoma cells that had been contacted with the appropriate test peptide (p1 or p2) and treated overnight with 50 units per milliliter interferon-gamma to facilitate processing of the test peptide. Effector cells (E) and target cells (T) were mixed at different E/T ratios for 4 hours. The specific lysis was determined by the following formula: [(experimental release−spontaneous release)/(maximal release−spontaneous release)]×100. The results are illustrated in FIG. 3A, which shows that both IgE-derived test peptides p1 and p2, delivered with a co-stimulatory peptide and with liposomes, were able to elicit a CTL response in BALB/c mice that was cytotoxic to target cells displaying the peptides.

The length of a test peptide can influence its half-life and immunogenicity. Serine and cysteine endopeptidases and serine carboxypeptidases are known to be involved in antigen processing (Germain, 1999, Fundamental Immunology, Ch. 9, p. 263, ed. Paul; Li, 2002, *Mol. Biochem. Parasitol.*, 120: 177; Gil-Torregrosa, et al., 1998, *J. Exp. Med.*, 188:1105). Therefore a third test peptide p3 was synthesized, which consisted of the overlapped nonameric amino acid sequences of the test peptides p1 and p2, with an N-terminus sixteen amino acid extension, derived from the CH2 domain of murine immunoglobulin E, and a C-terminus ten amino acid extension (FIG. 4) (Wang et al., 1996, *Eur. J. Immunol.*, 26:1043). The amino acid sequence of p3 was: Leu Leu His Ser Ser Cys Asp Pro Asn Ala Phe His Ser Thr Ile Gln Leu Tyr Cys Phe Ile Tyr Gly His Ile Leu Asn Asp Val Ser Val Ser Trp Leu Met Asp Asp Arg Glu (SEQ ID NO. 4). The serine endoproteinase Glu-C cleaves between the two residues Asp Val, which demarcate the majority of the overlapped p1/p2 sequence from the C-terminus ten amino acid extension.

The test peptide p3 was similarly evaluated for the ability to elicit a cytotoxic T-lymphocyte response in mice to naturally processed and presented immunoglobulin E peptides. Eight-week old BALB/c mice in groups of four were each immunized with 30 micrograms of the test peptide p3, with or without 30 micrograms of the co-stimulatory factor OVAp, in the presence or absence of 30 micrograms DOTAP liposomes. Two weeks later, mice were immunized a second time using the same protocol as in the first immunization. Two weeks after the second immunization, 5×10$^6$ spleen cells were removed from a pool of two to four mice, established in vitro, and re-stimulated with the test peptide p3 in vitro for seven days. The cytotoxic T-lymphocytes thus obtained were tested using a standard chromium release assay for their ability as effector cells to lyse target cells. The target cells consisted of P815 murine mastocytoma cells that had been contacted with the test peptide p3 and treated overnight with 50 units per milliliter interferon-gamma. Effector cells (E) and target cells (T) were mixed at different E/T ratios for 4 hours. The specific lysis was determined by the following formula: [(experimental release−spontaneous release)/(maximal release−spontaneous release)]×100. The results are illustrated in FIG. 3B, which shows that immunization with p3 in the presence of the co-stimulatory peptide OVAp was able to induce a CTL response in BALB/c mice that was cytotoxic to the p3-treated P815 target cells; this CTL response was augmented by delivery of the peptides in liposomes. Immunization with the test peptide p3 alone, or with the co-stimulatory peptide OVAp in liposomes, did not induce a substantial CTL-response in BALB/c mice against the target cells; delivery of p3 in liposomes also amplified the CTL response relative to that seen with p3 alone.

Induction of an IgE-specific cytotoxic T-lymphocyte response may depend on T cell co-stimulation. In the particular case of the test peptide p3, p3 alone did not induce a significant IgE-specific cytotoxic T-lymphocyte response in BALB/c adult mice. However, this test peptide was rendered immunogenic by providing a co-stimulatory factor (OVAp or OVAp entrapped in liposomes). An increased IgE-specific cytotoxic T-lymphocyte response was observed in mice immunized with p3 delivered with OVAp in liposomes. The cytotoxic T-lymphocyte response was shown to be specific for immunoglobulin E peptides since immunization with the co-stimulatory factor OVAp in liposomes alone did not elicit IgE-specific cytotoxic T-lymphocytes. The amplified IgE-specific cytotoxic T-lymphocyte response (shown by higher chromium release levels) was noted for the test peptide p3 relative to the test peptides p1 and p2. This may be due to an increased immunogenicity of p3, which encompasses both p1 and p2, and to increased stability due to the increased length of p3 relative to p1 or p2.

A fourth test peptide p4 was synthesized and evaluated for the ability to elicit a cytotoxic T-lymphocyte response to naturally processed and presented immunoglobulin E peptides in mice of a different murine MHC-I haplotype. The test peptide p4 was a 17-mer peptide consisting of the overlapped nonameric amino acid sequences of the test peptides p1 and p2, with an N-terminus two amino acid extension, and a C-terminus two amino acid extension (FIG. 4). The amino acid sequence of p4 was thus: Ile Gln Leu Tyr Cys Phe Ile Try Gly His Ile Leu Asn Asp Val Ser Val (SEQ ID NO. 5).

Figure 6:
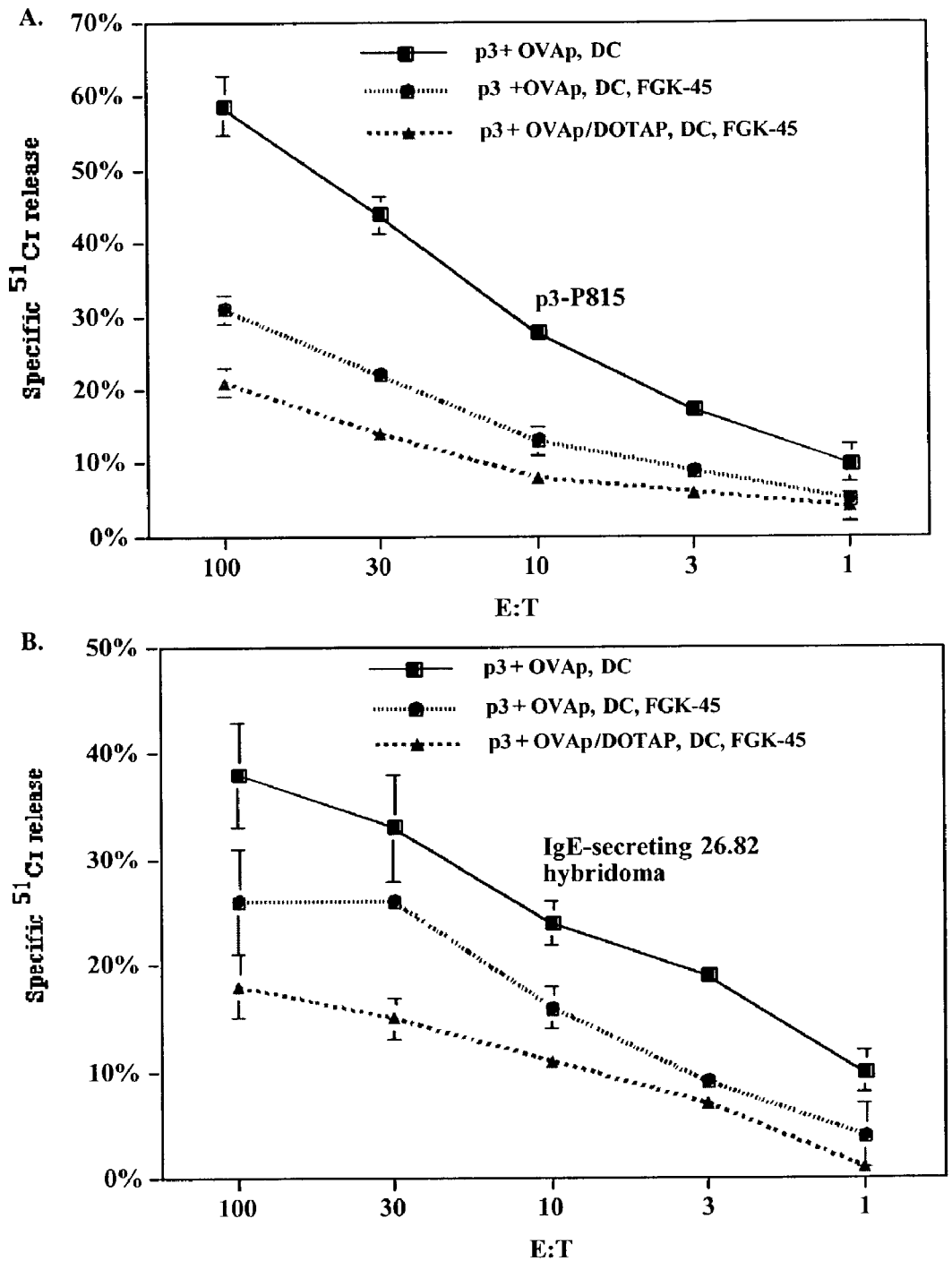
FIG. 6 depicts results of a standard chromium release assay using effector (E) cells at the indicated ratios to target (T) cells. Values shown are means of triplicate cultures with error bars indicating the standard deviation. Effector cells were cytotoxic T-lymphocytes obtained from BALB/c mice (murine MHC-I haplotype H$2^d$) that had been immunized with $2 \times 10^4$ syngeneic bone marrow-derived dendritic cells (DC) (treated as described above with p3 and OVAp), and then treated or not in vivo with the anti-murine CD40 antibody FGK-45.

It was previously reported (Billeta et al., 1995, *Eur. J. Immunol.*, 25:776) that antibodies engineered to express major histocompatibility complex class I- or class II-restricted epitopes in the complementarity-determining regions are naturally processed and presented to T-lymphocytes. The immunogenicity of the test peptide p4 as an isolated peptide was compared to the p4 amino acid sequence engineered into a polypeptide framework (specifically, the p4 amino acid sequence embedded in a loop of an immunoglobulin variable domain). Since an antibody molecule has a much longer half-life than short synthetic peptides and can target antigen-presenting cells via the Fc receptor, such a larger test peptide could be more immunogenic. The murine immunoglobulin E heavy (H) chain gene VH62 was engineered to encode the amino acid sequence of the test peptide p4 into the complementarity-determining region 3 (CDR3) of the immunoglobulin heavy chain framework to yield the fifth test peptide p5. This engineered p5 sequence was cloned into a human IgG1 expression vector and expressed in murine J558L cells as an antigenized antibody composed of the chimeric (mouse/human) H chain associated with the murine lambda 2 light chain. Thus, the length of the test peptide p5 (as the engineered immunoglobulin E heavy chain) exceeds 440 amino acids, and approximates the entire length of an immunoglobulin E heavy chain (Zanetti, U.S. Pat. No. 5,583,202). As the expressed, fully assembled antigenized antibody, the length of the test peptide p4 exceeds 1,400 amino acids in length (Billetta, 1992, *Immunomethods,* 1:41; Billetta et al., 1995, *Eur. J. Immunol,.* 25:776; Zanetti, U.S. Pat. No. 5,583,202, each of which are incorporated by reference in their entirety, in particular the sequences contained therein).

Groups consisting each of five C57BL/6 mice were immunized with either 30 micrograms of the test peptide p4 with 30 micrograms of the co-stimulatory factor OVAp, or with 30 micrograms of the test peptide p5 delivered in 30 micrograms DOTAP liposomes. Two weeks after the first immunization, mice in each respective group were immunized a second time with the appropriate test peptide formulation (p4 plus OVAp, or p5 in DOTAP liposomes) that had been used in the initial immunization. Two weeks after the second immunization, $5\times10^6$ spleen cells were removed from a pool of two to four mice, established in vitro, and re-stimulated with the appropriate test peptide (p4 or p5) in vitro for seven days. The cytotoxic T-lymphocytes thus obtained were tested using a standard chromium release assay for their ability as effector cells to lyse target cells. The target cells consisted of murine EL-4 lymphoma cells, which display the major histocompatibility complex class I molecules H-2$K^b$ and H-2$D^b$, and that had been contacted with the test peptide p4 and treated overnight with 50 units per milliliter interferon-gamma. Effector cells (E) and target cells (T) were mixed at different E/T ratios for 4 hours. The specific lysis was determined by the following formula: [(experimental release−spontaneous release)/(maximal release−spontaneous release)]×100. The results are depicted in FIG. 5, which shows that mice immunized with either of the test peptides p4 or p5 developed comparable levels of immunoglobulin E-specific CTL response. This demonstrated that p5 had been efficiently internalized into antigen-presenting cells, naturally processed and presented through the exogenous major histocompatibility complex class I pathway to yield immunogenic p4-derived peptide-MHC-I molecule complexes.

Example 2

Induction of an Immunoglobulin E-specific, Major Histocompatibility Complex Class I-restricted Cytotoxic T-lymphocyte Response by Antigen-presenting Cells The following example describes the use of antigen-presenting cells to elicit a cytotoxic T-lymphocyte response to naturally processed and presented immunoglobulin E peptides, resulting in a decrease in level of immunoglobulin E-producing cells.

Murine bone marrow-derived dendritic cells were prepared by culturing femur bone marrow cells in the presence of 1.5 nanograms per milliliter recombinant granulocyte macrophage colony stimulating factor (GM-CSF) by a method of Inaba (Inaba, 1990, *J. Exp. Med.,* 172:631). The dendritic cells (DC) were cultured over a period of 10 days following a routine decanting procedure, and the purity of the cell preparation was determined using a monoclonal antibody against CD11c to be greater than 90%. These dendritic cells ($1\times10^6$ in 0.2 milliliter) were pulsed with 100 micrograms of the test peptide p3 together with 30 micrograms of the co-stimulatory factor OVAp (OVAP sequences are restricted to both $IA^d$ and $IA^b$), with or without 30 micrograms DOTAP liposomes for 1 hour at 37° C. Unbound p3, OVAp, and liposomes were removed by washing. The dendritic cells thus treated with p3 as an immunogenic peptide were then used to immunize mice.

BALB/c mice, which display the major histocompatibility complex class I haplotype H2d, were used. Each mouse in a group of four adult BALB/c mice was immunized with $2\times10^4$ dendritic cells (treated as described above with p3 and OVAP), injected equally via the subcutaneous and intraperitoneal routes. Two weeks after the second immunization, $5\times10^6$ spleen cells were removed from a pool of two to four mice, established in vitro, and re-stimulated with the test peptide p3 in vitro for seven days. The cytotoxic T-lymphocytes thus obtained were tested using a standard chromium release assay for their ability as effector cells to lyse target cells. Two types of target cells were used. The first target cell type consisted of P815 murine mastocytoma cells that had been contacted with the test peptide p3 and treated overnight with 50 units per milliliter interferon-gamma (FIG. 6A). The second target cell type consisted of 26.82 hybridomas, which endogenously synthesize and naturally process and present murine immunoglobulin E associated with the major histocompatibility complex class I molecule H-2d (FIG. 6B). Effector cells (E) and target cells (T) were mixed at different E/T ratios for 4 hours. The specific lysis was determined by the following formula: [(experimental release−spontaneous release)/(maximal release−spontaneous release)]×100. Comparable levels of lysis were observed for p3-contacted P815 (FIG. 4A) and for the naturally processed and presented IgE peptide-decorated 26.82 hybridoma cells (Liu, 1980, *J. Immunol.*, 124:2728) (FIG. 6B).

These results demonstrate that the test peptide p3 served as an immunogenic peptide when presented by antigen-presenting cells (dendritic cells that recognize p3) and were able to elicit in the DC-immunized mice a cytotoxic T-lymphocyte response to naturally processed and presented immunoglobulin E peptides. Dendritic cells incubated with p3 and OVAp were sufficient for inducing this CTL response. The magnitude of this CTL response was not amplified by either: (a) in vivo treatment of the DC-immunized mice with the anti-murine CD40 antibody FGK-45 (Schoenberger et al., 1998, *Nature*, 393:480) (24 hours after DC immunization), or (b) incubation of the dendritic cells with p3 and OVAp with DOTAP liposomes. This indicates that the cytotoxic T-lymphocyte response achieved by dendritic cells incubated with p3 and OVAp alone was at or near a ceiling.

Example 3

Breaking Self-tolerance to Natural Immunoglobulin E Peptides.

The following example describes the breaking self-tolerance to natural immunoglobulin E peptides.

In this example, the effect of self-tolerance on induction of a cytotoxic T-lymphocyte response against immunoglobulin E was assessed. A "self" immunoglobulin E peptide would tend to be considered less immunogenic in a mammal that expresses its own (self) immunoglobulin E molecules, due to the phenomenon known as self-tolerance. This example also assessed whether any type of stimulation is critically required to overcome unresponsiveness due to self-tolerance. The magnitude of the cytotoxic T-lymphocyte response against immunoglobulin E in wild-type mice (IgE+/+) that express immunoglobulin E and in mice whose immunoglobulin E gene is deficient (IgE-/-) was compared. Any CTL response against "self" immunoglobulin E induced in IgE+/+ mice would represent a partial response, depending on the strength of T-lymphocyte co-stimulation. If co-stimulation reaches a supra-optimal ceiling, these two genetically disparate mouse strains should exhibit a similar magnitude of cytotoxic T-lymphocyte response following co-stimulation.

Furthermore, since the pertinent targets for therapeutic purposes are cells that express naturally processed and presented immunoglobulin E peptides, immunoglobulin E-producing cells were employed as targets. In these cells, immunoglobulin E peptides are naturally processed and presented by a MHC-I molecule in a physiological, MHC-I-restricted manner.

The 129 strain of mouse, which displays the major histocompatibility complex class I haplotype $H2^b$, was used. Mice carrying the wild-type immunoglobulin E gene (129/SvEv, IgE+/+) and immunoglobulin E gene-deficient mice (129/SvEv, IgE-/-) were equally immunized according to five different regimens, which tested different modes of co-stimulation:

(a) Mice were immunized with 30 micrograms of the test peptide p3, 30 micrograms of the co-stimulatory factor OVAp, and 30 micrograms DOTAP liposomes, in a total volume of 150 microliters, injected equally via the subcutaneous and intraperitoneal routes; 24 hours after immunization, the mice were further injected intravenously with 100 micrograms of the anti-CD40 antibody FGK-45;

(b) Mice were immunized with 30 micrograms of the test peptide p3, 30 micrograms of the co-stimulatory factor OVAp, and 30 micrograms DOTAP liposomes, in a total volume of 150 microliters, injected equally via the subcutaneous and intraperitoneal routes; 24 hours after immunization, the mice were further injected intravenously with 100 micrograms of the normal rat immunoglobulin G2a (IgG2a) as a control for the anti-CD40 antibody treatment;

(c) Mice were immunized with $2 \times 10^4$ dendritic cells (treated with p3 and OVAp as described above in Example 2), injected equally via the subcutaneous and intraperitoneal routes;

(d) Mice were immunized with $2 \times 10^4$ dendritic cells (treated with p3 and OVAp as described above in Example 2), injected equally via the subcutaneous and intraperitoneal routes; 24 hours after immunization, the mice were further injected intravenously with 100 micrograms of the anti-CD40 antibody FGK-45; and (e) Mice were immunized with $2 \times 10^4$ dendritic cells (treated with p3, OVAp, and DOTAP liposomes as described above in Example 2), injected equally via the subcutaneous and intraperitoneal routes; 24 hours after immunization, the mice were further injected intravenously with 100 micrograms of the anti-CD40 antibody FGK-45.

Two weeks after the first immunization, each group of mice was immunized a second time using the formulation as in the first immunization. Two weeks to four weeks after the second immunization, $5 \times 10^6$ spleen cells were removed from a pool of two to four mice, established in vitro, and re-stimulated with the test peptide p3 in vitro for seven days. The cytotoxic T-lymphocytes thus obtained were tested using a standard chromium release assay for their ability as effector cells to lyse target cells. Three types of target cells were used. The first target cell type consisted of murine immunoglobulin E-secreting B4 hybridoma cells, which exhibit the major histocompatibility class I molecule $H-2^b$ (FIG. 7A and FIG. 7C). The second target cell type consisted of murine EL-4 lymphoma cells, which display the major histocompatibility complex class I molecule $H-2^b$ and had been contacted with the test peptide p3 and treated overnight with 50 units per milliliter interferon-gamma (FIG. 7B). The third target cell type consisted of 26.82 hybridomas, which endogenously synthesize and naturally process and present murine immunoglobulin E associated with the major histocompatibility complex class I molecule $H-2^d$ (FIG. 7D). Effector cells (E) and target cells (T) were mixed at different E/T ratios for 4 hours. The specific lysis was determined by the following formula: [(experimental release–spontaneous release)/(maximal release–spontaneous release)]×100. The results are shown in FIG. 7A-FIG. 7D.

An immunoglobulin E peptide-specific CTL response was observed in 129/SvEv, IgE-/- mice immunized with the test peptide p3 together with the co-stimulatory factor OVAp in DOTAP liposomes, or with dendritic cells treated with p3 and OVAp. Cytotoxic T-lymphocytes from these IgE-/- mice were able to lyse target cells that naturally processed and presented immunoglobulin E peptides bound to $H-2^b$, regardless of whether the IgE peptides were biosynthesized endogenously (as in the B4 hybridoma cells, FIG. 7A) or were introduced exogenously (as in the EL-4 lymphoma cells, FIG. 7B).

A similar immunoglobulin E peptide-specific CTL response was observed in 129/SvEv, IgE+/+ mice immunized with the test peptide p3 together with the co-stimulatory factor OVAp in DOTAP liposomes, or with dendritic cells treated with p3 and OVAp. That this CTL response was specific for immunoglobulin E peptides bound to a specific MHC-I haplotype is shown because these cytotoxic T-lymphocytes were able to lyse B4 hybridoma cells (which have the H-$2^b$ haplotype) (FIG. 7C) but not 26.82 hybridoma cells (which have the H-$2^d$ haplotype) (FIG. 7D). Conversely, CTL raised in p3-immunized BALB/c mice (which have the H-$2^d$ haplotype), were able to lyse IgE-secreting 26.82 hybridoma cells (see Example 2). These results show that even though the test peptide p3 was able to induce an IgE-specific response in both H-$2^b$ and H-$2^d$ haplotypes, p3-specific cytotoxic T-lymphocytes induced in the H-$2^b$ environment lyse only IgE producing B4 (H-$2^b$ haplotype) (Rudolph et al., 1981, *Eur. J. Immunol.*, 11:527) but not 26.82 hybridomas (H-$2^d$ haplotype). Thus, MHC-I-restriction of the CTL response is observed at both the inductive phase and effector phase.

Three additional observations were noted. Firstly, the degree of lysis of B4 hybridoma cells by CTL from 129/SvEv, IgE+/+ mice was comparable to that seen for CTL from equivalently immunized 129/SvEv, IgE-/- mice. This shows that immunization methods using different modes of co-stimulation were sufficient to overcome tolerance to self-IgE peptides in the IgE+/+ mice. Secondly, the levels of target cell lysis were similar for CTL responses induced either by immunization with the test peptide p3 together with the co-stimulatory factor OVAp in DOTAP liposomes, or by immunization with dendritic cells treated with p3 and OVAp. Immunoglobulin E test peptides, processed and presented by dendritic cells, are thus at least similar if not identical to endogenously produced, naturally processed and presented IgE peptides that are bound to MHC-I of IgE-secreting plasma cells. Finally, the CTL response induced by dendritic cell immunization was not appreciably amplified by treatment with anti-CD40 antibody. Collectively, these observations show that self-tolerance to the IgE constant region epitopes contained in the test peptide p3 can be fully overcome by appropriate immunization methods. This shows the feasibility of developing a vaccine that is efficacious in eliciting a cytotoxic T-lymphocyte response to endogenously produced, naturally processed and presented IgE in humans or in animals of domestic or economic importance.

Example 4

Inhibition of Immunoglobulin E Production in vitro and in vivo by Immunoglobulin E-specific Cytotoxic T-lymphocytes The following example describes the inhibition of immunoglobulin E production in vitro and in vivo by immunoglobulin E-specific cytotoxic T-lymphocytes.

To determine whether cytotoxic T-lymphocytes elicited by immunoglobulin E peptide immunization could decrease immunoglobulin E production, in vitro stimulated cytotoxic T-lymphocytes were added to IgE-secreting hybridomas or to B-lymphocytes in vitro. In the first experiment, adult BALB/c (H-$2^d$ haplotype) mice (5 per group) were immunized twice with the test peptide p3 together with the co-stimulatory factor OVAp in DOTAP liposomes and their spleen cells re-stimulated in vitro as described in the previous examples. The resulting cytotoxic T-lymphocytes were tested for the ability to lyse immunoglobulin E-secreting target cells, which were either 26.82 hybridoma cells (which have the H-$2^d$ haplotype) or B4 hybridoma cells (which have the H-$2^b$ haplotype), at an E/T ratio of 30 to 1. Immunoglobulin E levels in the cell culture supernatants were determined using a commercial double-sandwich ELISA assay (catalogue number 2655KI, PharMingen). The results are provided in FIG. 8A, which shows that the cytotoxic T-lymphocytes elicited by p3 immunization of H-$2^d$ haplotype mice decreased immunoglobulin E production by H-$2^d$ haplotypic immunoglobulin E-secreting cells (26.82 hybridoma cells) but did not decrease IgE production by H-$2^b$ haplotypic immunoglobulin E-secreting cells (B4 hybridoma cells).

In a second experiment, BALB/c splenic B-lymphocytes were enriched by magnetic beads coated with an antibody against the B-lymphocyte-specific cell surface antigen B220. To assess CTL effects on polyclonal IgE production, $3 \times 10^5$ normal B-lymphocytes were added to either $3 \times 10^6$ p3-activated spleen cells from mice immunized with test peptide p3 together with the co-stimulatory factor OVAp in DOTAP liposomes, or to $3 \times 10^6$ p3-activated spleen cells from mice immunized with only the co-stimulatory factor OVAp in DOTAP liposomes as a control. The co-cultures were then stimulated with 20 micrograms per milliliter lipopolysaccharide (LPS) and 250 units per milliliter murine recombinant interleukin-4 (IL-4). Two days later, the culture supernatants were harvested. Immunoglobulin E levels were determined using a commercial double-sandwich ELISA assay (catalogue number 2655KI, PharMingen). As depicted in FIG. 8B, polyclonal immunoglobulin E production was observed in LPS and IL-4 stimulated B-lymphocyte cultures. Cytotoxic T-lymphocytes from the p3-immunized mice markedly inhibited (71 to 83% inhibition) immunoglobulin E production in vitro (22 versus 75 nanograms per milliliter; 12 versus 72 nanograms per milliliter), whereas cytotoxic T-lymphocytes obtained from the mice immunized with only OVAp as a control did not decrease immunoglobulin E production.

In a third experiment, the effect of immunoglobulin E peptide immunization on production of allergen-specific IgE in vivo was determined. Adult BALB/c mice (5/group) were immunized twice with either the test peptide p3 or the test peptide p1, together with the co-stimulatory factor OVAp in DOTAP liposomes, or with only the co-stimulatory factor OVAp in DOTAP liposomes. Mice immunized with saline served as control. Seven days after the second immunization, mice were challenged with 1 microgram keyhole limpet hemocyanin (KLH) in 2 milligrams alum intraperitoneally four times at a 10 day interval, and the allergen-specific (KLH-specific) IgE in pooled blood was then determined by passive cutaneous anaphylaxis (PCA) reaction. As depicted in FIG. 8C, allergen-specific (KLH-specific) IgE production was significantly ($p<0.01$) inhibited both in mice immunized with p3 and OVAp in liposomes and in mice immunized with the test peptide p1 and OVAp in liposomes (PCA=20). In contrast, mice immunized either with only the co-stimulatory factor OVAp in liposomes or with saline exhibited relatively high titer anti-KLH IgE (PCA=160 and PCA=320, respectively). Reduction of allergen-specific PCA correlated directly with the elicitation of IgE peptide-specific cytotoxic T-lymphocytes in vitro (as depicted in FIG. 3B). Immunoglobulin G (IgG) responses in IgE peptide-vaccinated animals remained comparable to controls.

In vitro and in vivo experiments to determine the efficacy of human MHC-I-specific IgE peptide immunization on production of a human immunoglobulin E-specific cytotoxic T-lymphocyte response can be carried out in a manner similar to that used above, using a human MHC-I molecule such as a specific HLA haplotype. The human immunoglobulin E peptide-specific cytotoxic T-lymphocytes may be prepared ex vivo, for example, using human peripheral blood lymphocytes. The efficacy of immunization with a given immunoglobulin E peptide in producing a human immunoglobulin E-specific cytotoxic T-lymphocyte response can be monitored by measuring levels of immunoglobulin E in the patient (using, for example, ELISAs for human immunoglobulin E), by measuring levels of mediators (such as histamine or leukotrienes) or by monitoring symptoms of allergic disease (such as the severity of atopic dermatitis or atopic rhinitis). This approach is advantageous because it permits the tailoring of the immunoglobulin E vaccination to an individual MHC-I haplotype profile.

Example 5

Methods for Determining Therapeutically or Prophylactically Effective Immunoglobulin E Peptides with Motifs for Major Histocompatibility Complex Class I Molecules in Humans and Other Mammals The following example describes methods for determining therapeutically or prophylactically effective immunoglobulin E peptides with motifs for major histocompatibility complex class I molecules in humans and other mammals.

Four non-limiting examples of approaches for determining natural IgE peptides specific for a given mammalian MHC-I haplotype are illustrated and are provided below.

Approach 1: Direct Immunization of a Mammal with a Test Peptide Predicted by an Algorithm to Bind to an MHC-I Molecule Expressed on a Cell Surface In Vivo by That Mammal.

Algorithms for predicting the binding of a peptide to a given major histocompatibility complex class I molecule, or that predict within a supplied peptide sequence epitopes that bind to a given MHC-I molecule, are publicly available, for example, on the world wide web at bimas.dcrt.nih.gov/molbio/hla_bind/index.html, hiv.basic.nwu.edu/HLA/MotifScanner.cfm, and uni-tuebingen.de/uni/kxi/ or syfpeithi.de. Test peptide sequences, derived from immunoglobulin E from a particular mammalian species, are subjected to the algorithm for the desired MHC-I molecule. "Derived from" refers to having an amino acid sequence based at least partially on the linear sequence of the polypeptide (such as immunoglobulin B) from which the test peptide is derived; amino acid substitutions, deletions, or additions can be incorporated. Amino acids that commonly occur in nature, or that rarely or do not occur in nature, can be incorporated. All L-amino acids, all D-amino acids, or a mixture of L- and D-amino acids can be incorporated. Peptides can be additionally modified, and can be optionally labelled with a detectable moiety, as described herein. The test peptides showing the highest scores for the algorithm, and thus predicted to best bind to the MHC-I molecule, will be selected for further investigation. Optionally, test peptides that show medium or low scores for the algorithm may also be selected for further investigation. This approach has been taken and has proven productive in the mouse, as demonstrated in Example 1. This direct approach requires that the mammals to be immunized with the test peptide express on cell surfaces the desired MHC-I molecule, either endogenously or exogenously (as a transgene). The binding assays may be carried out in vivo or ex vivo, or in vitro on cells such as primary cell lines derived from the mammal. A large breeding animal facility may be required for performing one-step screening and ascertainment of the natural IgE peptides.

Approach 2: Direct Binding of a Test Peptide to an MHC-I Molecule.

The binding of a peptide to a particular major histocompatibility complex class I molecule haplotype can be achieved via a direct binding assay. This may be done by at least two different methods.

The first method includes the following steps:

(i) The desired major histocompatibility complex class I molecule is isolated, for example, from the mammal, from an appropriate cell line, or by recombinant expression of the MHC-I gene. Recombinant expression of the MHC-I gene may be carried out on any somatic cell, as somatic cells constitutively express MHC-I genes. The full-length cDNA for an MHC-I gene can be isolated by polymerase chain reaction (PCR) techniques from the total messenger RNA by employing primers flanking the gene. The protein encoded by the isolated gene can then be produced in relatively large quantities and isolated by affinity chromatography. In practice, the major histocompatibility complex class I molecule to be used in a direct binding assay comprises an isolated MHC-I Moiety. This MHC-I Moiety can be for example a native protein (for example, an isolated intact major histocompatibility complex class I molecule), a complexed protein (for example, an MHC-I molecule complexed with beta-2 microglobulin, or an major histocompatibility complex class I molecule that is non-covalently bound to avidin), or an engineered protein (for example, a chimeric protein consisting in part of an major histocompatibility complex class I molecule), or active fragment thereof, so long as the MHC-I binding site is present and available for binding by the test peptide.

(ii) Test peptides are produced and are optionally labelled with a detectable moiety. Peptides suitable for a direct binding assay are oligopeptides of between about 8 and 17 amino acids in length, although longer or shorter peptides may be used. Any suitable means of producing the peptide may be used. Examples of production means include but are not limited to: isolation from a natural biological source, conventional organic chemical synthesis; combinatorial synthesis using conventional organic chemistry techniques or biocatalysis or both; recombinant expression; and directed evolution methods such as but not limited to phage, ribosome, yeast, and bacterial surface display. Any suitable detectable moiety that renders the test peptide detectable may be used as described herein. Such detectable moieties may be directly attached to the test peptide, or attached through a linker, or attached by non-covalent methods as are known in the art.

(iii) The binding affinity of the test peptide for the major histocompatibility complex class I molecule is determined by methods described herein or as are known in the art. For example, the equilibrium dissociation constant $K_d$ is calculated from measuring labelled test peptide that directly binds to the major histocompatibility complex class I molecule. As one alternative, unlabelled test peptide is competed with the corresponding labelled test peptide for binding to the major histocompatibility complex class I molecule. The binding affinity of each test peptide to the MHC-I molecule is calculated from the inhibition concentrations ($IC_{50}$). As another alternative, the on rate and off rate of unlabelled test peptide binding to the major histocompatibility complex class I molecule can be measured by surface plasmon resonance (SPR) techniques. The binding affinity profile thus obtained may be compared to that obtained by a predictive algorithm.

(iv) Induction of cytotoxic T-lymphocyte response to naturally processed and presented immunoglobulin E peptides is evaluated for test peptides of different affinities.

Approach 3: Test Peptide-induced Cell Surface Expression of MHC-I Molecules.

The stable expression at the cell surface of a major histocompatibility complex class I molecule as part of a properly assembled MHC-I/peptide complex requires that the MHC-I molecule binds a suitable peptide (Pamer & Cresswell, 1998, Annu. Rev. Immunol., 16:323; Shatri et al., 2002, Annu. Rev. Immunol., 20:463). Peptides associated with MHC-I molecules are predominantly generated by proteasome degradation of cytosolic proteins, followed by translocation of the resulting peptides into the endoplasmic reticulum by the transporter associated with antigen processing (TAP) protein.

This approach utilizes cells that are defective in expression of TAP proteins and thus do not stably express major histocompatibility complex class I molecules at their surface. Cell surface expression of the major histocompatibility complex class I molecule can be phenotypically corrected by incubating the defective cells with test peptides that bind to the MHC-I molecule. An example of a suitable defective cell line is the murine TAP1- and TAP2-deficient lymphoma, RMA-S, which is a cell line derived from mice displaying the $H-2^b$ haplotype (De Bruijn, 1991, Eur. J. Immunol., 21:2963). Another suitable defective cell line is the human cell line T2, which displays the MHC-I molecule human leukocyte antigen A2.1 (HLA-A2.1), and is similarly defective in TAP1 and TAP2 expression (Pamer & Cresswell, 1998, Annu. Rev. Immunol., 16:323; Shatri et al, 2002, Annu. Rev. Immunol., 20:463). RMA-S and T2 cells fail to express, respectively, $H-2^d$ or HLA-A2.1, on the cell surface. In the case of RMA-S cells, $H-2^b$ cell surface expression can be corrected by incubating the cells with $H-2K^b$ and $H-2D^b$ specific test peptides. An exogenous MHC-I gene can also be introduced into RMA-S cells, and the resulting engineered cells used in the identification of peptides that bind to the exogenous MHC-I molecule. For example, a desired haplotype of the human MHC-I molecules HLA-A, HLA-B, or HLA-C can be engineered as an exogenous gene into the murine RMA-S cells (Theobald et al., 1997, J. Exp Med., 185:833). Incubating the engineered cells with test peptides that bind specifically to the exogenous MHC-I molecule can induce cell surface expression of the exogenous MHC-I molecule.

Test peptides, each including an amino acid sequence derived from any of the CR1, CH2, CH3, or CR4 domains, or from the membrane exons, of human immunoglobulin E heavy chain, and that are predicted to bind to the human major histocompatibility complex class I molecule HLA-A2.1, were produced. The HLA-A2.1 haplotype is a subtype that encompasses about 95% of the HLA-A2 allele, which is itself expressed in about one-third of the Caucasian population of the U.S. (Mori et al., 2002, electronic publication publicly available on the world wide web at ashi-hla.org/publication-files/archives/prepr/motomi.htm, ashi-hla.org/publication-files/archives/prepr/mori_gf.htm, ashi-hla.org/publication-files/archives/prepr/mori_ab.htm, and ashi-hla.org/publicationtiles/archives/prepr/mori_abd.htm).

The test peptides are chosen from nonameric sequences predicted by the algorithm for peptide binding to HLA-A2.1, using software publicly available on the website bimas.dcrt-.nih.gov/molbio/hla_bind/index.html. This software is provided by the BioInformatics & Molecular Analysis Section (BIMAS), Computational Bioscience and Engineering Lab, Center for Information Technology, National Institutes of Health. To date, about 180 binding motifs are known for the human MHC-I molecules HLA-A, HLA-B, and HLA-C (see for example, hiv.basic.nwu.edu/HLA/Reports/DoMotifList.cfm), and a similar analysis can be performed for any of the haplotypes for which the binding motif and algorithm is available.

A 428 amino acid sequence of human immunoglobulin E from the human IgE myeloma U266 was submitted to the algorithm for prediction of nonameric peptide sequences that bind to HLA-A2.1. Table I lists resulting nonameric test peptides, ranked according to their predicted half-time of dissociation to HLA-A2.1; only peptides with scores greater than 10 are listed. Details of the algorithm's calculations are publicly available on the website bimas.dcrt.nih.gov/molbio/hla_bind/hla_motif_search_info.html#Sect5.

TABLE I

| Rank | Start position | Domain in Human IgE | Peptide Number | Amino Acid Sequence and Sequence ID Number | Score* |
|---|---|---|---|---|---|
| 1 | 185 | CH2 | 539.11 | Trp Leu Ser Asp Arg Thr Tyr Thr Cys (SEQ ID NO. 6) | 93.6 |
| 2 | 96 | CH1 | 539.12 | Trp Val Asp Asn Lys Thr Phe Ser Vat (SEQ ID NO. 7) | 64.9 |
| 3 | 71 | CH1 | 539.8 | Leu Leu Thr Val Ser Gly Ala Trp Ala (SEQ ID NO. 8) | 46.4 |
| 4 | 365 | CH4 | 539.9 | Gln Leu Pro Asp Ala Arg His Ser Thr (SEQ ID NO. 9) | 30.5 |
| 5 | 3 | CH1 | 539.10 | Thr Gln Ser Pro Ser Val Phe Pro Leu (SEQ ID NO. 10) | 28.8 |
| 6 | 309 | | | Ala Leu Met Arg Ser Thr Thr Lys Thr (SEQ ID NO. 11) | 27.5 |
| 7 | 59 | | | Thr Leu Thr Leu Ser Gly His Tyr Ala (SEQ ID NO. 12) | 27.3 |
| 8 | 54 | | | Thr Leu Pro Ala Thr Thr Leu Thr Leu (SEQ ID NO. 13) | 21.3 |
| 9 | 47 | | | Ser Leu Asn Gly Thr Thr Met Thr Leu (SEQ ID NO. 14) | 21.3 |
| 10 | 61 | | | Thr Leu Ser Gly His Tyr Ala Thr Ile (SEQ ID NO. 15) | 15.6 |
| 11 | 52 | | | Thr Met Thr Leu Pro Ala Thr Thr Leu (SEQ ID NO. 16) | 15.4 |
| 12 | 178 | | | Leu Thr Leu Ser Gln Lys His Trp Leu (SEQ ID NO. 17) | 10.2 |

*estimate of half time of dissociation of the test peptide from HLA-A2.1

Five test peptides (peptide numbers 539.11, 539.12, 539.8, 539.9, and 539.10, representing three of the four CH domains of human IgE) from the panel of 12 high-, moderate-, and low-affinity test peptides shown in Table I were tested in RMA-S-A2.1 cells (murine TAP-deficient RMA-S cells that are engineered to express the human MHC-I HLA-A2.1). In addition, the nonameric peptide Ile Leu Lys Glu Pro Val His Gly Val (SEQ ID NO. 18), which is derived from the human immunodeficiency virus (HIV), was tested as an example of a nonameric HLA-A2.1-specific peptide that is not derived from human IgE. RMA-S-A2.1 cells (about $1 \times 10^6$) were incubated in duplicate cultures in 24-wells at 37° C. overnight with the individual test peptides at a final concentration of 50 micromoles per liter, in the presence or absence of human beta-2 microglobulin. Cells were pooled from the duplicate cultures and about $1 \times 10^6$ cells were incubated with 2 micrograms per milliliter fluorescein isothiocyanate-labelled anti-HLA-A2.1 antibody (catalogue number 32294x, PharMingen) at 4° C. for 30 min. Fluorescence-activated cell sorting (FACS) analysis was performed on a FACScan (Becton-Dickinson). About ten thousand events were collected and analyzed by CELLQuest software (version 1.2.2, BD Biosciences). As depicted in FIG. 9, surface HLA-A2.1 molecules were detectable on RMA-S-A2.1 cells. Increase of HLA-A2.1-specific fluorescence intensity by one log was observed in cultures incubated with any of the five human IgE test peptides tested (FIG. 9A, FIG. 9C, FIG. 9D, FIG. 9E, and FIG. 9F). In contrast, no appreciable, increase of HLA-A2.1-specific fluorescence intensity was detected in cultures incubated with medium alone (FIG. 9I). The increase of HLA-A2.1-specific fluorescence intensity is comparable among the five IgE test peptides, and between the five IgE test peptides and the HIV control peptide (FIG. 9G). The observation that the IgE peptides represent different CH domains of human IgE provides a plurality of therapeutic targets for IgE-specific cytotoxic T-lymphocytes. The addition of exogenous human beta-2 microglobulin did not substantially enhance surface expression of HLA-A2.1 (FIG. 9A versus FIG. 9B; FIG. 9G versus FIG. 9H), providing that these IgE peptides, which were predicted to bind strongly to HLA-A2.1, induced a high or possibly maximal expression of HLA-A2.1 at the cell surface.

Test peptides tested as above in RMA-S-A2.1 cells can be similarly tested in the human TAP-deficient T2 cells for their ability to cause cell surface expression of HLA-A2.1. Test peptides that show concordance in one or both tests of binding to HLA-A2.1 can be subsequently used for immunization experiments, for example in rodents transgenically expressing HLA-A2.1, as a further evaluation of the test peptides' therapeutic or prophylactic activity. The immunogenicity of a particular peptide can reflect its binding and stabilizing capacity for HLA-A2.1. Surface expression of MHC-I molecules is correlated with the ability of a test peptide to bind to the MHC-I molecule in the endoplasmic reticulum and the Golgi apparatus.

The detection of cell surface major histocompatibility complex class I expression by flow cytometric methods, such as fluorescence-activated cell sorting (FACS), and dissociation ($K_d$) measurements, can be configured into a high throughput screen. The induction of cell surface MHC-I expression for test peptides can be titrated over a range, for example between about 0.1 microgram to about 100 micrograms of test peptide per milliliter. The ease of induction can correlate with therapeutic effectiveness in vivo.

Approach 4: Determining a Binding Motif for a Major Histocompatibility Complex Class I Molecule.

At present, binding motifs (and algorithms for binding affinity) are known or characterized for many but not all human and mouse major histocompatibility complex class I molecules. Few or no binding motifs are known for MHC-I molecules specific to mammals of economic importance such as those used in food production (including cattle, swine, sheep, and goats), or for mammals of domestic importance such as those that are common pets (including dogs, cats, horses, ferrets, rats, rabbits, guinea pigs, gerbils, and hamsters). For example, at present, only a few MHC-I binding motifs are known or characterized for cattle, horses, swine, dogs, cats, and rats, and none have been reported or characterized for ferrets, gerbils, and hamsters.

An example of a procedure to determine the binding motif of a specific major histocompatibility complex class I molecule, such as of an uncharacterized or of a characterized MHC-I molecule, uses phage display and includes the following steps:

(i) A combinatory library of test peptides cloned into the PIll or PVIII coat proteins of the bacterial filamentous phage M13 is prepared (Smith, 1985, *Science*, 228:1315).

(ii) The gene encoding the desired major histocompatibility complex class I molecule is cloned by polymerase chain reaction (PCR) techniques from the total messenger RNA (or oligo-dT selected mRNAs) by employing primers flanking the gene. The protein encoded by the isolated gene is produced in relatively large quantities and isolated by affinity chromatography. The isolated MHC-I molecules are biotinylated and immobilized on avidin-coated plates.

(iii) The combinatorial test peptide library is panned on the immobilized MHC-I molecules.

(iv) Phages that bind to the immobilized MHC-I molecules are retained and their displayed test peptides sequenced.

(v) The resulting amino acid sequences are aligned and the frequency of occurrence of individual amino acids is determined at each position of the aptamer.

(vi) These amino acid occurrence frequencies are weighted according to their position in the aptamer, taking into account the major and minor anchor residue positions, and a binding motif is determined.

A second example of a procedure to determine the binding motif of a specific major histocompatibility complex class I molecule, such as of an uncharacterized or of a characterized MHC-I molecule, uses ribosomal display and includes the following steps (He, 1999, *J. Immunol. Methods*, 231:105):

(i) A combinatory library of polynucleotides encoding test peptides cloned into a polypeptide framework was prepared by ribosomal display techniques. Suitable polypeptide frameworks preferably contain at least one exposed loop region that is exposed to the hydrophilic environment, is preferably thermodynamically stable, and preferably can accept insertion of the immunogenic peptide or of the co-stimulatory peptide. Examples of such polypeptide frameworks include green fluorescent protein (GFP), staphylococcal nuclease, fibronectin, immunoglobulin (Ig), and heat shock protein (HSP). The gene encoding the chosen polypeptide framework is prepared by optionally enhancing the transcription start site and translational site for either or both eukayotic and prokaryotic systems. A test peptide aptamer library was prepared using randomized oligonucleotides, cloned into the internal loop region of the polypeptide framework of green fluorescent protein (GFP).

(ii) The gene encoding the desired major histocompatibility complex class I molecule is cloned by polymerase chain reaction (PCR) techniques from the total messenger RNA (or oligo-dT selected mRNAs) by employing primers flanking the gene. The protein encoded by the isolated gene is produced in relatively large quantities and isolated by affinity chromatography. The isolated major histocompatibility complex class I molecules are biotinylated and immobilized on avidin-coated plates.

(iii) The ribosomal display test peptide library is panned on the immobilized MHC-I molecules.

(iv) Aptamers that bind to the immobilized MHC-I molecules are retained and their displayed test peptides sequenced.
(v) The resulting amino acid sequences are aligned and the frequency of occurrence of individual amino acids is determined at each position of the aptamer.
(vi) These amino acid occurrence frequencies are weighted according to their position in the aptamer, taking into account the major and minor anchor residue positions, and a binding motif is determined.

A third example of a procedure to determine the binding motif of a specific MHC-I molecule, such as of an uncharacterized or of a characterized MHC-I molecule, includes the following steps (Falk et al., 1991, *Nature,* 351:290):

(i) A library of test peptides is prepared by combinatorial synthesis. The synthesized peptides vary from 5 to 17 amino acids in length, although longer or shorter peptides can be used.
(ii) The gene encoding the desired MHC-I molecule is cloned by polymerase chain reaction (PCR) techniques from the total messenger RNA (or oligo-dT selected mRNAs) by employing primers flanking the gene. The protein encoded by the isolated gene is produced in relatively large quantities and isolated by affinity chromatography. The isolated MHC-I molecules are biotinylated and immobilized on avidin-coated plates.
(iii) The combinatorially synthesized test peptide library is panned on the immobilized MHC-I molecules.
(iv) Test peptides that bind to the immobilized MHC-I molecules are retained and separated from the unbound test peptides.
(v) The bound test peptides are eluted from the immobilized MHC-I molecules and subjected to pooled peptide sequencing.
(vii) Pooled peptide sequencing reveals strong signals for amino acids at the major binding motif positions, whereas amino acids at variable binding positions occur at low or undetectable frequencies. The obtained amino acid sequences are aligned and an occurrence frequency for an individual amino acid estimated for each position.
(vi) These amino acid occurrence frequencies are weighted according to their position, taking into account the major and minor anchor residue positions, and a binding motif is determined This approach is advantageous because it allows the development of an immunoglobulin E peptide vaccine specific to major histocompatibility complex class I molecules of previously unknown binding specificity.

Example 6

Transgenic Animals and Cells

The following example describes the use of transgenic animals and cells as sources of cytotoxic T-lymphocytes, as sources of target cells, and as models of modulation of immunoglobulin E-mediated conditions.

Transgenic Mice

The therapeutic or prophylactic activity of immunoglobulin E peptides that are specific for an MHC-I molecule and are obtained through approaches such as those described in Example 5, can be further evaluated using a mammal, such as a mouse, that transgenically expresses that particular MHC-1 molecule. In one variant of this approach, a hybrid MHC-1 is prepared that contains the alpha-1 and alpha-2 domains of the particular MHC-1 for binding the test peptide, as well as the alpha-3 domain of the host mammal (for example, a mouse), which permits optimal interaction with CD8 molecules on cytotoxic T-lymphocytes. This hybrid MHC-1, expressed on target cells obtained from the transgenic mammal, can thus bind peptide as well as receive lytic signal from cytotoxic T-lymphocytes via cognate interactions (Minev et al., 2000, *Proc. Natl. Acad. Sci.,* 97:4796; Theobald et al., 1997, *J. Exp Med.,* 185:833). Mice can also be engineered to be doubly transgenic, that is, transgenic for a human MHC-I molecule (HLA haplotype) and transgenic for human immunoglobulin E. The human immunoglobulin E myeloma, U266, is an example of a ready source of rearranged human immunoglobulin E genomic DNA (Neuberger, 1995, *Nature,* 314:268), useful in constructing such transgenic mammals. For example, mice were engineered to transgenically express both human HLA-A2.1 and human immunoglobulin E (heavy chain constant region and membrane domain, fused into the murine VH gene). The resulting animals express human HLA-A2.1 at the cell surface, and produce the chimeric human/murine immunoglobulin E (comprising human IgE heavy chain and the endogenous murine IgE light chain) as well as the endogenous murine IgE. This is illustrated in FIG. 10.

The HLA-A2.1 and human IgE double transgenic mice are a source of HLA-A2.1 haplotypic human IgE-bearing B-lymphocytes and human IgE-secreting plasma cells. These cells are an example of target cells that display naturally processed and presented human immunoglobulin E peptides bound to a particular human major histocompatibility complex class I molecule expressed on the cell surface. The ability of cytotoxic T-lymphocytes to lyse these target cells can be tested in vivo and in vitro. These double transgenic mice also provide a pseudo-natural immunophysiological environment for testing immunoglobulin E peptides for the ability to break self-tolerance.

"Triple feature" mice are a further development of the HLA-A2.1 (Jackson Laboratory, Bar Harbor, Me.) and human immunoglobulin E double transgenic mice described above. These mice are constructed by crossing the double transgenic mice to mice deficient in the murine immunoglobulin E gene (Oettgen et al., 1994, *Nature,* 370:367). The resulting triple feature mice produce only human IgE heavy chain paired with endogenous murine IgE light chain, but no endogenous murine IgE in the HLA-A2.1 environment. These mice are useful for testing immunoglobulin E peptides in a manner similar to the double transgenic mice, and similarly also provide a source of target cells useful for testing cytotoxic T-lymphocytes. Immunoglobulin E production is diminished in the double transgenic or three feature mice in vivo when these mice are immunized with an effectively immunogenic human IgE peptide specific for HLA-A2.1, since the cytotoxic T-lymphocytes elicited in these mice target IgE producing cells.

The target cells (HLA-A2.1 haplotypic human IgE-bearing B-lymphocytes and human IgE-secreting plasma cells) derived from the double transgenic or triple feature mice are also valuable as primary cell lines or as a foundation for permanent cell lines. These derived cell lines are useful for experiments in which the B-lymphocytes are stimulated for immunoglobulin E production, or where the cells serve as naturally processed and presented IgE peptide-displaying target cells for testing in vitro the ability of cytotoxic T-lymphocytes to lyse such target cells.

Illustrative examples of preparing immunoglobulin E cDNA constructs, in a conventional eukaryotic vector and in an adenoviral vector, follow, although other methods are available. Such constructs are useful, for example, for transfecting and producing short-term and long-term IgE-producing cell lines.

One approach of preparing a human IgE gene in a transgenic vector includes the human IgE heavy chain constant region including the CH1, CH2, CH3, and CH4 domains physiologically rearranged with a VH gene of known specificity (Neuberger, 1995, *Nature*, 314:268). Another approach of preparing a human IgE gene in a transgenic vector includes the human IgE heavy chain constant region including the CH1, CH2, CH3, and CH4 domains and membrane exon 1 and exon 2 (Sun et al., 1991, *J. Immunol.*, 146,199; Zhang, 1994, *J. Biol. Chem.*, 269:456), fused with murine IgE heavy chain variable region (VH domain) of a known specificity (Neuberger, 1995, *Nature*, 314:268). The latter construct can be particularly useful for producing transgenic animals that express the membrane anchored exogenous IgE as well as secreted exogenous IgE upon induction by a specific allergen.

In one specific example, illustrated in FIG. 11, the construction of an antigen-specific, mouse/human chimeric huIgE gene including the membrane anchor sequence was performed according to the following steps:
- (i) The genomic DNA was prepared from the human cell line U266. U266 is an IgE-producing myeloma (plasmacytoma) line that displays the HLA-A2.1 haplotype. An 8.5 kb DNA fragment encompassing the IgE heavy chain constant region and membrane domains, plus the enhancer regions and promoter, was amplified by long-range PCR using the primers 5' cctggtggagcgtgagtggcc (SEQ ID NO. 19) (forward direction), and 5' cctccaca-cagagcccatccgtcttc (SEQ ID NO. 20) (reverse direction).
- (ii) The mouse IgE heavy chain variable region (VH), encompassing the 5' regulatory region and a 3' EcoRI restriction site, was amplified from genomic DNA isolated from the nitrophenol-specific (NP-specific) murine cell line JW8. The primers used for PCR were 5' tatagtcgacaccatgggatggagctgtatc (SEQ ID NO. 21) (forward direction), and 5' taccgctgaaggttttgttgtcgac (SEQ ID NO. 22) (reverse direction).
- (iii) The murine IgE VH segment was ligated via the SalI restriction site near the beginning of the human IgE CH1 domain. The resulting chimeric construct was cloned into the modified pUC19 vector, pHSE3', which contains the MHC-I H-2 promoter and immunoglobulin heavy chain enhancer region. The expressed chimeric heavy chain is expected to exhibit anti-NP specificity, and the affinity would be expected to be further improved when chimeric heavy chain is assembled with the IgE lambda-2 light chain (Neuberger, 1995, *Nature*, 314:268; Engel et al., 1998, *Eur. J. Immunol.*, 20:2289).

U266 is also a source of IgE cDNA for preparing IgE-producing cell lines. U266 myelomas express five major species of spliced IgE messages and translated products, including intact membrane IgE and secreted IgE (Batista et al., 1995, *J. Immunol.*, 154:209). Two of the five messages encode IgE lacking a full complement of CH4 and which are not believed to be appreciably secreted, or encode IgE with only partial membrane exon sequences, which are not believed to be appreciably assembled. These IgE isoforms produced in U266 can serve as a rich source of degraded natural IgE peptides, some of which can bind selectively to HLA-A2.1 for presentation on the cell surface as targets of cytotoxic T-lymphocytes. Such peptides are expected to be useful for sustaining the immunosurveillance process by cytotoxic T-lymphocytes that recognize naturally processed and presented IgE peptides generated in situ.

U266 cells were used for the cloning of human immunoglobulin E cDNA isoforms into an adenoviral vector as follows:
- (i) Human immunoglobulin E cDNA was amplified by reverse transcriptase-polymerase chain reaction (RT-PCR) from total RNA isolated from U266 cells. The first strand cDNA was synthesized using random primers and oligo-dT (Gibco). Full-length IgE cDNA was amplified using the following primers: 5'gagagctccgttcctcaccatgg (SEQ ID NO. 23) (forward direction) and 5'cgtcatttac-cgggatttacagacacc (SEQ ID NO. 24) (reverse direction). All IgE isoforms were verified by DNA sequencing. FIG. 12A illustrates the different IgE isoforms cloned in this manner.
- (ii) pSml3, encoding full-length cDNA of human immunoglobulin E membrane long form was cloned into the conventional mammalian expression vector pShuttle (Clontech) using EcoRI/XhoI and the resulting construct used to transfect human kidney 293 cells. Transient expression of the pSml3 insert was confirmed by Western blot (FIG. 13A) using goat anti-human immunoglobulin E IgG (GAHE) as the primary antibody. Rabbit anti-goat IgG antibody, conjugated with horseradish peroxidase (HRP) was used as the secondary antibody. The blot was developed using 3,3',5,5'-tetramethylbenzidine (TMB) (Kirkegaard & Perry Laboratories) as a substrate. The 65 kDa protein species, encoded by full length classical long from IgE in pShuttle was translated in 293 cells (human transformed primary embryonal kidney cells). This transcript substantially conformed to the predicted molecular weight with full membrane-encoded exon sequences.
- (iii) pSml3, encoding full-length cDNA of human immunoglobulin E membrane long form was similarly cloned into the adenoviral vector pAd-lacZ using the Adeno X kit (Clontech). FIG. 12B illustrates the adenoviral IgE construct. The viral stock from primary amplification was subject to SDS-PAGE, and then followed by western blot (FIG. 13B) as described above. In apparent contrast to the results obtained from the conventional mammalian expression vector pShuttle, the heavy chain gene product expressed in adenoviral vector appeared as the same molecular weight but migrated as a broader band, suggesting adequate glycosylation.

Target Cells Employing Cell Lines, Including PBMC in Vitro

Transgenic mice expressing an exogenous MHC-I molecule (for example, the human MHC-I haplotype HLA-A2.1) can be immunized with a selected immunoglobulin E peptide, and the resulting cytotoxic T-lymphocytes subsequently tested for the ability to lyse IgE producing cells and to inhibit IgE production. FIG. 14 illustrates two approaches, each using a different type of target cell.

In the first approach, a cytotoxic T-lymphocyte response specific for immunoglobulin E peptides naturally processed and presented on the MHC-I molecule HLA-A2.1 is generated in mice that have been engineered to transgenically express HLA-A2.1. Cytotoxic T-lymphocytes are prepared from spleens harvested from the immunized mice. The target cells used in this first approach are cells in which the MHC class I molecule is contacted with test peptide exogenously. As shown in FIG. 14A, a specific example of such target cells are TAP deficient RMA-S cells, which transgenically express HLA-A2.1. These target cells are incubated overnight with 10 nanograms to 100 micrograms of individual test peptides (chosen from Table I) in a 10% $CO_2$ incubator. The target cells are then harvested and labelled for 90 minutes with $^{51}Cr$. The peptide-treated, chromium-labelled target cells are serially diluted and added to cytotoxic T-lymphocytes in 96-well plates. After a four-hour incubation at 37° C., supernatants are removed and the chromium release is counted to indicate the extent of cell lysis.

In the second approach, the target cells that are used synthesize immunoglobulin E which is naturally processed and presented as peptides on the major histocompatibility complex class I molecule. FIG. 14B illustrates a specific example of this second approach, in which the target cells are the human immunoglobulin E-producing myeloma U266, which has the HLA-A2.1 haplotype. The U266 subclones SKO-007 and AF-10 maybe similarly used as target cells.

Human peripheral blood mononuclear cells (PBMC), like the U266 cell line, express a range of spliced IgE messages and translated products (Batista et al., 1995, *J. Immunol.*, 154:209). The information obtained by using U266 target cells regarding efficacies of HLA-A2.1-restricted test peptides is therefore relevant for studying efficacies of test peptides in human peripheral blood. IgE-specific cytotoxic cells from HLA-A2.1 transgenic mice, such as those described above, are restricted to human HLA-A2.1, and they will not confer xenogenic reactivities to PBMC exhibiting HLA-A2.1 due to self-tolerance. The methods described herein can be used to inhibit IgE production or to lyse IgE-producing tumor cell lines (such as U266) as well as inhibiting or lysing IgE-producing cells (such as human PBMC cultures following allergen challenges or mitogen challenges in the presence of interleukin-4).

The differentially spliced IgE cDNA constructs such as those described above and illustrated in FIG. 12, cloned into a conventional eukaryotic (mammalian) vector or an adenoviral vector, can be used to transfect an appropriate cell line to yield novel target cells. For example, permanent tumor cell lines of diverse tissue origins including the lymphoid/mycloid lineages are transfected with an IgE cDNA construct. These cell lines can then be further transfected with an exogenous MHC-I gene. The immunoglobulin E peptides generated in these transfected cells are naturally processed and presented by the exogenous MHC-I molecules.

Alternatively, a test primary cell culture or cell line is transfected with an IgE cDNA constructs such as those described above, as well as with an exogenous MHC-I gene. This test cell type is not limited to lymphoid cell types, so long as the transfected cells are capable of synthesizing the exogenous IgE to IgE peptides that are naturally processed and presented by the exogenous MHC-I molecules.

Target Cells Derived from IgE Producing Cells from Double Transgenic Mice

Mice expressing U266-derived IgE transgene (of an unknown VH specificity) are first immunized with IgE peptides, using appropriate co-stimulation (such as helper T-lymphocyte co-stimulatory epitopes). It has previously been shown that immunizing mice with goat antibodies against murine IgD ("GAMD") or with goat antibodies against murine IgE ("GAME") induces polyclonal IgE production in the mice, due to antigenic signals delivered by mature B cells whose surface IgD or IgE is perturbed, as well as to co-stimulation delivered by IL-4-producing Th2 specific for foreign goat IgG determinants (Katona et al., 1991, *J. Immunol,.* 146:4215). The protective effect of immunization with IgE peptides can be evaluated by stimulating polyclonal IgE production in the U266 transgenic mice in vivo with an antigen surrogate such as GAMD or goat anti-human-IgE ("GAHE"). Upon stimulation with an anti-immunoglobulin as the antigen surrogate, mature B-lymphocytes are polyclonally activated and express IgE at high levels. As a result higher levels of naturally processed and presented IgE peptides, such as from the catabolism of IgE in the stimulated B-lymphocytes or plasma cells, are displayed on the surface of these cells. These activated B-lymphocytes and plasma cells generated in vivo are rendered more susceptible to lysis by cytotoxic T-lymphocytes specific for the IgE peptides used in the initial immunization. The downregulation of these IgE producing cells serves as a measurement of the IgE-specific cytotoxic T-lymphocyte response.

To test the effect of cytotoxic T-lymphocytes on normal IgE producing cells in vitro, single splenic cell cultures, prepared from IgE peptide immunized mice are re-stimulated with IgE peptide and appropriate co-stimulation (such as helper T-lymphocyte co-stimulatory epitopes). The activated cytotoxic T-lymphocytes thus obtained are then added to splenic cultures from double transgenic mice, stimulated in vitro with lipopolysacharide (LPS), pokeweed mitogen (PWM), antigen surrogates, or IL-4. Levels of IgE in vitro are then determined.

To test the lysis of target cells in vitro, single cell suspensions are prepared from the spleens of double transgenic mice immunized with IgE peptide as above. The cells are re-stimulated in vitro with the IgE peptide and the co-stimulatory peptide. Activated cytotoxic T-lymphocytes thus obtained are then added in various ratios to $^{51}$Cr-labeled and allergen-activated B-lymphocytes and to 51Cr-labelled and LPS/dextran sulfate-activated B-lymphocytes. The percentage of chromium release of the lysed B-lymphocytes is determined.

Target Cells Derived from NP-specific IgE Transgenic Mice

In contrast to the above transgenic mice which respond to GAME as an antigenic surrogate, transgenic mice that express nitrophenol (NP)-specific chimeric mouse/human IgE respond to nominal antigens or allergens such as nitrophenol conjugated to the carrier proteins keyhole limpet hemocyanin (KLH) or bovine serum albumin (BSA). These NP-specific chimeric IgE transgenic mice can be first immunized with IgE peptides, using appropriate co-stimulation (such as helper T-lymphocyte co-stimulatory epitopes). To determine the protective effect of immunization by the IgE peptides, the immunized mice are subsequently primed with between about 1 to about 100 micrograms NP-KLH, in preferably about 2 mg alum, but other amounts are appropriate, and then challenged with the same or similar antigens in alum. Levels of NP-specific IgE in allergen-challenged mice will be evaluated. High levels of naturally processed and presented IgE peptides are expressed by allergen-activated NP-specific IgE-bearing B-lymphocytes and NP-secreting plasma cells. Consequently, the allergen-activated NP-specific IgE-bearing B-lymphocytes and NP-secreting plasma cells are susceptible to lysis by cytotoxic T-lymphocytes specific for the IgE peptides used in the initial immunization. Inhibition of IgE production in transgenic B-lymphocytes can be a result of the illustrative methods of direct lysis of the B-lymphocytes, of inhibition of IgE production at the transcriptional and/or translational level, of skewing the ratios of normally spliced epsilon messages toward abnormally spliced messages, or of a failure of IgE to be assembled on the cell surface or to be secreted. However, the inventors do not intend to be limited to such illustrative methods or mechanisms.

Mast Cells as Target Cells

Bone marrow-derived mast cells (BMMC) from the double transgenic mice are cultured with interleukin-3 (IL-3), granulocyte/monocyte colony stimulating factor (GM-CSF) (Franji et al., *J. Immunol.*, 151:6318; Chen, 2000, Immunol., 100, 471), and stem cell factor (SCF). BMMC that display naturally processed and presented IgE peptides on HLA-A2.1 can be used as targets for cytotoxic T-lymphocytes using a chromium release assay. Also, secretion of histamine, leukotrienes, and cytokines (such as GM-CSF, IL-4, interferon-gamma, and tumor necrosis factor alpha) is decreased in IgE-sensitized and allergen-challenged mast cells following incubation with cytotoxic-T lymphocytes.

In a variation of this example, BMMC cultured from HLA-A2.1 single transgenic mice, are contacted with IgE whole molecules and allergens. Immunoglobulin E and allergens form IgE-allergen complexes bound to FceRI receptors on the surface of the mast cells. The mast cells are then incubated with IgE peptide-specific cytotoxic T-lymphocytes. A chromium release assay and inhibition of secretion of small molecules and cytokines are measured as above as an indication of the cytotoxic T-lymphocytes' ability to lyse mast cells.

Inhibition of Endogenous Murine IgG Production

Since a majority of B-lymphocytes in the double transgenic mice exhibits the exogenous human IgE as well as the endogenous murine surface immunoglobulins of different isotypes, natural IgE peptide-specific cytotoxic T-lymphocytes are tested for their ability to decrease endogenous murine IgE/IgG production. In contrast, production of chimeric antigen-specific human IgE as well as endogenous murine IgG production will not be affected in mice immunized with helper T-lymphocyte peptide alone. Antigen-specific and total human IgE and murine IgG production is evaluated by ELISA or ELISA plaque assay (Chen, 1990, *J. Immunol. Meth.*, 135:129).

Determining the Optimal Natural Peptides in IgE and HLA Double Transgenic Mice

Mice that are doubly transgenic for human IgE and HLA-A2.1 are an alternative system for testing the "naturalness" of the test peptides such as those obtained in Example 1. Human IgE-specific cytotoxic T-lymphocytes are readily induced in mice transgenic for human IgE, because human IgE peptides are foreign to the murine system. However, such cytotoxic T-lymphocytes may be naturally tolerized in the human population that expresses both huIgE and HLA-A2.1. Like ssomatic antigens, human IgE peptides naturally presented on HLA-A2.1 in transgenic mice are considered "self" antigens by the mice. IgE is a macromolecule and there should be a few natural IgE peptides that can be generated and presented by HLA-A2.1. The double transgenic mice therefore provide a pertinent model as to whether cytotoxic T-lymphocytes for a particular natural IgE peptide can be efficiently induced.

In Example 3, IgE+/+ (wild type) and IgE-/- mice showed approximately the same magnitude of IgE-specific cytotoxic T-lymphocyte response. In the case of the specific IgE peptide used in Example 3, self tolerance does not appear to play a major role in preventing induction of a CTL response. However, it is possible that different degrees of tolerance can exist with respect to a diverse spectrum of IgE natural peptides. For example, a high-affinity IgE peptide that is immunogenic in HLA-A2.1 transgenic mice could cause profound clonal deletion in double transgenic mice. In contrast, an IgE peptide of intermediate binding affinity could induce a response with appropriate modes and levels of co-stimulation. An efficacious IgE peptide vaccine strikes a balance between the IgE peptides' binding affinity and the capacity of the partially tolerant cytotoxic T-lymphocytes to respond to appropriate co-stimulation. An efficacious IgE peptide vaccine candidate can be achieved by striking a balance between the inherent properties of an antigenic epitope and the state of partial tolerance or ignorance of the immune system. This can require that (1) the IgE peptide exhibits moderate to high affinity toward the cytotoxic T-lymphocytes (but not to the extent of causing cloning inactivation of these T-lymphocytes), and (2) maintaining receptiveness of these IgE peptide-specific T-lymphocytes to concomitant T-lymphocyte co-stimulation, so that cytotoxic T-lymphocytes can be induced but are not anergized by encountering high affinity, self antigenic peptides in the absence of adequate co-stimulation. Double-transgenic mice could also serve as a useful pre-clinical animal model for assessment of the immunogenicity and inducibility of a IgE natural peptide as an IgE vaccine for humans.

Managing the IgE-specific Cytotoxic T-lymphocyte Response by Controlling Delivery of Costimulation Maintaining inducibility by T-lymphocyte co-stimulation, or a state of partial tolerance of an immunoglobulin E peptide vaccine, also permits the safety feature that normal levels of IgE can be produced in vaccinated subjects during the seasons when environmental allergens are reduced. Permanent deletion of immunoglobulin E responses is not anticipated, since the IgE peptide-specific cytotoxic T-lymphocyte response is believed to be induced and maintained in the subject when the immunogenic IgE peptide is delivered together with appropriate co-stimulation. The sustainability of an immunoglobulin E peptide antigenic stimulation is believed to be enhanced by cognate T-lymphocyte co-stimulation or by an appropriate antigen-presenting cell such as a dendritic cell. To improve the efficiency of delivering cognate co-stimulation, cytotoxic IgE natural peptides can be provided along with a co-stimulatory peptide (such as a helper T-lymphocyte epitope) in a longer polypeptide framework, or as a product of a mini-gene encoding both the immunogenic IgE peptide and the co-stimulatory peptide. Dendritic cells, which play a role in the in vivo adaptive immune response (Banchereau et al., 1998, *Nature*, 392:245), are a rich source of co-stimulation and are known to render self-peptides immunogenic, that is to say, they are capable of breaking self-tolerance without the need for a foreign or non-self T-lymphocyte helper epitope (Inaba, 1990, *J. Exp. Med.*, 172:631). Tissue distribution of dendritic cells is believed to provide the spreading of immunity, and is believed to protect bodily zones not directly sensitized by antigen (Banchereau et al., 1998, *Nature* 392, 245). Therefore, dendritic cells that have been immunized with IgE peptides, optionally with co-stimulation, are expected to be efficient for breaking tolerance and maintaining the inducibility of the IgE peptide-specific cytotoxic T-lymphocyte response. Cytotoxic T-lymphocytes to natural immunoglobulin E peptides become dormant when uncoupled from the interaction with in vivo administered DC.

Example 7

Immunoglobulin E Sequences as Candidates for Inducing a Cytotoxic T-lymphocyte Response The following example describes examples of nucleic acid and amino acid sequences of immunoglobulin E from various mammalian species, including mammals of economic importance, mammals of domestic importance, non-human primates, and humans, and methods of identifying them, that are useful in the present invention.

The amino acid sequences for immunoglobulin E heavy chain, including complete CH1 to CH4 constant region domains, have been determined for cat (*Felix catus*) (SEQ ID NO. 25) (Weber et al., 2000, *Vet. Immunol. Immunopathol.*, 76:299), chimpanzee (*Pan troglodytes*) (SEQ ID NO. 26)

(Sakoyama et al., 1987, *Proc. Natl. Acad. Sci.*, 84:1080), cow (*Bos taurus*) (SEQ ID NO. 27) (Rabbani et al., 1996, Department of Bioscience at NOVUM, Karolinska Institute, Huddinge S-141 57, Sweden, direct submission to NCBI, accession number gi:1575497), dog (*Canis familiaris*) (SEQ ID NO. 28) (Patel et al., 1995, *Immunogenetics*, 41:282), duck-billed platypus (*Ornithorhynchus anatinus*) (SEQ ID NO. 29) (Aveskogh et al., 2001, Dept. of Cell and Molecular Biology, Uppsala University, BMC, Box 596, Uppsala SE-75124, Sweden, direct submission to NCBI, accession number #gi: 17223803), horse (*Equus caballus*) (SEQ ID NO. 30) (Navarro et al., 1995, *Mol. Immunol.*, 32:1), mouse (*Mus musculus*) (SEQ ID NO. 31) (Nikaido et al., 1982, *J. Biol. Chem.*, 257:7322), opossum (*Monodelphis domestica*) (SEQ ID NO. 32) (Aveskogh et al., 1998, *Eur. J. Immunol.*, 28:2738), pig (*Sus scrofa*) (SEQ ID NO. 33) (Vernersson et al., 1997, *Immunogenetics*, 46:461), rat (*Rattus norvegicus*) (SEQ ID NO. 34) (Kindsvogel et al., 1982, *DNA*, 1:335), sheep (*Ovis aries*) (SEQ ID NO. 35) (Engwerda et al., 1992, *Vet. Immunol. Immunopathol.*, 34:115), brushtail possum (*Trichosurus vulpecula*) (SEQ ID NO. 36) (Belov et al., 1999, *Mol. Immunol.*, 36:1255), and human (*Homo sapiens*) (SEQ ID NO. 37) (Kenton et al., 1982, *Proc. Natl. Acad. Sci.*, 79:6661). The amino acid sequences for immunoglobulin E heavy chain variable region (VH) have also been partially determined for cat (SEQ ID NO. 25), and completely determined for *Ornithorhynchus anatinus* (duckbilled platypus) (SEQ ID NO. 29), horse (SEQ ID NO. 30), pig (SEQ ID NO. 33), sheep (SEQ ID NO. 35), and human (SEQ ID NO. 37). The amino acid alignment of the IgE heavy chain sequences for human, sheep, rat, pig, mouse, horse, duck, dog, cow, chimpanzee, and cat is depicted in FIG. 15A, FIG. 15B, FIG. 15C, and FIG. 15D, which show sequence homology of 60% or more between IgE from different species.

A phylogenetic tree, depicted in FIG. 16, representing the inferred evolutionary divergence between the immunoglobulin E heavy chain polypeptides of human, sheep, rat, pig, mouse, horse, duck, dog, cow, chimpanzee, Trichosurus (brushtail possum), and cat, was calculated from the above sequences using the progressive multiple sequence alignment program ClustalW (Higgins et al., 1994, *Nucleic Acids Res.*, 22:4673). This approach uses two-stage computation, that is to say, calculation of the distances between pairs of sequences and reconstruction of the phylogeny using the distance information. The phylogenetic tree is built by joining the two most similar sequences first, and then adding the other sequences one by one, in order of decreasing similarity. The numerical value on top of each line indicates the evolutionary distance for that respective species from the most recent common ancestor of IgE. According to these results, the human IgE sequence is most closely related to the chimpanzee, and then more distantly related to (in order of increasing distance) cat, dog, horse, pig, sheep, cow, Trichosurus, opossum, and duck-billed platypus. Rat and mouse IgE are believed to be most primitive (that is to say, least diverged from the most recent common ancestor) with regard to IgE molecular speciation.

These results, depicted by FIG. 15 and FIG. 16, show an extent of sequence identity and homology between the IgE sequences from different species that suggests that MHC-I-specific epitopes that are recognized by IgE-specific cytotoxic T-lymphocytes can be overlapping or similar or identical between two or more mammalian species. The MHC-I specificity of each such epitope is also dependent on the peptide-binding motifs of the respective MHC-I.

FIG. 17A depicts various building blocks or spliced blocks of the human immunoglobulin E heavy chain gene. The amino acid sequences of these blocks are supplied for the membrane exon sequences M1' (SEQ ID NO. 38), M2 (SEQ ID NO. 39), and M2' (SEQ ID NO. 40), and for the constant domain sequences CH4s (SEQ ID NO. 41), CH4 (SEQ ID NO. 42), CH4' (SEQ ID NO. 43), CH5 (SEQ ID NO. 44) of human immunoglobulin E heavy chain. The corresponding cDNA sequences of these blocks are supplied for the membrane exon sequences M1' (SEQ ID NO. 45), M2 (SEQ ID NO. 46), and M2' (SEQ ID NO. 47), and for the constant domain sequences CH4s (SEQ ID NO. 48), CH4 (SEQ ID NO. 49), CH4' (SEQ ID NO. 50), CH5 (SEQ ID NO. 51) of human immunoglobulin E heavy chain. These blocks may be spliced together in different orders, and those variants that are productively spliced (that is to say, translated into an IgE peptide product that is expressed at the cell surface, secreted, or displayed as a naturally processed and presented peptide on an MHC-I molecule at the cell surface) can serve as a source for deriving a sequence of a test peptide that preferably has the ability to elicit in a mammal a cytotoxic T-lymphocyte response to naturally processed and presented immunoglobulin E peptides.

Various differentially spliced human IgE isoforms were constructed (FIG. 12A) and reported according to the nomenclature of Zhang et al. (Zhang et al., 1992, *J. Exp. Med.*, 176:233; Zhang et al., 1994, *J. Biol. Chem.*, 269:456). These variant IgE polypeptides can incorporate a proximal 3' region (CH5) or distal 3' region (M2').

Various differentially spliced human IgE isoforms were constructed and reported according to the nomenclature of Zhang et al. (Zhang et al., 1992, *J. Exp. Med.*, 176:233; Zhang et al., 1994, *J. Biol. Chem.*, 269:456). These differentially spliced human IgE isoforms utilize different starting regions and combinations of membrane exons as depicted in FIG. 17A. Schematic diagrams of examples of these translated spliced human IgE messages are depicted in FIG. 17B. The abundant classical secreted human IgE isoform includes complete CH1 to CH4 constant region domains, as described above for various species. A less abundant secreted human IgE isoform contains a truncated CH4 (CH4') domain, and incorporates some distal 3' sequence (CH5) preceding the regular membrane exon region, or extending into a long M2' region. A short secreted human IgE isoform contains a truncated CH4 (CH4') and CH5 domains (Zhang et al., 1994, *J. Biol. Chem.*, 269:456). There are two classical plasma membrane-anchored IgE isoforms, a large membrane isoform containing the M1' and M2' domains, and a short membrane isoform containing the M1 and M2 domains. There also is a rare M2" membrane form that contains the CH4 domain and a truncated M2" domain (Peng et al., 1992, *J. Immunol.*, 148:129; Zhang et al., 1992, *J. Exp. Med.*, 176:233). The fully assembled products with differentially spliced frames can result in differing translated sequences due to shifting of the reading frame, even if the spliced messages overlap a large part of the exon sequence. IgE peptides, generated by the different isoforms and differing in the amino acid sequences of CH5 and membrane exons, can provide additional therapeutic targets for cytotoxic T-lymphocytes. Individuals, such as allergic patients, may have diverse IgE isoforms, which can serve as additional targets against which a cytotoxic T-lymphocyte response can be induced.

Example 8

Polynucleotides Encoding Immunogenic IgE Peptides Inserted into a Polypeptide Framework The following example describes a polynucleotide that encodes an immunogenic peptide inserted into a polypeptide framework itself encoded by the polynucleotide. This polynucleotide is useful, for example, as a DNA vaccine. The encoded immunogenic peptide inserted into the encoded polypeptide framework is also useful as a vaccine.

Green Fluorescent Protein as a Polypeptide Framework for an Immunogenic Peptide

Green fluorescent protein (GFP) is a 238-amino acid protein found in the jellyfish *Aequorea victoria* (Tsien, 1998, *Annu. Rev. Biochem.*, 67:509; Ormö et al., 1996 *Science*, 273:1392; Chalfie et al., 1994, *Science*, 263:802). GFP is used in the laboratory, for example as a visible marker for polypeptides or as a marker for gene expression. The GFP mutant $GFP_{UV}$ has the same fluorescence characteristics as the wild-type GFP (an excitation wavelength of about 395 nanometers and an emission wavelength of about 509 nanometers), but produces a 45-fold greater fluorescence signal (Crameri et al., 1996, *Nature Biotech.*, 14:315). $GFP_{UV}$ was chosen because it typically has greater expression rates, intracellular yield, and intracellular solubility than the wild-type GFP (Crameri et al., 1996, *Nature Biotech.*, 14:315). Monitoring the conformation of the $GFP_{UV}$ framework can be done by fluorescence measurements. $GFP_{UV}$ can be cloned into pCDNA3.1 for use as a DNA vaccine (Donnelly et al., 1977, *Annu. Rev. Immunol.*, 15:617; Gurunathan et al., 2002, *Annu. Rev. Immunol.*, 18:927), which is effective in eliciting a cytotoxic T-lymphocyte response upon different methods of administrations.

The structure of $GFP_{UV}$ consists of an eleven-strand beta-barrel wrapped around a central alpha-helix core. The barrel is formed by antiparallel beta-sheets interconnected by short alpha-helical "loops", which are exposed to the aqueous environment. The conformation of these loops is constrained by the overall beta-barrel structure of the protein, which is highly stable and resistant to distortion. Epitope peptide sequences, for example both cytotoxic T-lymphocyte epitopes and helper T-lymphocyte epitopes, can be inserted into these loops, where they maintain their immunogenicity (Billetta et al., 1991, *Proc. Natl. Acad. Sci.,* 88:4713; Gerloni, et al., 1997, *Nature Biotechnol.,* 15:876; Gerloni et al., 1999, *J. Immunol.,* 162:3782; Zaghouani et al., 1993, *Science,* 259:224; Zaghouani et al., 1993, *Eur. J. Immunol.,* 23:2746). Such inserted peptide sequences are exposed to the aqueous environment and can be relatively accessible to proteolytic degradation. Insertion in these GFP loops can extend the half-live of the cytotoxic T-lymphocyte IgE peptides thus expressed. The GFP chromophore is a modified tripeptide held in the interior of the beta-barrel, and its fluorescence is predictive of the protein's unperturbed conformation (Tsien, 1998, *Annu. Rev. Biochem.,* 67: 509; Ormö et al., 1996 *Science,* 273:1392).

FIG. 18 depicts the modified $GFP_{UV}$ vector used to express cytotoxic T-lymphocyte IgE peptides by a three-step PCR strategy. We modified the $GFP_{UV}$ vector rGFP-S65T (catalogue number #8364-1, Clontech, Calif.) by shortening the N-terminus lacZ fusion protein sequence, deleting all but the first 7 amino acids following the lacZ ATC initiation codon. Additional restriction enzyme sites were inserted into selected sites of two surface-exposed, highly constrained loops. These were site 6 in loop 6 (encompassing Ala 155 to Ile 161) (FIG. 18A) and site 7 in loop 7 (encompassing Lys 162 to Asp 183) (FIG. 18B). Site 6 is at Gln 157 in loop 6; the antisense primer ttgtttgtctgccgtgatgtatac (SEQ ID NO. 52) and sense primer tgaggtaccgcgcgcaagaatggaatcaaacgtaacttc (SEQ ID NO. 53), which contains Kpn I and BssH I restriction sites, were used at site 6 (FIG. 18A). Site 7 is at Glu 172 in loop 7; the sense primer tgatctagactgcaggatggattcgttcaactagcag (SEQ ID NO. 54), which contains Xba I and Pst I restriction sites, and common antisense primer tgatgatgatgatgatagagctcatccatgccatgtg (SEQ ID NO. 55), which contains a Sac I restriction site, were used at site 7 (FIG. 18B). These specific restriction enzyme sites were chosen for efficient end cutting, and ligation was carried out with oligonucleotides specifying defined sequences. Primers with restriction enzyme sites of interest, flanked by a partial $GFP_{UV}$ open reading frame containing loops 6 and 7, were used for amplifying about half of the $GFP_{UV}$ polypeptide. Intact $GFP_{UV}$, containing immunoglobulin E epitopes inserted at site 6 or at site 7, was then made by ligating two pieces of the amplified PCR products. The annealed product was amplified by another PCR amplification reaction to yield the final modified vector, which contained immunoglobulin E peptides cloned into $GFP_{UV}$ framework loops.

FIG. 19 depicts restriction enzyme digests of two clones (clone number 6/4 and clone number 6/5) obtained by the above three-step PCR strategy. These digests verified that the modified vector contained all the required sites as designed. Correct size of fragments, as predicted from the vector depicted in FIG. 18A and FIG. 18B, was observed for both clones following digestion by either SphI and Bgl II or by SphI and BssH I.

A series of six oligonucleotides encoding immunoglobulin E cytotoxic T-lymphocyte epitopes with Bgl II and Kpn I ends were cloned as inserts into site 6 of the $GFP_{UV}$ vector. Restriction digests of these site 6 clones (clones Ce3-BC, Ce3-DE, Ce3-FG, Ce2-3, Ce4-dest, and Ce4-crea) are depicted in FIG. 20A. The clones were expressed in *E. coli* JM109 cells and the cell lysates screened by Western blot, the results of which are depicted in FIG. 20B. The primary antibody was polyclonal rabbit anti-GFP (catalogue number #8367-2, Clontech, Calif.) and the secondary antibody was horseradish peroxidase labelled-goat anti-rabbit antibody (catalogue number #611-1322, Rockland Immunochemicals, Pa.). The cloned inserts were sequenced to verify the inserted epitopes. FIG. 20C depicts the nucleotide sequence of the six cloned immunoglobulin E cytotoxic T-lymphocyte epitopes. A parallel set of clones into site 7 of the $GFP_{UV}$ vector was also constructed. The site 6 and site 7 clones are tested for the ability to elicit a cytotoxic T-lymphocyte response against IgE naturally processed and presented on MHC-I molecules, for example on IgE-producing cells, or against IgE-bearing cells such as mast cells and basophils. In addition to GFP and its variants and mutants, other polypeptides (and the polynucleotides encoding them) or macromolecules can be used in an analogous manner to serve as frameworks for the IgE peptides. Examples of these include, but are not limited to, staphylococcal nuclease, fibronectin, immunoglobulin (Ig), heat shock protein (HSP), a phage, a ribosome, mRNA, a yeast cell surface, a bacterial cell surface, or a bacterial spore surface.

Purification of GFP and Antigenized GFP $GFP_{UV}$ contains ten histidine residues which can interact with metals such as Ni(II). In particular, His77, His81, and His231 are oriented within 7.5 Ångstrøm of each other near the top of the beta-barrel and can serve as a natural "histidine tag" for metal chelation. We purified both $GFP_{UV}$ and $GFP_{UV}$ antigenized with human IgE peptides from bacterial lysates by immobilized metal affinity chromatography on a nickel column. Cell pellets prepared from 500 ml LB medium were treated with 1 milligram per milliliter lysozyme. Cytosolic supernatants of lysates without inclusion bodies were collected by centrifugation, and dialyzed in 0.05 molar phosphate-0.25 molar NaCl buffer. The material was allowed to pass through the nickel column. Fluorescent material was bound to column as a visible band and was eluted with 2 molar sodium chloride. Throughout the purification process, the GFP$_{UV}$-enriched fraction was conveniently monitored by eye or visualized by illumination with a handheld UV lamp emitting at 365 nanometers. GFP$_{UV}$ was found to be homogenously distributed in the cytoplasm and the fluorescence-emitting material was obtained in the lysates and not in the inclusion bodies, which permitted a relatively high yield (50 milligrams protein per liter) of purified native protein. GFP$_{UV}$ represented about 70% of the harvested protein from the lysates. GFP$_{UV}$ and the antigenized GFP$_{UV}$ can be further purified to homogeneity by ion-exchange chromatography, such as by FPLC on a mono-Q column, or by other methods known in the art. The purifed proteins can be used to immunize a mammal and to elicit a cytotoxic T-lymphocyte response.

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

Thus we claim:

1. A method of identifying natural immunoglobulin E peptides presented by major histocompatibility complex class I molecules on IgE-producing cells that induce a cytotoxic T-lymphocyte response against natural IgE, comprising:

a) immunizing a first group of mice with an IgE peptide and a co-stimulatory factor, b) performing one or more assays to detect an immune response specific for the IgE peptide administered in step a) wherein the assays are chosen from the group consisting of:
   i) harvesting cytotoxic T-lymphocytes from the immunized mice and testing the cytotoxic T-lymphocytes for the ability to lyse target cells, wherein the target cells are IgE-producing cells,
   ii) measuring levels of circulating IgE in the sera of the immunized mice, and
   iii) measuring the number of IgE-producing cells in the immunized mice,
   wherein detection of a cytotoxic T-lymphocyte response, a decreased level of circulating IgE as compared to a control and/or a decreased number of IgE-producing cells as compared to a control indicates that the IgE peptide of step a) comprises a natural IgE peptide, c) generating peptides 8 to 10 amino acids in length which are truncations of the IgE peptide of step a), d) immunization a second group of mice with one of the peptides of step c) and e) performing one or more assays to detect an immune response specific for the IgE peptide administered in step d) wherein the assays are chosen from the group consisting of:
   i) harvesting cytotoxic T-lymphocytes from the immunized mice and testing the cytotoxic T-lymphocytes for the ability to lyse target cells, wherein the target cells are IgE-producing cells,
   ii) measuring levels of circulating IgE in the sera of the immunized mice, and
   iii) measuring the number of IgE-producing cells in the immunized mice,
   wherein detection of a cytotoxic T-lymphocyte response, a decreased level of circulating IgE as compared to a control and/or a decreased number of IgE-producing cells are compared to a control indicates that the IgE peptide of step d) is a natural IgE peptide.

2. The method of claim 1, wherein natural IgE peptides are from immunoglobulin E of human origin.

3. The method of claim 1, wherein the peptides of step c) are predicted to bind human MHC-I based on computer algorithms.

4. The method of claim 2, wherein mice are human MHC-I transgenic mice.

5. The method of claim 1, wherein natural IgE peptides are from immunoglobulin E of mammalian origin.

6. The method of claim 1, wherein the peptides of step c) comprise at least one D-amino acid residue.

7. A method of identifying second generation of IgE peptides that induce a cytotoxic T-lymphocyte response against a natural IgE peptide presented by major histocompatibility complex class I molecules on IgE-producing cells, comprising:

a) inserting a truncated IgE peptide identified in claim 1 into the complementarity-determining region (CDR) of an immunoglobulin to make a second generation IgE peptide, b) immunizing mice with the second generation of IGE peptide of step a), c) performing one or more assays to detect an immune response specific for the second generation IgE peptide administered in step b) wherein the assays are chosen from the group consisting of:

i) harvesting cytotoxic T-lymphocytes from the immunized mice and testing cytotoxic T-lymphocytes for the ability to lyse target cells, wherein the target cells are IgE-producing cells, ii) measuring levels of circulating IgE in the sera of the immunized mice, and iii) measuring the number of IgE-producing cells in the immunized mice, wherein detection of a cytotoxic T-lymphocyte response, a decreased level of circulating IgE as compared to a control and/or a decreased number of IgE-producing cells as compared to a control indicates that the IgE peptide of step a) comprises a natural IgE peptide.

8. The method of claim 7, wherein the inserted IgE peptide consists of a natural IgE peptide 8 to 10 amino acids in length.

9. The method of claim 7, wherein the inserted IgE peptide is of human origin.

10. The method of claim 7, wherein the inserted IgE peptide is of mammalian origin.

11. The method of claim 2, wherein IgE-producing cells are of human origin.

* * * * *